(12) United States Patent
Malhotra et al.

(10) Patent No.: US 11,771,692 B2
(45) Date of Patent: Oct. 3, 2023

(54) N-HYDROXYETHYL DIDEHYDROAZAPODOPHYLLOTOXINS AS GBP1 INHIBITORS AND METHODS OF OVERCOMING TREATMENT RESISTANCE IN CANCER

(71) Applicant: The Board of Trustees of the Leland Stanford Junior University, Stanford, CA (US)

(72) Inventors: Sanjay Malhotra, Palo Alto, CA (US); Vineet Kumar, Palo Alto, CA (US); Dhanir Tailor, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 72 days.

(21) Appl. No.: 16/971,639

(22) PCT Filed: Mar. 12, 2019

(86) PCT No.: PCT/US2019/021840
§ 371 (c)(1),
(2) Date: Aug. 20, 2020

(87) PCT Pub. No.: WO2019/178091
PCT Pub. Date: Sep. 19, 2019

(65) Prior Publication Data
US 2020/0375977 A1 Dec. 3, 2020

Related U.S. Application Data

(60) Provisional application No. 62/642,383, filed on Mar. 13, 2018.

(51) Int. Cl.
| | |
|---|---|
| *A61P 35/00* | (2006.01) |
| *C07D 215/14* | (2006.01) |
| *C07D 491/048* | (2006.01) |
| *C07D 491/153* | (2006.01) |
| *C07D 221/06* | (2006.01) |
| *C07D 221/18* | (2006.01) |
| *A61K 31/4741* | (2006.01) |
| *A61K 31/337* | (2006.01) |
| *A61K 31/473* | (2006.01) |
| *A61K 45/06* | (2006.01) |

(52) U.S. Cl.
CPC ........ *A61K 31/4741* (2013.01); *A61K 31/337* (2013.01); *A61K 31/473* (2013.01); *A61K 45/06* (2013.01); *A61P 35/00* (2018.01); *C07D 215/14* (2013.01); *C07D 491/048* (2013.01); *C07D 491/153* (2013.01)

(58) Field of Classification Search
CPC ... A61P 35/00; A61K 31/4741; A61K 31/337; A61K 31/473; A61K 45/06; C07D 215/14; C07D 491/048; C07D 491/153; C07D 221/06; C07D 221/18
See application file for complete search history.

(56) References Cited

U.S. PATENT DOCUMENTS

2017/0342086 A1 11/2017 Kumar et al.

FOREIGN PATENT DOCUMENTS

WO WO2013/122609 8/2013

OTHER PUBLICATIONS

RN2159060-52-1, 2017, registry database compound.*
RN1262219-94-2, 2011, registry database compound.*
Andreoli et al., 2014, Journal of Medicinal Chemistry, 57, 7916-7932.*
Andreoli et al. (2014) "Identification of the First Inhibitor of the GBP1 :PJM1 Interaction. Implications 1 for the Development of a New Class of Anticancer Agents against Paclitaxel Resistant Cancer Cells" J. Med. Chern., vol. 57, pp. 7916-7932.
Kumar et al. (2011) "Synthetic and Application Perspectives of Azapodophyllotoxins: Alternative 1 Scaffolds of Podophyllotoxin" Curr. Med. Chern., vol. 18, Iss. 25, 3853-3870.
Tailor et al. (2018) Inhibiting guanylate binding protein 1 (GBP1) impedes ovarian cancer progression Cancer Research, vol. 78, Iss. 13 Supplement,_ Jul. 1, 2018, Abstract No. 4951.

* cited by examiner

*Primary Examiner* — Sun Jae Yoo
(74) *Attorney, Agent, or Firm* — Pamela J. Sherwood; Bozicevic, Field & Francis LLP

(57) ABSTRACT

Compounds, compositions and methods are provided for the inhibition of GBP1. The subject inhibitor compounds can act by inhibiting GBP1 alone and/or GBP1: pro-survival kinase (e.g. serine/threonine-protein kinase pim-1 (PIM1)) interactions. Aspects of the subject methods include contacting a cellular sample with a GBP 1 inhibitor to inhibit the GBP 1 alone and/or GBP 1: PIM 1 interactions. Also provided are compositions and methods for treating cancer. In certain cases the cancer is resistant towards chemotherapy and radiation therapy.

21 Claims, 9 Drawing Sheets

N-HYDROXYETHYL DIDEHYDROAZAPODOPHYLLOTOXINS AS GBP1 INHIBITORS AND METHODS OF OVERCOMING TREATMENT RESISTANCE IN CANCER

CROSS-REFERENCE

This application claims the benefit of U.S. Provisional Patent Application No. 62/642,383, filed Mar. 13, 2018, which application is incorporated herein by reference in its entirety.

INTRODUCTION

Radiotherapy (RT) remains an essential treatment tool for cancer treatment, either as adjuvant therapy or as primary treatment for patients that are unfit for surgery. Often, RT is also coupled with chemotherapy. Resistance to radiation therapy, also known as radioresistance, is a major clinical problem in cancer patients and greatly affects patient quality of life (Begg, A. C. et al, Nature Reviews Cancer 2011, 11(4), 239-253). Though, the resistance to radiation therapy and current chemotherapeutic agents such as paclitaxel, carboplatin, doxorubicin, is a major cause of therapy failure in cancer patients, exact mechanisms leading to the treatment resistance remain unclear (Holohan, C. et al. Nature Reviews Cancer 2013, 13(10), 714-726; Kyrgiou, M. et al. Journal of the National Cancer Institute 2006, 98(22), 1655-1663). An effective means by which to reverse treatment resistance in refractory cancers remains an unaddressed clinical need. The failure of first line chemotherapy and radiation therapy for ovarian cancer patients emphasizes the need for novel therapeutic targets with new mechanisms of action, and drugs that can safely modulate these targets.

Past Studies have identified a large-GTPase known as the Guanylate-Binding Protein 1 (GBP1), as playing a major role in cancer cells stressed in a setting of hypoxia and low nutrient supply. GBP1 is induced by interferon IFNγ and involved in the regulation of proliferation and endosome fate in endothelial cells and macrophages. Cytokine- and hypoxiainduced overexpression of GBP1 in cancer leads to increased production of Class III β-tubulin (βTUB3) and recruitment of kinases such as PIM1 into the cytoskeleton, which supports tumor survival and growth (De Donato, M. et al. Journal of Cellular Physiology 2012, 227(3), 1034-1041). GBP1 overexpression has been associated with paclitaxel and radioresistance in ovarian cancer and enhanced cell invasion in glioblastoma multiforme (GBM) (Duan, Z. F. et al. Cancer Chemotherapy and Pharmacology 2006, 57(1), 25-33; Li, M. et al. Journal of Experimental Medicine 2011, 208(13), 2657-2673). Knock down of GBP1 expression using shRNA in vitro or prior to in vivo orthotopic implantation in glioblastoma have demonstrated reduced tumor growth rates and increased sensitivity to chemotherapy or radiotherapy. Preclinical models and study of patient samples have also demonstrated a strong correlation between taxane-resistance and increased expression of βTUB3, PIM1, and GBP1 in ovarian and lung cancer. Recent proteomic studies reveled GBP1 as a potential biomarker that is overexpressed in oral cavity squamous cell carcinoma (OSCC). Expression of GBP1 was also highly upregulated in esophageal squamous cell carcinoma (ESCC) and its overexpression was significantly correlated with lymph node metastasis in patients (Li. L. et al. Discovery Medicine 2015, 20(112), 369-378). Further, clinical studies have directly linked the overexpression of GBP1 with radioresistance in head and neck cancer (HNC). Recent cDNA microarray studies carried out on human and murine clinically relevant radioresistant cell lines showed overexpression of GBP1 in all these cells (Fukumoto, M. et al. Cancer Science 2014, 105(10), 1351-1359).

However, mechanistic insight of the relationship between GBP1 and radioresistance is still very limited. Detailed studies of the necessity and sufficiency of both upstream and downstream effectors of GBP1 are, therefore, needed to define a detailed treatment mechanism, which will be important in the design and execution of studies to assess the clinical potential of GBP1 inhibition.

SUMMARY

Compounds, compositions and methods are provided for the inhibition of GBP1. The subject inhibitor compounds can act by inhibiting GBP1: pro-survival kinase (e.g. serine/threonine-protein kinase pim-1 (PIM1)) interactions. Aspects of the subject methods include contacting a cellular sample with an effective amount of the GBP1 inhibitor to inhibit the GBP1:PIM1 interactions.

In some embodiments compositions and methods are provided for treating cancer. In certain cases the cancer is resistant to chemotherapy and radiation therapy. Aspects of the methods include administering to a subject an effective amount of a GBP1 inhibitor to inhibit GBP1:PIM1 interactions and treat the subject for cancer. In certain cases the cancer is selected from ovarian cancer, colorectal cancer, prostate cancer, head and neck cancer, lung cancer and breast cancer.

In some embodiments methods are provided for administering one or more additional therapeutic regimens in combination with a GBP1 inhibitor. In certain cases the additional therapeutic regimen is an active agent, including without limitation a chemotherapeutic agent (e.g. paclitaxel). In some embodiments the therapeutic regimen comprises administering radiation therapy to a subject either before or after administering a subject GBP1 inhibitor. The radiation therapy can be administered at a dosage and/or frequency effective to reduce radiation damage to the subject, but still instigate an immune response. In certain cases, the GBP1 inhibitor sensitizes the cancer to chemotherapy and radiation therapy.

These and other advantages and features of the disclosure will become apparent to those persons skilled in the art upon reading the details of the compositions and methods of use, which are more fully described below.

BRIEF DESCRIPTION OF THE FIGURES

The invention is best understood from the following detailed description when read in conjunction with the accompanying figures. It is emphasized that, according to common practice, the various features of the figures are not to-scale. On the contrary, the dimensions of the various features are arbitrarily expanded or reduced for clarity. Included in the drawings are the following figures. It is understood that the figures, described below, are for illustration purposes only. The figures are not intended to limit the scope of the present teachings in any way.

FIG. 1, panel A shows cell viability using MTT assay on GBP1 overexpressed (OV), knockdown (KD), vector controlled (VC) and scrambled control (SC) SCC-90 cells (Head and Neck Cancer) after 48 h of plating. FIG. 1, panel B shows representative images of migrated SCC-90 cells after 16 h through Boyden chambers, indicating that GBP1 OV induces and KD reduces the cell migration property of HNC cells. FIG. 1, panel C shows western blots of E-cad and Vimentin. FIG. 1, panel D shows HNC cells exposed with hypoxic condition (1% Oxygen) for 24 h followed by immunostaining for GBP1 and Hif1α antibodies, visualized under a confocal microscope. FIG. 1, panel E shows western blots of VEGF and IL-6 in cell lysates and media. FIG. 1, panel F shows western blots of B2M and β-actin indicating that GBP1 overexpression inhibits the expression of B2M.

FIG. 2, panel A illustrates GBP1 modulated (OV, KD, VC and SC) SCC-90 cells treated with radiation (0, 2.5, 5 and 10 Gy) for 24 h and stained after 8 days with crystal violet. Top right panel shows representative images of clonogenic assay. FIG. 2, panel B illustrates that lysate from VC and GBP1 OV cells were immunoblot for LGR5, a stemness marker. FIG. 2, panel C graphs the GBP1 modulated cells analyzed using flow cytometry for CD44 and CD133 (stemness markers) immunostaining.

FIG. 3, panel A illustrates the effects of SU093 on survival of human normal HEK293 cell line and ovarian cancer cell lines OVCAR8 & SKOV3 cells via MTT assay. FIG. 3, panel B illustrates the effect of SU093 on GBP1 and PIM1 expression in OVCAR8 cells. FIG. 3, panel C illustrates that SU093 exhibited dose-dependent inhibition of clonogenic potential in OVCAR8 cells. FIG. 3, panel D illustrates quantification of overexpression and knockdown of GBP1 gene in stably transfected OVCAR8 cells. FIG. 3, panel E illustrates cytotoxicity of SU093 as evaluated in GBP1-OV, GBP1-WT and GBP1-KD OVCAR8 via MTT assay.

FIG. 4, panel B illustrates the effect of SU093 on cell cycle distribution showing G1 phase arrest. FIG. 4, panel C illustrates the effect of SU093 on cell cycle and cell death regulators analyzed by immunostaining. FIG. 4, panel D illustrates mitochondria stained with MitoTracker Red CMXRos and visualized by confocal microscopy indicating mitochondrial dysfunction in OVCAR8 cells. FIG. 4, panel E illustrates the effect of SU093 on active mitochondrial mass in OVCAR8 cells. Data are shown as mean SD of triplicate samples. *, $P<0.05$, significantly different compared with respective controls by one-way ANOVA followed by Dunnett's test. FIG. 4, panel F illustrates confocal microscopy experiments on OVCAR8 cells were treated with 1 nM of SU093 for 6 h and immune-stained with β-tubulin and GBP1 antibodies and visualized under confocal microscope, indicating that SU093 inhibits the nuclear translocation of GBP1 protein and reduces the tubulin expression.

FIG. 5, panel A graphs cells that were pre-treated with 0, 0.5 and 1 nM SU093 for 24 h followed by 0, 5 & 10 Gy radiation treatment and incubated for 96 h. FIG. 5, panel B illustrates cell cycle analysis of SU093 and radiation combination treatment in OVCAR8. FIG. 5, panel C illustrates the effect of SU093 on OVCAR8 cells in hypoxic condition (0.5% $O_2$) FIG. 5, panel D graphs hypoxic cells that were pre-treated with SU093 for 24 h followed by 5 and 10 Gy radiation. Data are shown as mean SD of triplicate samples. *, $P<0.05$, significantly different compared with respective controls by Student t-test. FIG. 5, panel E illustrates the synergistic cytotoxic effect observed by pre-treatment of OVCAR8 cells with 0.5 nM SU093 for 24 h followed by 1, 5 and 10 nM paclitaxel treatment for 24 h.

FIG. 6, panel A illustrates western blot of SCC-90 cells treated with SU093 for 24 h, indicating inhibition in GBP1 expression. FIG. 6, panel B illustrates CHC assay, indicating that SU093 leads to GBP1 protein degradation. FIG. 6, panel C shows cell viability studies using MTT assay on SCC-90 cells (wild type, overexpressed and knockdown with GBP1) treated with SU093 (0.5-1000 nM) for 48 h. FIG. 6, panel D illustrates confocal microscopy of SCC-90 cells treated with SU093 (50 nM) for 6 h and immunostained with β-tubulin and GBP1 antibodies, indicating that SU093 inhibits the nuclear translocation of GBP1 protein and reduces the tubulin expression. FIG. 6, panel E shows clonogenic assay suggesting that treatment of SCC-90 cells treated with SU093 (50 nM) has a radiosensitization effect. FIG. 6, panel F shows cell cycle analysis of PI-stained SCC-90 cells treated with SU093 (50 nM) and/or 10 Gy radiation for 24 h, demonstrating that combination treatment causes G2/M phase arrest followed by cell death.

FIG. 7, panel B illustrates the drug concentration in harvested ovaries and liver of C57BL/6 mice after 14 days of administration with SU093 (100 mg/kg) by daily IP injection.

FIG. 8, panel A illustrate representative images of mice after 42 days of drug treatment, showing tumor regression compared to control. FIG. 8, panel B shows tumor volume/mouse as a function of time. FIG. 8, panel C illustrates tumor weight/mouse at the end of study. Data shown are mean±STDV from 5 mice in each group. *$P<0.001$, compared with respective control. FIG. 8, panel D illustrates liver toxicity parameters at the end of 42 days showing no significant difference between control, SU093 and SU056.

FIG. 9, panel A shows tumor volume/mouse as a function of time. FIG. 9, panel B illustrates tumor weight/mouse at the end of study. Data shown are mean±STDV from 3 mice in each group. *$P<0.001$, compared with respective control for SU093 and SU056.

DEFINITIONS

Figure 1:
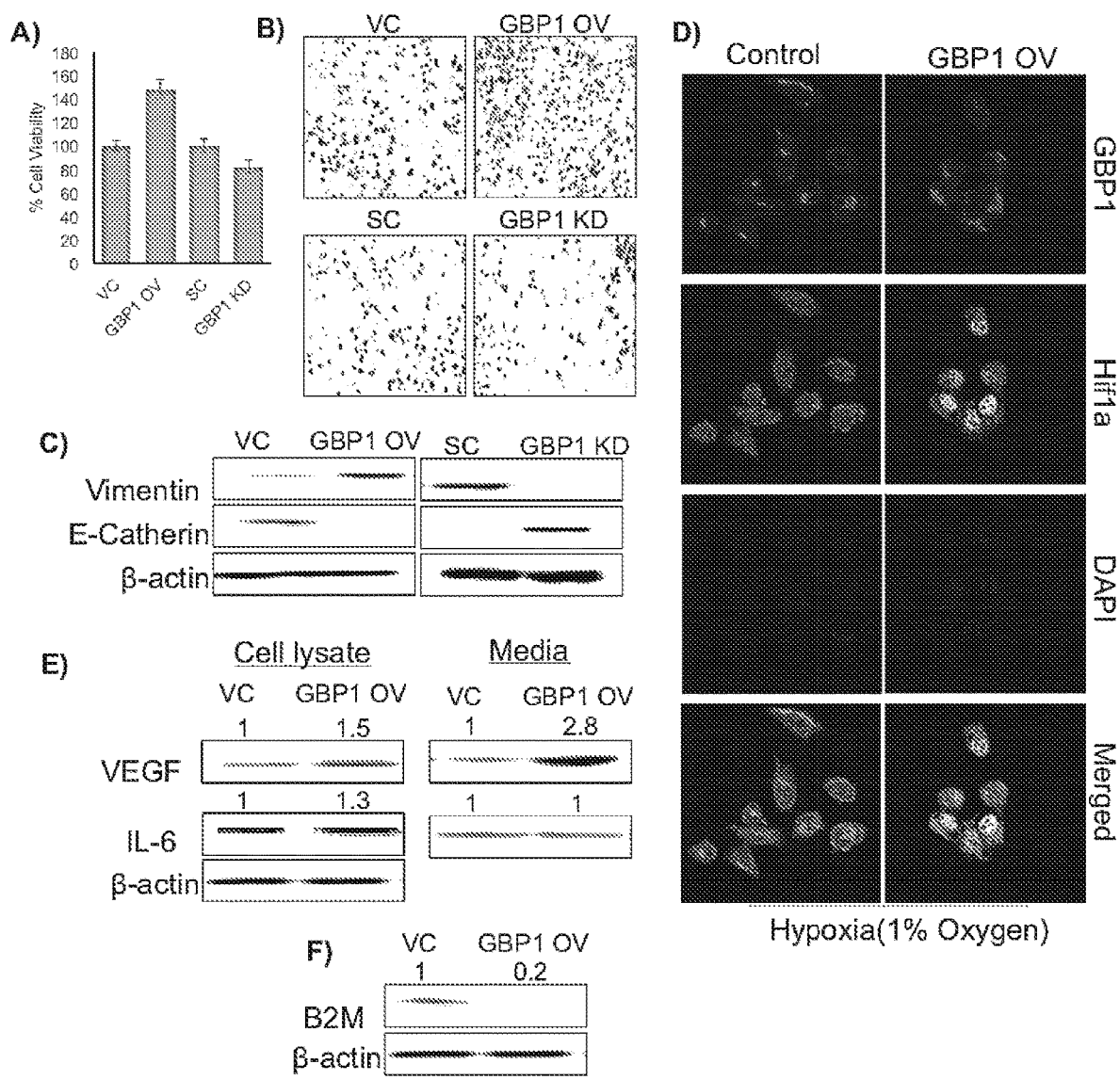
FIG. 1, panels A-F illustrates the effects of GBP1 modulation in migration and microenvironment in HNC cells.

Before embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Any methods and materials similar or equivalent to those described herein can also be used in the practice or testing of embodiments of the present disclosure.

It must be noted that as used herein and in the appended claims, the singular forms "a", "and", and "the" include plural referents unless the context clearly dictates otherwise. Thus, for example, reference to "a compound" includes not only a single compound but also a combination of two or more compounds, reference to "a substituent" includes a single substituent as well as two or more substituents, and the like.

In describing and claiming the present invention, certain terminology will be used in accordance with the definitions set out below. It will be appreciated that the definitions provided herein are not intended to be mutually exclusive. Accordingly, some chemical moieties may fall within the definition of more than one term.

As used herein, the phrases "for example," "for instance," "such as," or "including" are meant to introduce examples that further clarify more general subject matter. These examples are provided only as an aid for understanding the disclosure, and are not meant to be limiting in any fashion.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "active agent," "antagonist", "inhibitor", "drug" and "pharmacologically active agent" are used interchangeably herein to refer to a chemical material or compound which, when administered to an organism (human or animal) induces a desired pharmacologic and/or physiologic effect by local and/or systemic action.

As used herein, the terms "treatment," "treating," and the like, refer to obtaining a desired pharmacologic and/or physiologic effect, such as reduction of tumor burden. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease (e.g., reduction of tumor burden).

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The terms "individual," "host," "subject," and "patient" are used interchangeably herein, and refer to an animal, including, but not limited to, human and non-human primates, including simians and humans; rodents, including rats and mice; bovines; equines; ovines; felines; canines; and the like. "Mammal" means a member or members of any mammalian species, and includes, by way of example, canines; felines; equines; bovines; ovines; rodentia, etc. and primates, e.g., non-human primates, and humans. Non-human animal models, e.g., mammals, e.g. non-human primates, murines, lagomorpha, etc. may be used for experimental investigations.

As used herein, the terms "determining," "measuring," "assessing," and "assaying" are used interchangeably and include both quantitative and qualitative determinations.

A "therapeutically effective amount" or "efficacious amount" means the amount of a compound that, when administered to a mammal or other subject for treating a disease, condition, or disorder, is sufficient to effect such treatment for the disease, condition, or disorder. The "therapeutically effective amount" will vary depending on the compound, the disease and its severity and the age, weight, etc., of the subject to be treated.

The term "unit dosage form," as used herein, refers to physically discrete units suitable as unitary dosages for human and animal subjects, each unit containing a predetermined quantity of a compound (e.g., an aminopyrimidine compound, as described herein) calculated in an amount sufficient to produce the desired effect in association with a pharmaceutically acceptable diluent, carrier or vehicle. The specifications for unit dosage forms depend on the particular compound employed and the effect to be achieved, and the pharmacodynamics associated with each compound in the host.

A "pharmaceutically acceptable excipient," "pharmaceutically acceptable diluent," "pharmaceutically acceptable carrier," and "pharmaceutically acceptable adjuvant" means an excipient, diluent, carrier, and adjuvant that are useful in preparing a pharmaceutical composition that are generally safe, non-toxic and neither biologically nor otherwise undesirable, and include an excipient, diluent, carrier, and adjuvant that are acceptable for veterinary use as well as human pharmaceutical use. "A pharmaceutically acceptable excipient, diluent, carrier and adjuvant" as used in the specification and claims includes both one and more than one such excipient, diluent, carrier, and adjuvant.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal, intramuscular, subcutaneous, and the like.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias.

In some embodiments a cancer treated with the methods described herein is a solid tumor, including particularly carcinomas. Examples of solid tumors include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

Ovarian cancers are of interest, and include epithelial carcinoma, which makes up 85% to 90% of ovarian cancers. The main histologic types of ovarian epithelial carcinomas include serous, endometrioid, clear cell, mucinous, mixed tumors, and several rare malignancies, including Brenner and transitional cell cancers. The majority of ovarian carcinomas are serous, and these cancers are either high-grade serous carcinoma (HGSC) or low-grade serous carcinoma (LGSC). HGSCs are the most common histologic type of malignancy of the ovary, fallopian tube, and peritoneum, as noted above. LGSC is less common. Other ovarian cancers include germ cell malignancies, e.g. dysgerminomas, immature teratoma, and endodermal sinus tumors (called EST and yolk sac tumors), which include embryonal carcinoma; stromal malignancies; granulosa cell tumors, theca cell malignancies, and mixtures of these two types.

Head and neck cancers are of interest particularly squamous cell carcinomas of the head and neck.

As used herein, the phrase "having the formula" or "having the structure" is not intended to be limiting and is used in the same way that the term "comprising" is commonly used. The term "independently selected from" is used herein to indicate that the recited elements, e.g., R groups or the like, can be identical or different.

As used herein, the terms "may," "optional," "optionally," or "may optionally" mean that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group $CH_3C(O)$—

The term "alkyl" as used herein refers to a branched or unbranched saturated hydrocarbon group (i.e., a monoradical) typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms. "Substituted alkyl" refers to alkyl substituted with one or more substituent groups, and this includes instances wherein two hydrogen atoms from the same carbon atom in an alkyl substituent are replaced, such as in a carbonyl group (i.e., a substituted alkyl group may include a —C(=O)— moiety). The terms "heteroatom-containing alkyl" and "heteroalkyl" refer to an alkyl substituent in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The term "substituted alkyl" is meant to include an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

The term "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein may contain 2 to about 18 carbon atoms, and for example may contain 2 to 12 carbon atoms. The term "lower alkenyl" intends an alkenyl group of 2 to 6 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein may contain 2 to about 18 carbon atoms, and such groups may further contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "C1-C6 alkoxy" or "lower alkoxy" herein may, for example, may contain 1 to 3 carbon atoms, and as a further example, such substituents may contain 1 or 2 carbon atoms (i.e., methoxy and ethoxy).

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

As used herein, "carbocycle" or "carbocyclic ring" is intended to mean any stable monocyclic, bicyclic, or tricyclic ring having the specified number of carbons, any of which may be saturated, unsaturated, or aromatic. For example a C3-14 carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when a covalent bond or one or more carbon atoms link two non-adjacent carbon atoms in a ring. In one embodiment, bridge rings are one or two carbon atoms. It is noted that a bridge always converts a monocyclic ring into a bicyclic ring. When a ring is bridged, the substituents recited for the ring may also be present on the bridge. Fused (e.g., naphthyl and tetrahydronaphthyl) and spiro rings are also included.

The term "aryl" as used herein, and unless otherwise specified, refers to an aromatic substituent generally, although not necessarily, containing 5 to 30 carbon atoms and containing a single aromatic ring or multiple aromatic rings that are fused together, directly linked, or indirectly linked (such that the different aromatic rings are bound to a common group such as a methylene or ethylene moiety). Aryl groups may, for example, contain 5 to 20 carbon atoms, and as a further example, aryl groups may contain 5 to 12 carbon atoms. For example, aryl groups may contain one aromatic ring or two or more fused or linked aromatic rings (i.e., biaryl, aryl-substituted aryl, etc.). Examples include phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. Aryl is intended to include stable cyclic, heterocyclic, polycyclic, and polyheterocyclic unsaturated $C_3$-$C_{14}$ moieties, exemplified but not limited to phenyl, biphenyl, naphthyl, pyridyl, furyl, thiophenyl, imidazoyl, pyrimidinyl, and oxazoyl; which may further be substituted with one to five members selected from hydroxy, $C_1$-$C_8$ alkoxy, $C_1$-$C_8$ branched or straight-chain alkyl, acyloxy, carbamoyl, amino, N-acylamino, nitro, halogen, trifluoromethyl, cyano, and carboxyl (see e.g. Katritzky, Handbook of Heterocyclic Chemistry). If not otherwise indicated, the term "aryl" includes unsubstituted, substituted, and/or heteroatom-containing aromatic substituents.

The terms "halo" and "halogen" are used in the conventional sense to refer to a chloro, bromo, fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the terms "heterocyclic" or "heterocycle" refer to a cyclic substituent that is heteroatom-containing, the terms "heteroaryl" and "heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, furyl, pyrimidinyl, imidazolyl, 1,2,4-triazolyl, tetrazolyl, etc., and examples of heteroatom-containing alicyclic groups are pyrrolidino, morpholino, piperazino, piperidino, tetrahydrofuranyl, etc.

"Heteroaryl" refers to an aromatic group of from 1 to 15 carbon atoms, such as from 1 to 10 carbon atoms and 1 to 10 heteroatoms selected from oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

As used herein, the terms "Heterocycle," "heterocyclic," "heterocycloalkyl," and "heterocyclyl" refer to a saturated or unsaturated group having a single ring or multiple condensed rings, including fused bridged and spiro ring systems, and having from 3 to 15 ring atoms, including 1 to 4 hetero atoms. These ring atoms are selected from nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —SO$_2$— moieties.

Examples of heterocycle and heteroaryls include, but are not limited to, 1,3-dioxolane, 1,4-dioxane, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl, —SO$_2$-heteroaryl, and fused heterocycle.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation, functional groups, and the hydrocarbyl moieties C1-C24 alkyl (including C1-C18 alkyl, further including C1-C12 alkyl, and further including C1-C6 alkyl), C2-C24 alkenyl (including C2-C18 alkenyl, further including C2-C12 alkenyl, and further including C2-C6 alkenyl), C2-C24 alkynyl (including C2-C18 alkynyl, further including C2-C12 alkynyl, and further including C2-C6 alkynyl), C5-C30 aryl (including C5-C20 aryl, and further including C5-C12 aryl), and C6-C30 aralkyl (including C6-C20 aralkyl, and further including C6-C12 aralkyl). The above-mentioned hydrocarbyl moieties may be further substituted with one or more functional groups or additional hydrocarbyl moieties such as those specifically enumerated. Unless otherwise indicated, any of the groups described herein are to be interpreted as including substituted and/or heteroatom-containing moieties, in addition to unsubstituted groups.

By the term "functional groups" is meant chemical groups such as halo, hydroxyl, sulfhydryl, C1-C24 alkoxy, C2-C24 alkenyloxy, C2-C24 alkynyloxy, C5-C20 aryloxy, acyl (including C2-C24 alkylcarbonyl (—CO-alkyl) and C6-C20 arylcarbonyl (—CO-aryl)), acyloxy (—O-acyl), C2-C24 alkoxycarbonyl (—(CO)—O-alkyl), C6-C20 aryloxycarbonyl (—(CO)—O-aryl), halocarbonyl (—(CO)—X where X is halo), C2-C24 alkylcarbonato (—O—(CO)—O-alkyl), C6-C20 arylcarbonato (—O—(CO)—O-aryl), carboxy (—COOH), carboxylato (—COO—), carbamoyl (—(CO)—NH$_2$), mono-substituted C1-C24 alkylcarbamoyl (—(CO)—NH(C1-C24 alkyl)), di-substituted alkylcarbamoyl (—(CO)—N(C1-C24 alkyl)$_2$), mono-substituted arylcarbamoyl (—(CO)—NH-aryl), thiocarbamoyl (—(CS)—NH$_2$), carbamido (—NH—(CO)—NH$_2$), cyano (—C≡N), isocyano (—N+≡C—), cyanato (—O—C≡N), isocyanato (—O—N+≡C—), isothiocyanato (—S—C≡N), azido (—N=N+=N—), formyl (—(CO)—H), thioformyl (—(CS)—H), amino (—NH$_2$), mono- and di-(C1-C24 alkyl)-substituted amino, mono- and di-(C5-C20 aryl)-substituted amino, C2-C24 alkylamido (—NH—(CO)-alkyl), C5-C20 arylamido (—NH—(CO)-aryl), imino (—CR=NH where R=hydrogen, C1-C24 alkyl, C5-C20 aryl, C6-C20 alkaryl, C6-C20 aralkyl, etc.), alkylimino (—CR=N(alkyl), where R=hydrogen, alkyl, aryl, alkaryl, etc.), arylimino (—CR=N(aryl), where R=hydrogen, alkyl, aryl, alkaryl, etc.), nitro (—NO$_2$), nitroso (—NO), sulfo (—SO$_2$—OH), sulfonato (—SO$_2$—O—), C1-C24 alkylsulfanyl (—S-alkyl; also termed "alkylthio"), arylsulfanyl (—S-aryl; also termed "arylthio"), C1-C24 alkylsulfinyl (—(SO)-alkyl), C5-C20 arylsulfinyl (—(SO)-aryl), C1-C24 alkylsulfonyl (—SO2-alkyl), C5-C20 arylsulfonyl (—SO$_2$-aryl), phosphono (—P(O)(OH)$_2$), phosphonato (—P(O)(O—)$_2$), phosphinato (—P(O)(O—)), phospho (—PO$_2$), and phosphino (—PH$_2$), mono- and di-(C1-C24 alkyl)-substituted phosphino, mono- and di-(C5-C20 aryl)-substituted phosphine. In addition, the aforementioned functional groups may, if a particular group permits, be further substituted with one or more additional functional groups or with one or more hydrocarbyl moieties such as those specifically enumerated above.

When the term "substituted" appears prior to a list of possible substituted groups, it is intended that the term apply to every member of that group. For example, the phrase "substituted alkyl and aryl" is to be interpreted as "substituted alkyl and substituted aryl."

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from O, N and S, of which N may have —H or $C_1$-$C_3$ alkyl substitution; and each W is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-R^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —$P(O)O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR^{70}C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

Unless indicated otherwise, the nomenclature of substituents that are not explicitly defined herein are arrived at by naming the terminal portion of the functionality followed by the adjacent functionality toward the point of attachment.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

In certain embodiments, a substituent may contribute to optical isomerism and/or stereo isomerism of a compound.

Salts, solvates, hydrates, and prodrug forms of a compound are also of interest. All such forms are embraced by the present disclosure. Thus the compounds described herein include salts, solvates, hydrates, prodrug and isomer forms thereof, including the pharmaceutically acceptable salts, solvates, hydrates, prodrugs and isomers thereof. In certain embodiments, a compound may be a metabolized into a pharmaceutically active derivative.

Unless otherwise specified, reference to an atom is meant to include isotopes of that atom. For example, reference to H is meant to include $^1H$, $^2H$ (i.e., D) and $^3H$ (i.e., T), and reference to C is meant to include $^2C$ and all isotopes of carbon (such as $^{13}C$).

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Definitions of other terms and concepts appear throughout the detailed description below.

DETAILED DESCRIPTION OF THE EMBODIMENTS

As summarized above, aspects of the present disclosure include compounds, compositions and methods for the inhibition of GBP1. Aspects of the methods include contacting a sample with a GBP1 inhibitor to inhibit GBP1: pro-survival kinase (e.g. serine/threonine-protein kinase pim-1 (PIM1)) interactions.

Also provided are compositions and methods for treating cancer. Aspects of the methods include administering to a subject an effective amount of a GBP1 inhibitor to treat the subject for cancer. In certain cases the cancer is resistant towards radiation therapy and chemotherapy. In certain aspects, the GBP1 inhibitor is administered in combination with another active agent (e.g. a chemotherapeutic agent) and/or radiation therapy. In certain cases, the GBP1 inhibitor sensitizes the cancer to chemotherapy and/or radiation treatment. In some cases the cancer is a solid tumor. In some cases the solid tumor is a carcinoma. In some cases a cancer is selected from ovarian carcinomas (OC); colorectal cancer, e.g. adenocarcinomas; prostate cancer, e.g. adenocarcinoma of the prostate; head and neck cancer (HNC), e.g. squamous cell carcinomas; lung cancer, e.g. small cell lung cancer, non-small cell lung cancers such as squamous cell carcinoma, adenocarcinoma, and large cell carcinoma, etc.; and breast cancer, e.g. ductal carcinoma in situ, invasive ductal carcinoma, invasive lobular carcinoma; and the like. In certain embodiments the cancer is ovarian cancer. In other embodiments, the cancer is head and neck cancer.

These compounds and methods find use in a variety of applications in which inhibition of GBP1 is desired.

GBP1-Inhibitor Compounds

As summarized above, aspects of the disclosure include GBP1 inhibitor compounds. In some cases, the compounds include azapodophyllotoxin core structures. Exemplary compounds including azapodophyllotoxin core structures are set forth in the following structures 1-23 and formulae I-VII.

In some embodiments there is provided a GBP1 inhibitor of formula (I):

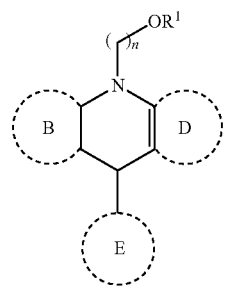
(I)

wherein:
$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
Ring B and Ring E are each independently selected from a $C_{5-6}$ membered carbocycle, a substituted $C_{5-6}$ membered carbocycle a $C_{5-6}$ membered heteroaryl, a substituted $C_{5-6}$ membered heteroaryl, a $C_{5-6}$ membered heterocycle containing up to two atoms selected from N, O or S and a substituted $C_{5-6}$ membered heterocycle containing up to two atoms selected from N, O or S (e.g. pyrrole, imidazole, pyrazole, furan, oxazole, isoxazole, thiophene, thiazole, isothiazole, pyridine, pyrimidine, 2-H-pyran, 2-H-thiopyran);
Ring D is selected from a $C_{5-6}$ carbocycle, a $C_{5-6}$ heterocycle containing up to two atoms selected from N, O or S, a substituted $C_{5-6}$ carbocycle, and a substituted $C_{5-6}$ heterocycle containing up to two atoms selected from N, O or S (e.g. 2-furanone, 1,3-dioxolane, cyclopentane, cyclopentene, 1,4-dioxane, cyclohexane, cyclohexene, cyclohexanone); and
n is an integer from 1 to 6,
or a pro-drug, a pharmaceutically acceptable salt or a solvate thereof.

In some embodiments of formula (I), $R^1$ is H. In other embodiments, $R^1$ is a substituent other than H, such as alkyl, alkoxy, carbocycle, heterocycle, heteroaryl or a protecting group, each of which may be optionally further substituted with one or more substituents.

In certain embodiments of formula (I), the D ring is selected from:

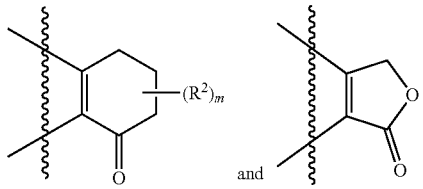
and wherein:
each $R^2$ are independently selected from alkyl, substituted alkyl, acyl, substituted acyl, alkoxy, substituted alkoxy, carbocycle, substituted carbocycle, heterocycle, substituted heterocycle, heteroaryl, substituted heteroaryl, F, $CF_3$, CN, $NO_2$ and methoxy; and
m is an integer from 0 to 6. Thus, the compound of formula (I) may be a compound of formula (IA) or (IB):

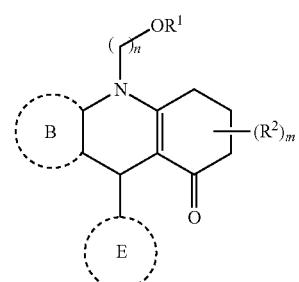
(IA)

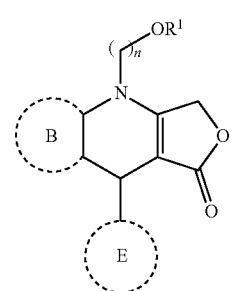
(IB)

wherein the Ring B and Ring E are each independently any of the groups as defined above for a compound of formula (I).

In certain embodiments of a GBP1 inhibitor of any of formulas (I)-(IB), the B ring or E ring are each independently selected from aryl, substituted aryl, pyrrole, substituted pyrrole, imidazole, substituted imidazole, pyrazole, substituted pyrazole, furan, substituted furan, oxazole, substituted oxazole, isoxazole, substituted isoxazole, thiophene, substituted thiophene, thiazole, substituted thiazole, isothiazole, substituted isothiazole, pyridine, substituted pyridine, pyrimidine, substituted pyrimidine, 2-H-pyran, substituted 2-H-pyran, 2-H-thiopyran and substituted 2-H-thiopyran.

In some cases of a GBP1 inhibitor of any of formulas (I)-(IB), the B ring is of the formula (B1)

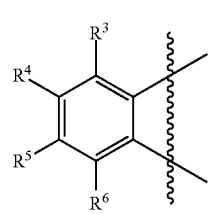
(B1)

wherein:
$R^3$, $R^4$, $R^5$ and $R^6$ are each independently selected from H, OH, methoxy, halogen, $CF_3$, CN and $NO_2$;
or any of $R^4$ and $R^5$, $R^3$ and $R^4$, $R^5$ and $R^6$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S (e.g. 2-furanone, 1,3-dioxolane, cyclopentane, cyclopentene, 1,4-dioxane, cyclohexane, cyclohexene, cyclohexanone). Thus, the compound of formula (I) may be a compound of formulae (IC), (ID) or (IE):

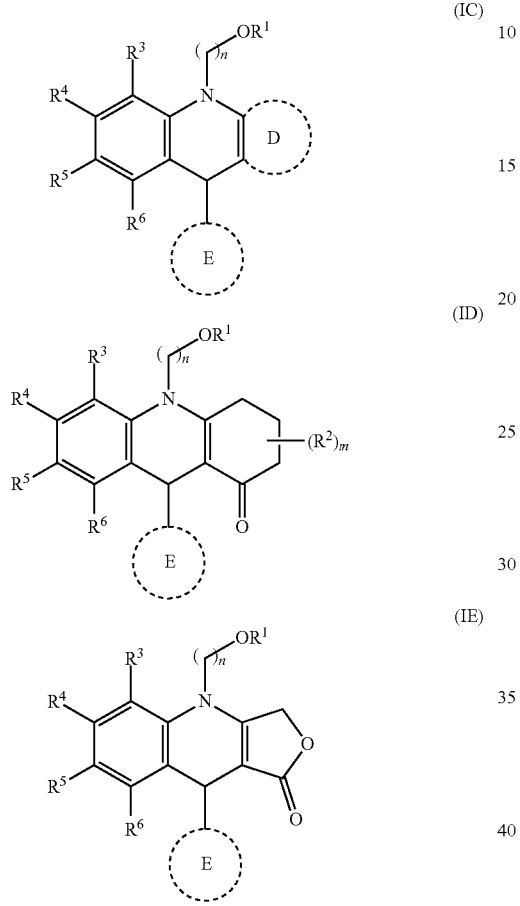

wherein the Ring D and Ring E are each independently any of the groups as defined above for a compound of formula (I).

In some cases of a GBP1 inhibitor of any of formulas (I)-(IE), the E ring is of the formula (E1):

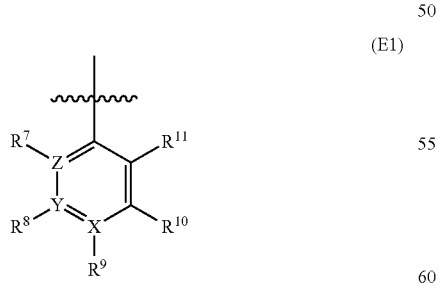

wherein:
X, Y and Z are each independently selected from C or N; and
$R^7$, $R^8$, $R^9$, $R^{10}$ and $R^{11}$ are each independently selected from H, F, $CF_3$, CN, $NO_2$, methoxy, Cl, Br, OH and alkyl;

or $R^7$ and $R^8$, $R^8$ and $R^9$, $R^9$ and $R^{10}$, $R^{10}$ and $R^{11}$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S. (e.g. 2-furanone, 1,3-dioxolane, cyclopentane, cyclopentene, 1,4-dioxane, cyclohexane, cyclohexene, cyclohexanone, pyrrole, imidazole, pyrazole, pyrrolidine, imidazoline, tetrahydrofurane, furane, oxazole, isoxazole, thiolane, isoxazole, thiophene, thiazole, isothiazole, pyridine, pyrimidine, 1,4-piperazine, piperidine, morpholine, 1,4-dithiane). Thus, the compound of formula (I) may be a compound of any one of formulae (IF) to (IL):

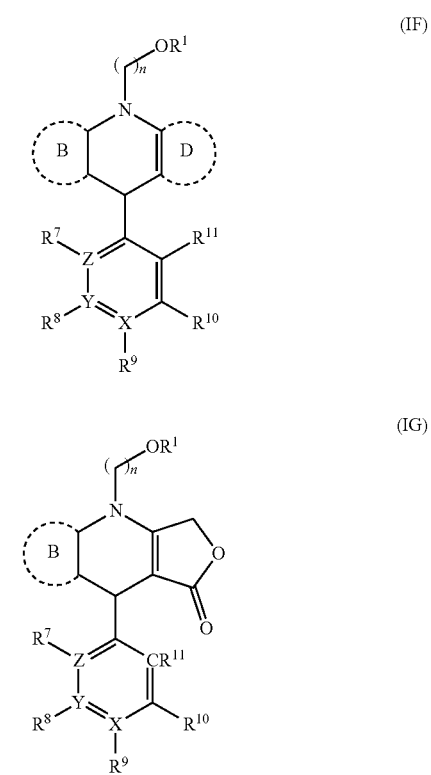

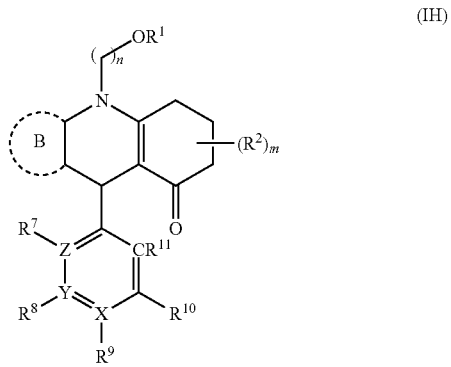

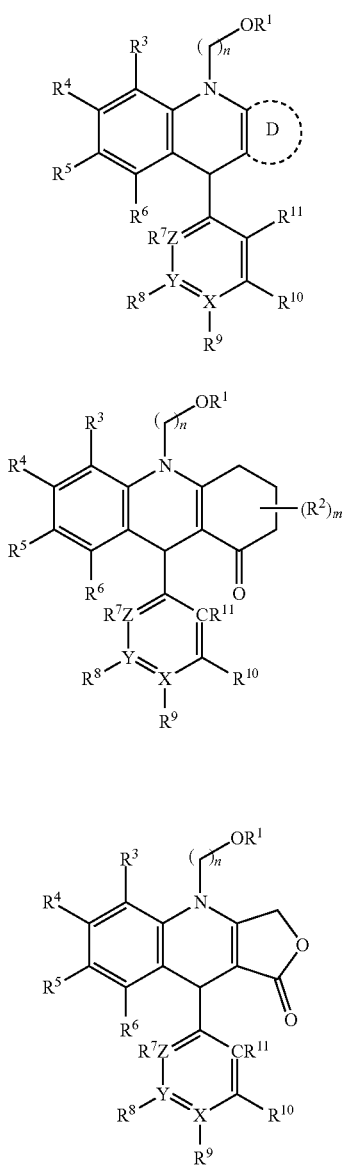

(IJ)

(IK)

(IL)

wherein the Ring B, Ring D and Ring E are each independently any of the groups as defined above for a compound of formula (I).

In certain embodiments of any one of formulae (I)-(IL), n is an integer of 6 or less, such as 5, 4, 3, 2 or 1. In certain cases of any one of formulae (I)-(IL), n is 2.

In some cases of a GBP1 inhibitor of any of formulas (I)-(IB), the B ring is of the formula (B2) or (B3):

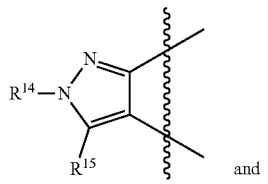

(B2) and

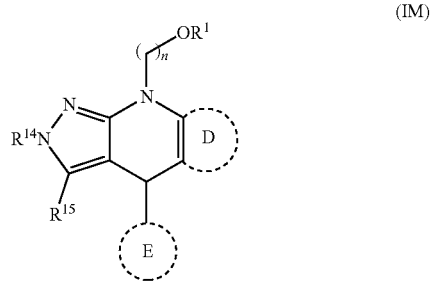

(B3)

wherein:

$R^{14}$, $R^{15}$, $R^{16}$ and $R^{17}$ are each independently selected from H, alkyl, aryl, substituted aryl. Thus, the compound of formula (I) may be a compound of any one of formulae (IM) to (IR):

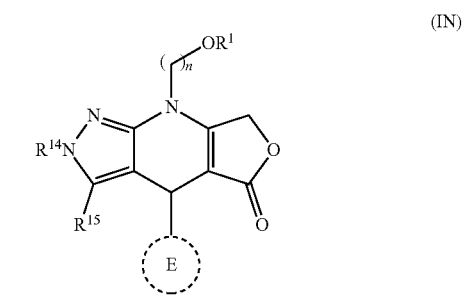

(IM)

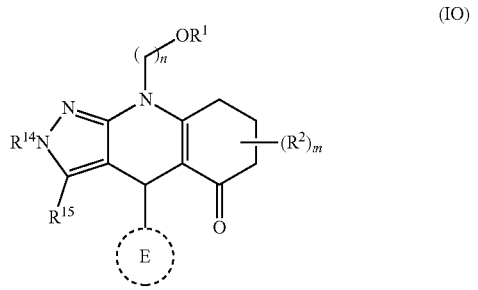

(IN)

(IO)

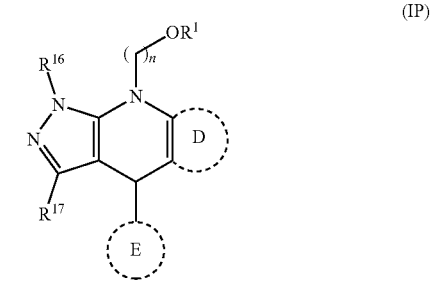

(IP)

-continued (IQ)

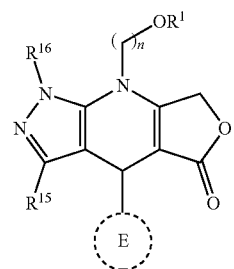

(IR)

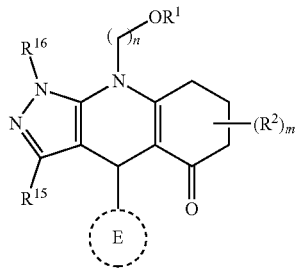

wherein the Ring D and Ring E are each independently any of the groups as defined above for a compound of formula (I).

In some cases, the compound of formula (I) may be a compound of any one of formulae (IS) to (IV):

(IS)

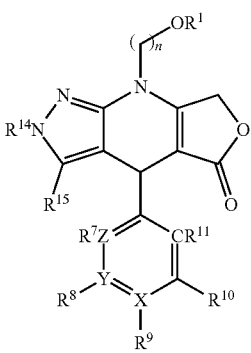

(IT)

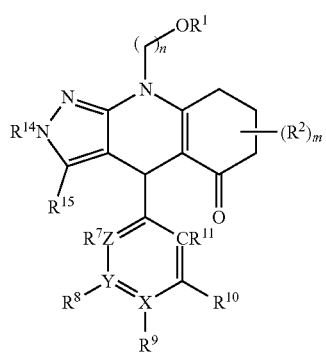

(IU)

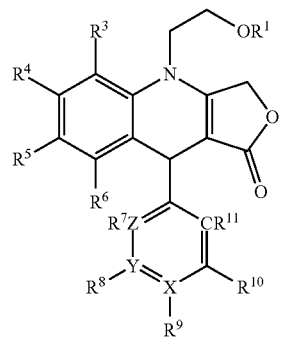

(IV)

In certain embodiments of any one of formulae (IM)-(IV), n is an integer of 6 or less, such as 5, 4, 3, 2 or 1. In certain cases of any one of formulae (IM)-(IV), n is 2.

In some embodiments, the GBP1 inhibitor of formula (I), is of the formula (II):

(II)

wherein:
$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

$R^3$, $R^4$, $R^5$ and $R^6$ are independently selected from H, OH, methoxy, alkyl, halogen, $CF_3$, CN and $NO_2$;

or any of $R^4$ and $R^5$, $R^3$ and $R^4$, $R^5$ and $R^6$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S (e.g. 2-furanone, 1,3-dioxolane, cyclopentane, cyclopentene, 1,4-dioxane, cyclohexane, cyclohexene, cyclohexanone);

X, Y and Z are each independently selected from C or N;
$R^{10}$ is selected from F, $CF_3$, CN, $NO_2$, OH and alkyl;
$R^7$, $R^8$, $R^9$ and $R^{11}$ are each independently selected from H, F, $CF_3$, CN, $NO_2$, methoxy, Cl, Br, OH and alkyl;
or $R^7$ and $R^8$, $R^8$ and $R^9$, $R^9$ and $R^{10}$, $R^{10}$ and $R^{11}$ together with the carbons to which they are attached form a $C_{5-6}$ carbocycle, or $C_{5-6}$ heterocycle containing up to two atoms selected from N, O or S a substituted $C_{5-6}$ carbocycle, or a substituted $C_{5-6}$ membered heterocycle containing up to two atoms selected from N, O or S,
or a pro-drug, a pharmaceutically acceptable salt or a solvate thereof.

In some embodiments of formula (II), at least one of $R^7$-$R^{11}$ is F. In some cases of formula (II), at least one of $R^7$-$R^{11}$ is $CF_3$. In other cases, of formula (II), at least one of $R^7$-$R^{11}$ is $NO_2$. In some embodiments of formula (II), at least one of $R^7$-$R^{11}$ is CN. In certain cases of formula (II), at least one of $R^7$-$R^{11}$ is a group other than H. In certain cases of formula (II), at least two of $R^7$-$R^{11}$ are groups other than hydrogen. In certain instances, $R^8$, $R^9$ and $R^{10}$ are groups other than hydrogen and $R^7$ and $R^{11}$ are both hydrogen.

In certain instances of the GBP1 inhibitor of formula (II), all of X, Y and Z are carbon atoms. In other cases of the GBP1 inhibitor of formula (II), at least one of X, Y or Z is a nitrogen atom. In other cases of the GBP1 inhibitor of formula (II), X is a nitrogen atom and Y and Z are both carbon atoms. In other cases of the GBP1 inhibitor of formula (II), Y is a nitrogen atom and X and Z are both carbon atoms. In other cases of the GBP1 inhibitor of formula (II), Z is a nitrogen atom and X and Y are both carbon atoms.

In certain cases, the GBP1 inhibitor of formula (I), is of the formula (III):

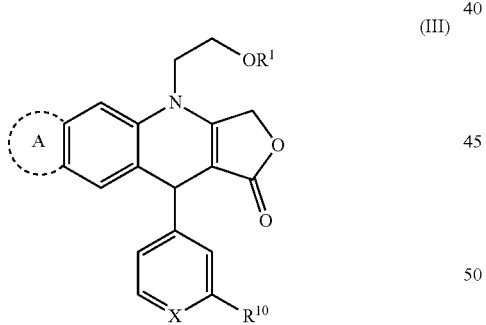
(III)

wherein:
Ring A is selected from a $C_{5-6}$ carbocycle, a $C_{5-6}$ heterocycle containing up to two atoms selected from N, O or S, a substituted $C_{5-6}$ carbocycle, and a substituted $C_{5-6}$ heterocycle containing up to two atoms selected from N, O or S;
X is C or N;
$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
$R^{10}$ is selected from F, $CF_3$, CN, $NO_2$, OH, alkyl and methoxy,
or a pro-drug, a pharmaceutically acceptable salt or a solvate thereof.

In certain instances of the GBP1 inhibitor of formula (III), the A Ring is selected from 1,3-dioxolane, cyclopentane, cyclopentene, 1,4-dioxane, cyclohexane, cyclohexene. In some cases, the A ring is dioxolane. In some cases, the A ring is cyclopentane. In some cases, the A ring is cyclopentane. In some cases, the A ring is 1,4-dioxane. In some cases, the A ring is cyclohexane. In some other cases, the A ring is cyclohexene.

In certain instances of the GBP1 inhibitor of formula (III), $R^{10}$ is F. In other cases of formula (III), $R^{10}$ is $CF_3$. In other cases of formula (III), $R^{10}$ is CN. In yet other cases of formula (III), $R^{10}$ is $NO_2$. In some cases $R^{10}$ is OH. In some cases, $R^{10}$ is alkyl. In some cases, $R^{10}$ is methoxy.

In certain instances of the GBP1 inhibitor of formula (III), X is a carbon atom. In other cases of the GBP1 inhibitor of formula (III), X is a nitrogen atom. In other cases of the GBP1 inhibitor of formula (III), X is an oxygen atom. In other cases of the GBP1 inhibitor of formula (III), X is a sulfur atom.

In some embodiments the GBP1 inhibitor of formula (III) is a structure selected from any of compounds (1)-(11):

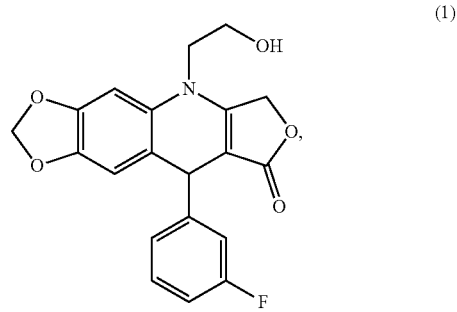
(1)

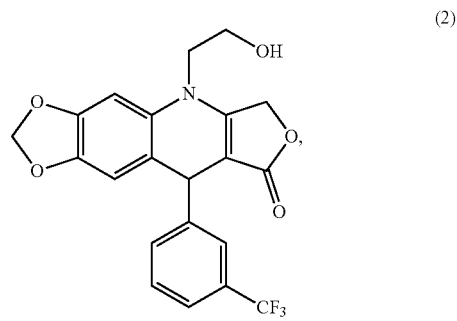
(2)

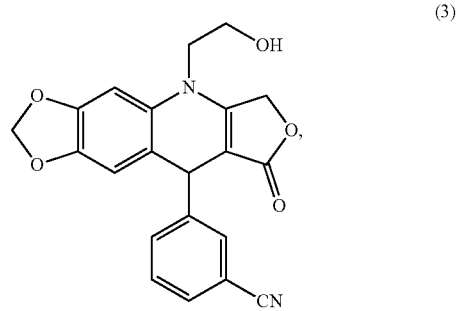
(3)

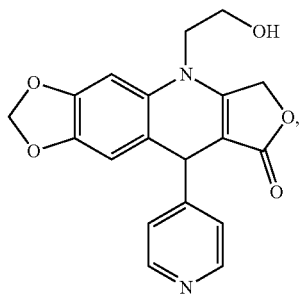
(4)
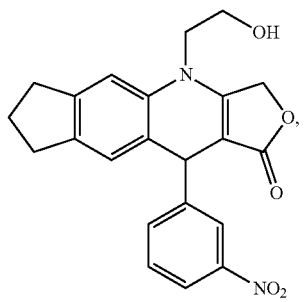
(5)
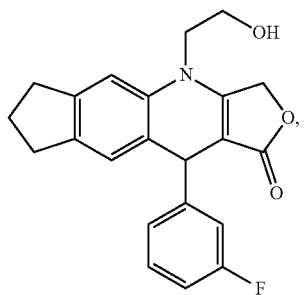
(6)
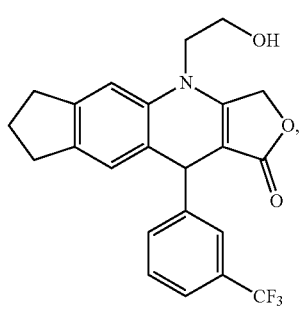
(7)
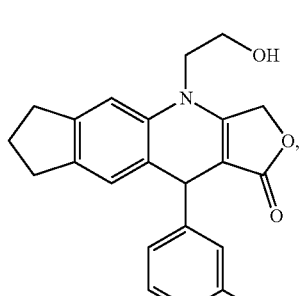
(8)
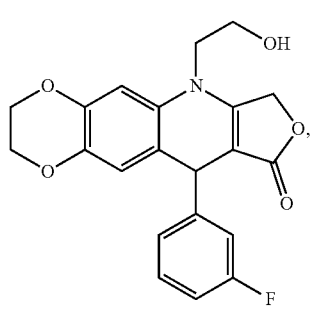
(9)
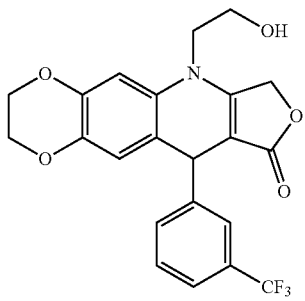
(10)
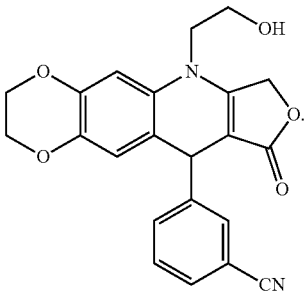
(11)
In some embodiments the GBP1 inhibitor of formula (II) is a structure selected from any of compounds (12)-(16):
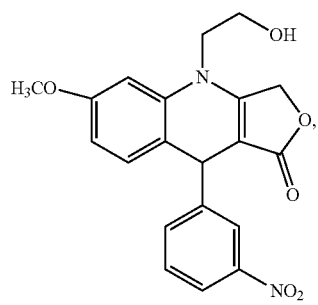
(12)
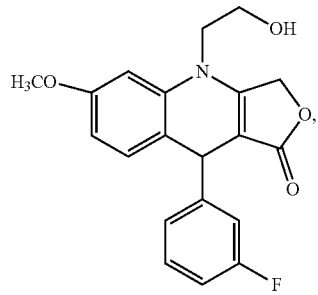
(13)

-continued

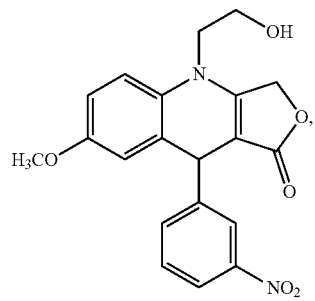

(14)

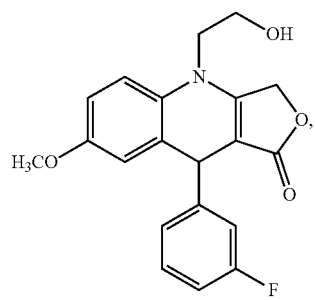

(15)

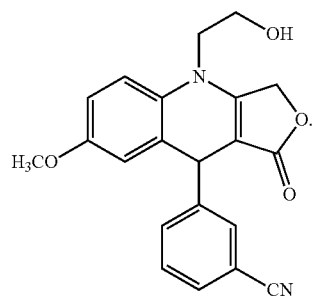

(16)

In some embodiments, the GBP1 inhibitor of formula (I), is of the formula (IV):

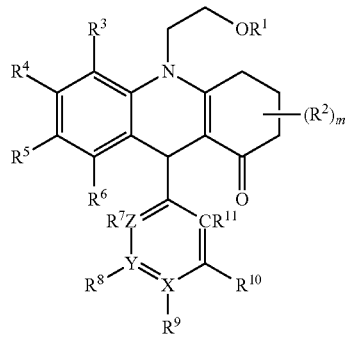

(IV)

wherein:

R$^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

R$^2$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

R$^3$, R$^4$, R$^5$ and R$^6$ are independently selected from H, OH, methoxy, alkyl, halogen, CF$_3$, CN and NO$_2$;

or any of R$^4$ and R$^5$, R$^3$ and R$^4$, R$^5$ and R$^6$ together with the carbons to which they are attached form a C$_{5-6}$ carbocycle, a C$_{5-6}$ heterocycle containing up to two atoms selected from N, O or S, a substituted C$_{5-6}$ carbocycle, or a substituted C$_{5-6}$ membered heterocycle containing up to two atoms selected from N, O or S (e.g. 2-furanone, 1,3-dioxolane, cyclopentane, cyclopentene, 1,4-dioxane, cyclohexane, cyclohexene, cyclohexanone);

X, Y and Z are each independently selected from C or N;

R$^7$, R$^8$, R$^9$, R$^{10}$ and R$^{11}$ are each independently selected from H, F, CF$_3$, CN, NO$_2$, methoxy, Cl, Br, OH and alkyl;

or R$^7$ and R$^8$, R$^8$ and R$^9$, R$^9$ and R$^{10}$, R$^{10}$ and R$^{11}$ together with the carbons to which they are attached form a C$_{5-6}$ carbocycle, or C$_{5-6}$ heterocycle containing up to two atoms selected from N, O or S, a substituted C$_{5-6}$ carbocycle, or a substituted C$_{5-6}$ membered heterocycle containing up to two atoms selected from N, O or S; and m is an integer from 0 to 6, or a pro-drug, a pharmaceutically acceptable salt or a solvate thereof.

In some embodiments of formula (IV), at least one of R$^7$-R$^{11}$ is F. In some embodiments of formula (IV), at least one of R$^7$-R$^{11}$ is methoxy. In some cases of formula (IV), at least one of R$^7$-R$^{11}$ is CF$_3$. In other cases, of formula (IV), at least one of R$^7$-R$^{11}$ is NO$_2$. In some embodiments of formula (IV), at least one of R$^7$-R$^{11}$ is CN. In certain cases of formula (IV), at least one of R$^7$-R$^{11}$ is a group other than hydrogen. In certain cases of formula (IV), all of R$^7$-R$^{11}$ are hydrogen. In certain cases of formula (IV), at least two of R$^7$-R$^{11}$ are groups other than hydrogen. In certain instances of formula (IV), R$^8$, R$^9$ and R$^{10}$ are groups other than hydrogen and R$^7$ and R$^{11}$ are both hydrogen. In certain instances of formula (IV), R$^8$, R$^9$ and R$^{10}$ are methoxy groups and R$^7$ and R$^{11}$ are both hydrogen.

In certain instances of the GBP1 inhibitor of formula (IV), all of X, Y and Z are carbon atoms. In other cases of the GBP1 inhibitor of formula (IV), at least one of X, Y or Z is a nitrogen atom. In other cases of the GBP1 inhibitor of formula (IV), X is a nitrogen atom and Y and Z are both carbon atoms. In other cases of the GBP1 inhibitor of formula (IV), Y is a nitrogen atom and X and Z are both carbon atoms. In other cases of the GBP1 inhibitor of formula (IV), Z is a nitrogen atom and X and Y are both carbon atoms.

In certain cases of formula (IV), m is 0. In some cases of formula (IV), m is from 1-6 and each R$^2$ is independently selected from an alkyl, a substituted alkyl or a combination thereof. In some embodiments of formula (IV), m is 2 and each R$^2$ is a C$_{1-6}$ alkyl. In certain cases of formula (IV), m is 2 and each R$^2$ is methyl. In other case m is 1 and R$^2$ is methyl. In other cases, m is 2 and R$^2$ is ethyl. In other case m is 1 and R$^2$ is ethyl. In other cases, m is 2 and R$^2$ is ethyl. In other case m is 1 and R$^2$ is ethyl. In other cases, m is 2 and R$^2$ is propyl. In other case m is 1 and R$^2$ is propyl. In other cases, m is 2 and R$^2$ is butyl. In other case m is 1 and R$^2$ is butyl. In other cases, m is 2 and R$^2$ is pentyl. In other case m is 1 and R$^2$ is pentyl. In yet other cases, m is 2 and R$^2$ is hexyl. In other case m is 1 and R$^2$ is hexyl.

In some embodiments the GBP inhibitor of the formula (IV), is of the formula (V):

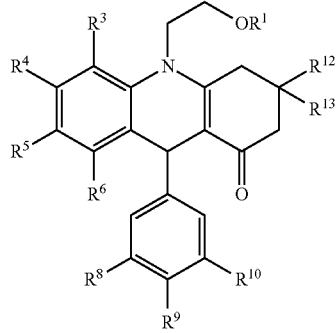

wherein:
- R$^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
- R$^3$, R$^4$, R$^5$ and R$^6$ are independently selected from H, OH, methoxy, alkyl, halogen, CF$_3$, CN and NO$_2$;
- or any of R$^4$ and R$^5$, R$^3$ and R$^4$, R$^5$ and R$^6$ together with the carbons to which they are attached form a C$_{5-6}$ carbocycle, a C$_{5-6}$ heterocycle containing up to two atoms selected from N, O or S, a substituted C$_{5-6}$ carbocycle, or a substituted C$_{5-6}$ membered heterocycle containing up to two atoms selected from N, O or S (e.g. 2-furanone, 1,3-dioxolane, cyclopentane, cyclopentene, 1,4-dioxane, cyclohexane, cyclohexene, cyclohexanone);
- R$^{12}$ and R$^{13}$ are each independently selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl, F, CF$_3$, CN, NO$_2$ and methoxy;
- R$^8$, R$^9$ and R$^{10}$ are each independently selected from H, F, CF$_3$, CN, NO$_2$, methoxy, Cl, Br, OH and alkyl;
- or any of R$^8$ and R$^9$ or R$^9$ and R$^{10}$ together with the carbons to which they are attached form a C$_{5-6}$ carbocycle, a C$_{5-6}$ heterocycle containing up to two atoms selected from N, O or S, a substituted C$_{5-6}$ carbocycle, or a substituted C$_{5-6}$ membered heterocycle containing up to two atoms selected from N, O or S,
- or a pro-drug, a pharmaceutically acceptable salt or a solvate thereof.

In some cases of formulae (IV) or (V), R$^4$ is methoxy and each of R$^3$, R$^5$ and R$^6$ are H. In other cases of formulae (IV) or (V), each of R$^3$, R$^4$ and R$^6$ are H and R$^5$ is methoxy. In other cases of formulae (IV) or (V), R$^4$ and R$^5$ together with the carbons to which they are attached form a group selected from 1,3-dioxolane, cyclopentane, cyclopentene, 1,4-dioxane, cyclohexane, cyclohexene; and each of R$^3$ and R$^6$ are H. In yet other cases of formulae (IV) or (V), R$^4$ and R$^5$ together with the carbons to which they are attached form 1,3-dioxolane; and each of R$^3$ and R$^6$ are H. In yet other cases of formulae (IV) or (V), R$^4$ and R$^5$ together with the carbons to which they are attached form cyclopentane; and each of R$^3$ and R$^6$ are H.

In certain embodiments of formula (V), R$^{10}$ is F and R$^8$ and R$^9$ are both hydrogen. In other cases of formula (V), R$^8$, R$^9$ and R$^{10}$ are each hydrogen. In some other instances, R$^8$, R$^9$ and R$^{10}$ are each methoxy.

In certain cases of formula (V), R$^{12}$ and R$^{13}$ are both hydrogen. In some cases of formula (V), R$^{12}$ and R$^{13}$ are both independently selected from an alkyl, a substituted alkyl or a combination thereof. In some embodiments of formula (V), R$^{12}$ and R$^{13}$ are both C$_{1-6}$ alkyl. In some embodiments of formula (V), R$^{12}$ and R$^{13}$ are both methyl.

In some embodiments the GBP1 inhibitor of formula (V) is a structure selected from any of compounds (17)-(23):

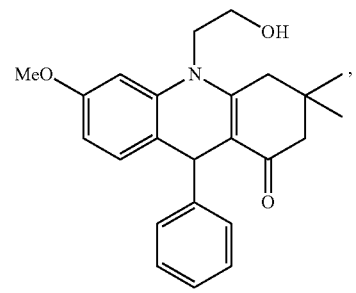
(17)

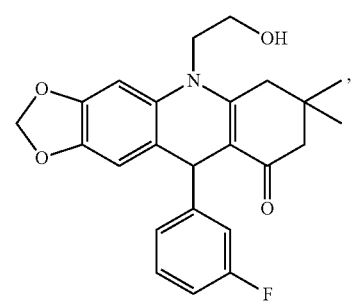
(18)

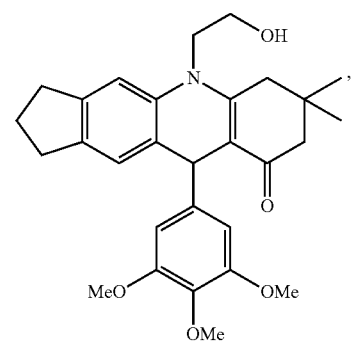
(19)

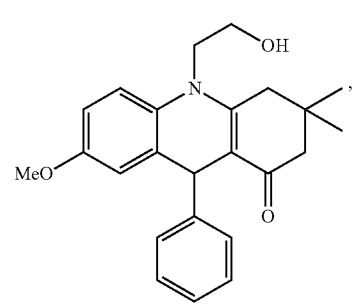
(20)

-continued

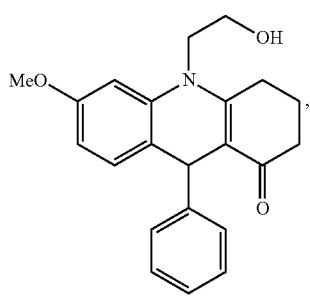

(21)

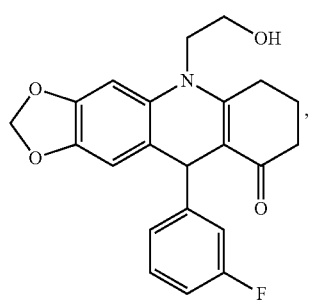

(22)

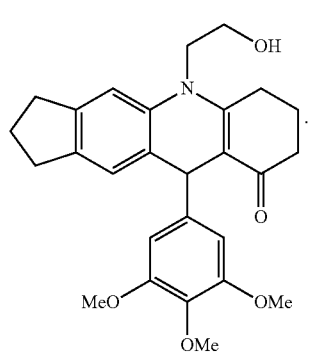

(23)

In some embodiments, the GBP1 inhibitor of formula (I), is of the formula (VI):

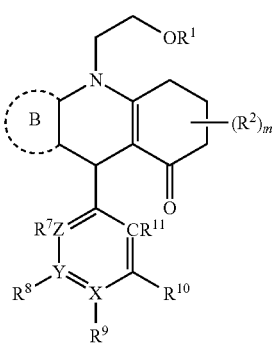

(VI)

wherein:
R¹ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
R² is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

X, Y and Z are each independently selected from C or N;
R⁷, R⁸, R⁹, R¹⁰ and R¹¹ are each independently selected from H, F, CF₃, CN, NO₂, methoxy, Cl, Br, OH and alkyl;
or any of R⁷ and R⁸, R⁸ and R⁹, R⁹ and R¹⁰, R¹⁰ and R¹¹ together with the carbons to which they are attached form a C₅₋₆ carbocycle, a C₅₋₆ heterocycle containing up to two atoms selected from N, O or S, a substituted C₅₋₆ carbocycle, or a substituted C₅₋₆ membered heterocycle containing up to two atoms selected from N, O or S;

Ring B is selected from the formulae (B2) and (B3):

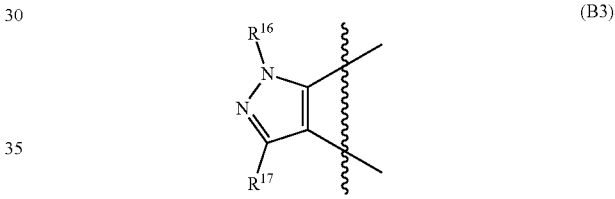

(B2)

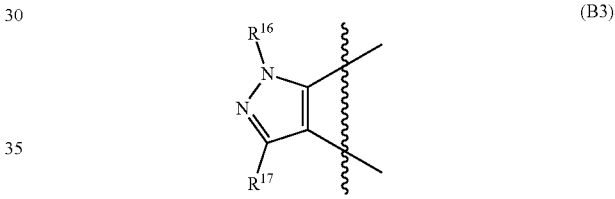

(B3)

wherein R¹⁴, R¹⁵, R¹⁶ and R¹⁷ are each independently selected from H, alkyl, aryl, substituted aryl;
and
m is an integer from 0 to 6,
or a pro-drug, a pharmaceutically acceptable salt or a solvate thereof.

In certain embodiments of formula (VI), Ring B is of the formula (B2). In other embodiments of formula (VI), Ring B is of the formula (B3). Accordingly, in certain cases the compound of formula (VI) is of the formulae (VIA) or (VIB):

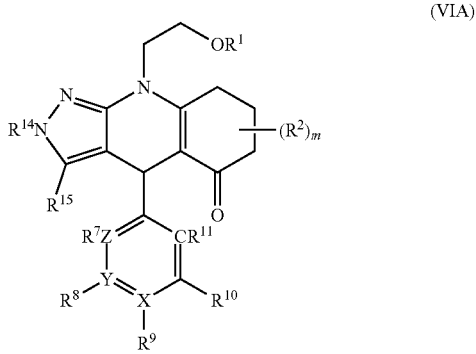

(VIA)

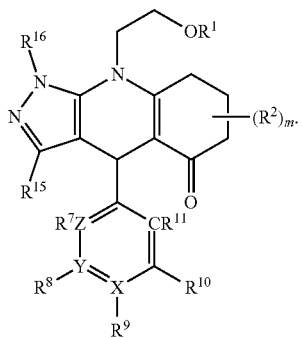

(VIB)

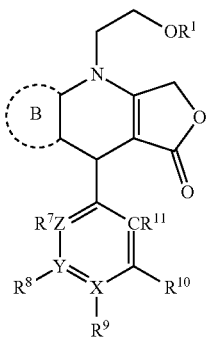

(VII)

In certain embodiments the compound of formula (VI) is of the formulae (VIC) or (VID):

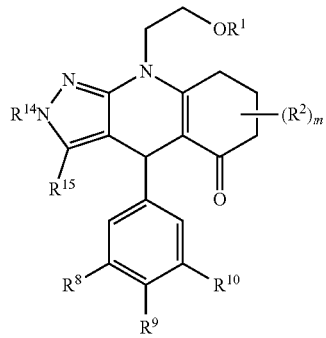

(VIC)

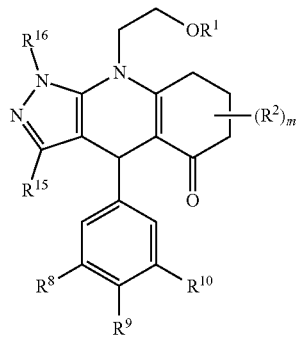

(VID)

wherein each of the groups $R^1$, $R^2$, $R^8$, $R^9$, $R^{10}$, $R^{14}$, $R^{15}$ and $R^{16}$ are as defined herein.

In some embodiments, the GBP1 inhibitor of formula (I), is of the formula (VII):

wherein:

$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

X, Y and Z are each independently selected from C or N;

$R^7$, $R^8$, $R^9$, $R^{10}$ and $R^{11}$ are each independently selected from H, F, $CF_3$, CN, $NO_2$, methoxy, Cl, Br, OH and alkyl;

or any of $R^7$ and $R^8$, $R^8$ and $R^9$, $R^9$ and $R^{10}$, $R^{10}$ and $R^{11}$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S; and Ring B is selected from the formulae (B2) and (B3):

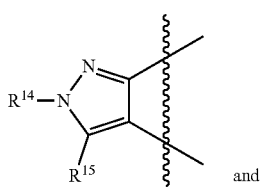

(B2)

and

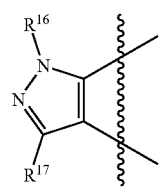

(B3)

wherein $R^{14}$, $R^{15}$, $R^{16}$ and $R^{17}$ are each independently selected from H, alkyl, aryl, and substituted aryl;

or a pro-drug, a pharmaceutically acceptable salt or a solvate thereof.

In certain embodiments of formula (VII), Ring B is of the formula (B2). In other embodiments of formula (VII), Ring B is of the formula (B3). Accordingly, in certain cases the compound of formula (VII) is of the formulae (VIIA) or (VIIB):

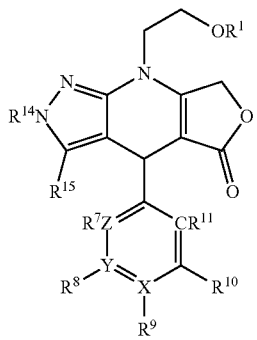

(VIIA)

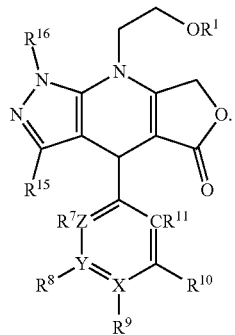

(VIIB)

In certain embodiments the compound of formula (VII) is of the formulae (VIIC) or (VIID):

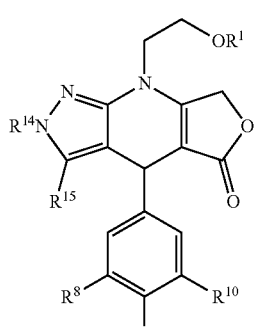

(VIIC)

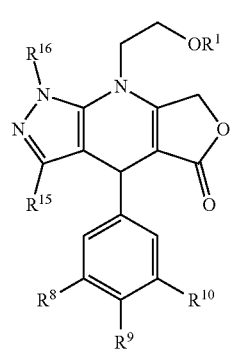

(VIID)

wherein each of the groups $R^1$, $R^8$, $R^9$, $R^{10}$, $R^{14}$, $R^{15}$ and $R^{16}$ are as defined herein.

In certain embodiments, the compound is described by the structure of one of the compounds of 1-23. It is understood that any of the compounds 1-23 may be present in a salt form. In some cases, the salt form of the compound is a pharmaceutically acceptable salt.

Aspects of the present disclosure include GBP1 inhibitor compounds (e.g., as described herein), salts thereof (e.g., pharmaceutically acceptable salts), and/or solvate, hydrate and/or prodrug forms thereof. It is understood that, in any compound described herein having one or more chiral centers, if an absolute stereochemistry is not expressly indicated, then each center may independently be of R-configuration or S-configuration or a mixture thereof. More specifically, where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure. It will be appreciated that all permutations of salts, solvates, hydrates, prodrugs and stereoisomers are meant to be encompassed by the present disclosure.

In some embodiments, the subject GBP1 inhibitor compounds, or a prodrug form thereof, are provided in the form of pharmaceutically acceptable salts. Compounds containing an amine or nitrogen containing heteroaryl group may be basic in nature and accordingly may react with any number of inorganic and organic acids to form pharmaceutically acceptable acid addition salts. Acids commonly employed to form such salts include inorganic acids such as hydrochloric, hydrobromic, hydriodic, sulfuric and phosphoric acid, as well as organic acids such as para-toluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephathalate, sulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene-1-sulfonate, naphthalene-2- sulfonate, mandelate, hippurate, gluconate, lactobionate, and the like salts. In certain specific embodiments, pharmaceutically acceptable acid addition salts include those formed with mineral acids such as hydrochloric acid and hydrobromic acid, and those formed with organic acids such as fumaric acid and maleic acid.

In some embodiments, the subject compounds are provided in a prodrug form. "Prodrug" refers to a derivative of an active agent that requires a transformation within the body to release the active agent. In certain embodiments, the transformation is an enzymatic transformation. Prodrugs are frequently, although not necessarily, pharmacologically inactive until converted to the active agent. "Promoiety" refers to a form of protecting group that, when used to mask a functional group within an active agent, converts the active agent into a prodrug. In some cases, the promoiety will be attached to the drug via bond(s) that are cleaved by enzymatic or non-enzymatic means in vivo. Any convenient prodrug forms of the subject compounds can be prepared, e.g., according to the strategies and methods described by Rautio et al. ("Prodrugs: design and clinical applications", Nature Reviews Drug Discovery 7, 255-270 (February 2008)). In some cases, the promoiety is attached to a hydroxy group of the subject compounds.

In some embodiments, the subject compounds, prodrugs, stereoisomers or salts thereof are provided in the form of a solvate (e.g., a hydrate). The term "solvate" as used herein refers to a complex or aggregate formed by one or more molecules of a solute, e.g. a prodrug or a pharmaceutically-acceptable salt thereof, and one or more molecules of a solvent. Such solvates are typically crystalline solids having a substantially fixed molar ratio of solute and solvent. Representative solvents include by way of example, water, methanol, ethanol, isopropanol, acetic acid, and the like. When the solvent is water, the solvate formed is a hydrate.

In some embodiments, the subject compounds are provided by oral dosing and absorbed into the bloodstream. In some embodiments, the oral bioavailability of the subject compounds is 30% or more. Modifications may be made to the subject compounds or their formulations using any convenient methods to increase absorption across the gut lumen or their bioavailability.

In some embodiments, the subject compounds are metabolically stable (e.g., remain substantially intact in vivo during the half-life of the compound). In certain embodiments, the compounds have a half-life (e.g., an in vivo half-life) of 5 minutes or more, such as 10 minutes or more, 12 minutes or more, 15 minutes or more, 20 minutes or more, 30 minutes or more, 60 minutes or more, 2 hours or more, 6 hours or more, 12 hours or more, 24 hours or more, or even more.

Methods of Inhibiting GBP1

As summarized above, aspects of the present disclosure include GBP1 inhibiting compounds, and methods of inhibition using the same. Guanylate-Binding Protein 1 (GBP1) is a large-GTPase that plays a major role in cancer cells stressed in a setting of hypoxia and low nutrient supply. GBP1 is induced by interferon IFNγ and involved in the regulation of proliferation and endosome fate in endothelial cells and macrophages. Cytokine- and hypoxiainduced overexpression of GBP1 in cancer leads to increased production of Class III β-tubulin (βTUB3) and recruitment of kinases such as PIM into the cytoskeleton, which supports tumor survival and growth. As such, aspects of the subject methods include inhibiting GBP1: pro-survival kinase (e.g. serine/threonine-protein kinase pim-1 (PIM1)) interactions. The inventors have previously discovered that inhibiting the activity of GBP1 abrogated GBP1:PIM1 interaction and restored taxane sensitivity (e.g. paclitaxel sensitivity) to a taxane-resistant ovarian cancer cell line without any observed gross morbidity (Andreoli, M. et al. *Journal of Medicinal Chemistry* 2014, 57(19), 7916-7932).

By inhibiting a GBP1 it is meant that the activity of the enzyme is decreased by 10% or more, such as 20% or more, 30% or more, 40% or more, 50% or more, 60% or more, 70% or more, 80% or more, 90% or more, 95% or more (e.g., relative to a control in any convenient in vitro inhibition assay). In some cases, inhibiting a GBP1 means decreasing the activity of the enzyme by a factor of 2 or more, such as 3 or more, 5 or more, 10 or more, 100 or more, or 1000 or more, relative to its normal activity (e.g., relative to a control as measured by any convenient assay).

In some cases, the method is a method of inhibiting GBP1 in a sample. The term "sample" as used herein relates to a material or mixture of materials, typically, although not necessarily, in fluid form, containing one or more components of interest.

In some embodiments, there is provided a method of inhibiting GBP1, the method comprising contacting a cellular sample with a GBP1 inhibitor to inhibit GBP: pro-survival kinase (e.g. serine/threonine-protein kinase pim-1 (PIM1)) interactions.

In certain embodiments the GBP1 inhibitor is an inhibitor as defined herein. In some embodiments, the GBP1 inhibitor is an inhibitor according to any one of formulas I or VII. In some cases, the GBP1 inhibitor is any one of compounds 1-23.

In some embodiments the GBP1 inhibitor is an allosteric modulator of GBP1. The term "allosteric modulator" refers to a compound which interacts with an allosteric site of a receptor to activate the primary binding site. The subject compounds are allosteric modulators of GBP1. For example, an allosteric modulator may directly or indirectly augment the response produced by the subject compound at the orthosteric site of GBP1 in an animal, in particular, a human. In some embodiments, subject inhibitors restore treatment sensitivity in a cancer. In certain cases, the cancer is ovarian cancer or head and neck cancer.

In some embodiments, the subject compounds have a GBP1 inhibition profile that reflects activity against additional enzymes. In some embodiments, the subject compounds specifically inhibit GBP1 without undesired inhibition of one or more other enzymes.

In some embodiments, the subject compounds inhibit GBP1, as determined by an inhibition assay, e.g., by an assay that determines the level of activity of the enzyme either in a cell-free system or in a cell after treatment with a subject compound, relative to a control, by measuring the $IC_{50}$ or $EC_{50}$ value, respectively. In certain embodiments, the subject compounds have an $IC_{50}$ value (or $EC_{50}$ value) of 10 µM or less, such as 3 µM or less, 1 µM or less, 500 nM or less, 300 nM or less, 200 nM or less, 100 nM or less, 50 nM or less, 30 nM or less, 10 nM or less, 5 nM or less, 3 nM or less, 1 nM or less, or even lower.

As summarized above, aspects of the disclosure include methods of inhibiting GBP1. A subject compound (e.g., as described herein) may inhibit at activity of GBP1 in the range of 10% to 100N, e.g., by 10% or more, 20% or more, 30% or more, 40% or more, 50% or more, 60% or more, 70% or more, 80% or more, or 90% or more. In certain assays, a subject compound may inhibit its target with an $IC_{50}$ of $1\times10^{-6}$ M or less (e.g., $1\times10^{-6}$ M or less, $1\times10^{-7}$ M or less, $1\times10^{-8}$ M or less, $1\times10^{-9}$ M or less, $1\times10^{-10}$ M or less, or $1\times10^{-11}$ M or less).

The protocols that may be employed in determining GBP1 activity are numerous, and include but are not limited to cell-free assays, e.g., binding assays; assays using purified enzymes, cellular assays in which a cellular phenotype is measured, e.g., gene expression assays; and in vivo assays that involve a particular animal (which, in certain embodiments may be an animal model for a condition related to the target pathogen).

In some embodiments, the subject method is an in vitro method that includes contacting a sample with a subject compound that specifically inhibits GBP1. In certain embodiments, the sample is suspected of containing GBP1 and the subject method further comprises evaluating whether the compound inhibits GBP1.

In certain embodiments, the subject compound is a modified compound that includes a label, e.g., a fluorescent label, and the subject method further includes detecting the label, if present, in the sample, e.g., using optical detection.

In certain embodiments, the compound is modified with a support or with affinity groups that bind to a support (e.g. biotin), such that any sample that does not bind to the compound may be removed (e.g., by washing). The specifically bound GBP1, if present, may then be detected using any convenient means, such as, using the binding of a labeled target specific probe, or using a fluorescent protein reactive reagent.

In another embodiment of the subject method, the sample is known to contain GBP1.

In some embodiments, the method is a method of reducing cancer cell proliferation, where the method includes contacting the cell with an effective amount of a subject GBP1 inhibitor compound (e.g., as described herein) to reduce cancer cell proliferation. The method can be performed in combination with a chemotherapeutic agent (e.g., as described herein). The cancer cells can be in vitro or in vivo. In certain instances, the method includes contacting the cell with a GBP1 inhibitor compound (e.g., as described herein) and contacting the cell with a chemotherapeutic agent. In certain instances, the method includes contacting the cell with a GBP1 inhibitor compound in combination with radiation therapy. In certain instances, the combination sensitizes the cancer to the chemotherapeutic agent and the radiation therapy. Any convenient cancer cells can be targeted. In certain instances, the cancer cells are resistant to radiation therapy. In certain instances the cancer cells are resistant to chemotherapy.

Methods of Treatment

Aspects of the present disclosure include methods for inhibiting GBP1 by treatment with a subject compound to inhibit GBP1: pro-survival kinase (e.g. serine/threonine-protein kinase pim-1 (PIM1) interactions. The inventors have established that the GBP1 protein has significant effect in the tumor microenvironment modulation (e.g. see FIG. 1, panels A-F), and can be a potential target for various solid tumor treatments. The inventors have also discovered that GBP1 expression is associated with the modulation of specific stemness markers and have demonstrated that GBP1 overexpression leads to radiation resistance (e.g. see FIG. 2, panels A-C). The inventors have further discovered that inhibition of GBP1 (e.g. by a compound as described herein) can have significant impact on overcoming radiation and chemotherapy resistance in ovarian cancer (e.g. see FIG. 5, panels A-E) as well as head and neck cancer (e.g. see FIG. 6, panels A-E). Further, in vivo results described and demonstrated herein indicate that the subject compounds possess favorable pharmacokinetics and safety profiles (e.g. see FIG. 7, panels A-B) and can cause significant tumor regression in ovarian and head and neck cancer mouse models with no liver toxicity (e.g. see FIG. 8, panels A-D and FIG. 9 panels A-B).

The results described and demonstrated herein indicate that GBP1 inhibition according to the subject methods can re-sensitize refractory tumors to chemotherapy and radiation treatment in vivo, and thus find use in the treatment of a variety of solid tumors, e.g., as a target for various cancers. As such, the subject methods provide for selective inhibition of GBP1 activity to restore and increase treatment sensitivity in radiation and chemotherapy resistant cancers.

A "chemotherapy resistant cancer" or "chemoresistant cancer" refers to cancer cells that intrinsically or by acquired means are resistant to chemotherapeutic agents. As a non-limiting example, such cells may be resistant to the spectrum of agents including: paclitaxel, docetaxel, cabazitaxel, doxorubicin, daunorubicin, mitoxantrone, actinomycin D, plicamycin, vincristine, vinblastine, colchicine, etoposide, and teniposide. In certain cases, cancer cells are resistant to a taxane agent e.g. paclitaxel, docetaxel or cabazitaxel. In particular cases, such cells are resistant to paclitaxel. By resistant, it is intended that the $LD_{50}$ of the drug with respect to the cell is increased at least about 2-fold, at least about 5-fold, at least about 10-fold, at least about 20-fold, or more relative to a non-resistant cell from the same class of cancer.

A "radiation resistant cancer" or "radioresistant cancer" refers to cancer cells that are resistant to radiation treatment. By radiation resistant, it is intended that the cancer cells are more robust and less responsive toward radiation therapy than non-resistant cancer cells. In some cases, GBP1 is overexpressed in the cancer cells. In some cases, the radiation resistant cancer cells have enhanced metastatic and stem cell properties.

A resistant cancer, or a refractory cancer, can be unresponsive to first and sometimes second line chemotherapy drugs, biological agents and/or radiation therapy. Often, refractory cancer can be a stable disease or a progressive disease.

By sensitizing the cancer to chemotherapy and radiation therapy in a subject by administration of a subject GBP1 inhibitor is meant an increase in the chemotherapy or radiation therapy response in a subject as compared to a control subject (e.g., a subject who is not administered a subject compound). In some cases, the subject is human and the subject compounds and methods provide for inhibition of GBP1. In some cases, the response includes regression in the size of a solid tumor. In some instances, the solid tumor is an ovarian cancer tumor or a head and neck cancer tumor.

Aspects of the methods include administering to a subject an effective amount of an GBP1 inhibitor to inhibit GBP1: pro-survival kinase (e.g. serine/threonine-protein kinase pim-1 (PIM1)) interactions and treat the subject for cancer. Any convenient GBP1 inhibitors can be used in the subject methods of treating cancer. In certain cases, the GBP inhibitor compound is a compound as described herein. In certain cases the cancer is a solid cancer. In certain embodiments, the cancer is selected from ovarian cancer (OC), colorectal cancer, prostate cancer, head and neck cancer (HNC), lung cancer and breast cancer.

In some embodiments of the methods disclosed herein, the GBP1 inhibitor is an inhibitor of any one of formulae (I)-(VII). In some cases the GBP1 inhibitor is any one of compounds 1-23.

As such, aspects of the method include contacting a sample with a subject compound (e.g., as described above) under conditions by which the compound inhibits GBP1. Any convenient protocol for contacting the compound with the sample may be employed. The particular protocol that is employed may vary, e.g., depending on whether the sample is in vitro or in vivo. For in vitro protocols, contact of the sample with the compound may be achieved using any convenient protocol. In some instances, the sample includes cells that are maintained in a suitable culture medium, and the complex is introduced into the culture medium. For in vivo protocols, any convenient administration protocol may be employed. Depending upon the potency of the compound, the cells of interest, the manner of administration, the number of cells present, various protocols may be employed.

In some embodiments, the subject method is a method of treating a subject for cancer. In some embodiments, the subject method includes administering to the subject an effective amount of a subject compound (e.g., as described herein) or a pharmaceutically acceptable salt thereof. The subject compound may be administered as part of a pharmaceutical composition (e.g., as described herein). In certain instances of the method, the compound that is administered is a compound of one of formulae (I)-(VII). In certain instances of the method, the compound that is administered is described by one of the compounds 1-23.

In some embodiments, an "effective amount" is an amount of a subject compound that, when administered to an individual in one or more doses, in monotherapy or in combination therapy, is effective to inhibit GBP1 by about 20% (20% inhibition), at least about 30% (30% inhibition), at least about 40% (40% inhibition), at least about 50% (50% inhibition), at least about 60% (60% inhibition), at least about 70% (70% inhibition), at least about 80% (80% inhibition), or at least about 90% (90% inhibition), compared to the GBP1 activity in the individual in the absence of treatment with the compound, or alternatively, compared to the GBP1 activity in the individual before or after treatment with the compound.

In some embodiments, an "effective amount" is an amount of a subject compound that, when administered to an individual in one or more doses, in monotherapy or in combination therapy, is effective to decrease tumor burden in the subject by about 20%, at least about 30%, at least about 40%, at least about 50%, at least about 60%, at least about 70%, at least about 80%, or at least about 90%, compared to tumor burden in the individual in the absence of treatment with the compound, or alternatively, compared to the tumor burden in the subject before or after treatment with the compound. As used herein the term "tumor burden" refers to the total mass of tumor tissue carried by a subject with cancer.

In some embodiments, an "effective amount" is an amount of a subject compound that, when administered to an individual in one or more doses, in monotherapy or in combination therapy, is effective to reduce the dose of radiotherapy required to observe tumor shrinkage in the subject by about 20%, at least about 30%, at least about 40%, at least about 50%, at least about 60%, at least about 70%, at least about 80%, or at least about 90%, compared to the dose of radiotherapy required to observe tumor shrinkage in the individual in the absence of treatment with the compound.

In some embodiments, an "effective amount" of a compound is an amount that, when administered in one or more doses to an individual having cancer, is effective to achieve a 1.5-log, a 2-log, a 2.5-log, a 3-log, a 3.5-log, a 4-log, a 4.5-log, or a 5-log reduction in tumor size.

In some embodiments, an effective amount of a compound is an amount that ranges from about 50 ng/kg body weight to about 50 µg/kg body weight (e.g., from about 50 ng/kg body weight to about 40 µg/kg body weight, from about 30 ng/kg body weight to about 20 µg/kg body weight, from about 50 ng/kg body weight to about 10 µg/kg body weight, from about 50 ng/kg body weight to about 1 µg/kg body weight, from about 50 ng/kg body weight to about 800 ng/kg body weight, from about 50 ng/kg body weight to about 700 ng/kg body weight, from about 50 ng/kg body weight to about 600 ng/kg body weight, from about 50 ng/kg body weight to about 500 ng/kg body weight, from about 50 ng/kg body weight to about 400 ng/kg body weight, from about 60 ng/kg body weight to about 400 ng/kg body weight, from about 70 ng/kg body weight to about 300 ng/kg body weight, from about 60 ng/kg body weight to about 100 ng/kg body weight, from about 65 ng/kg body weight to about 85 ng/kg body weight, from about 70 ng/kg body weight to about 90 ng/kg body weight, from about 200 ng/kg body weight to about 900 ng/kg body weight, from about 200 ng/kg body weight to about 800 ng/kg body weight, from about 200 ng/kg body weight to about 700 ng/kg body weight, from about 200 ng/kg body weight to about 600 ng/kg body weight, from about 200 ng/kg body weight to about 500 ng/kg body weight, from about 200 ng/kg body weight to about 400 ng/kg body weight, or from about 200 ng/kg body weight to about 300 ng/kg body weight).

In some embodiments, an effective amount of a compound is an amount that ranges from about 10 pg to about 100 mg, e.g., from about 10 pg to about 50 pg, from about 50 pg to about 150 pg, from about 150 pg to about 250 pg, from about 250 pg to about 500 pg, from about 500 pg to about 750 pg, from about 750 pg to about 1 ng, from about 1 ng to about 10 ng, from about 10 ng to about 50 ng, from about 50 ng to about 150 ng, from about 150 ng to about 250 ng, from about 250 ng to about 500 ng, from about 500 ng to about 750 ng, from about 750 ng to about 1 µg, from about 1 µg to about 10 µg, from about 10 µg to about 50 µg, from about 50 µg to about 150 µg, from about 150 µg to about 250 µg, from about 250 µg to about 500 µg, from about 500 µg to about 750 µg, from about 750 µg to about 1 mg, from about 1 mg to about 50 mg, from about 1 mg to about 100 mg, or from about 50 mg to about 100 mg. The amount can be a single dose amount or can be a total daily amount. The total daily amount can range from 10 pg to 100 mg, or can range from 100 mg to about 500 mg, or can range from 500 mg to about 1000 mg.

In some embodiments, a single dose of a compound is administered. In other embodiments, multiple doses are administered. Where multiple doses are administered over a period of time, the compound can be administered twice daily (qid), daily (qd), every other day (qod), every third day, three times per week (tiw), or twice per week (biw) over a period of time. For example, a compound is administered qid, qd, qod, tiw, or biw over a period of from one day to about 2 years or more. For example, a compound is administered at any of the aforementioned frequencies for one week, two weeks, one month, two months, six months, one year, or two years, or more, depending on various factors.

Administration of an effective amount of a subject compound to an individual with cancer can result in one or more of: 1) a reduction in tumor burden; 2) a reduction in the dose of radiotherapy required to effect tumor shrinkage (e.g. resulting from sensitization to radiotherapy); 3) a reduction in the spread of a cancer from one cell to another cell in an individual; 4) a reduction of morbidity or mortality in clinical outcomes; 5) shortening the total length of treatment when combined with other anti-cancer agents (e.g. resulting from sensitization to other anti-cancer agents); and 6) an improvement in an indicator of disease response (e.g., a reduction in one or more symptoms of cancer). Any of a variety of methods can be used to determine whether a treatment method is effective. For example, a biological sample obtained from an individual who has been treated with a subject method can be assayed.

Any of the compounds described herein can be utilized in the subject methods of treatment. In some embodiments, the compound specifically inhibits GBP1: pro-survival kinase interactions. In some embodiments, the compound results in sensitization of a cancer to radiation therapy and/or chemotherapy.

In some embodiments, the subject is mammalian. In certain instances, the subject is human. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys). The subject may be in need of treatment for cancer. The subject may be in need of treatment for a chemotherapy or radiotherapy resistant cancer. In some instances, the subject methods include diagnosing cancer, including any one of the cancers described herein. In some embodiments, the compound is administered as a pharmaceutical preparation.

In certain embodiments, the GBP1 inhibitor compound is a modified compound that includes a label, and the method further includes detecting the label in the subject. The selection of the label depends on the means of detection. Any convenient labeling and detection systems may be used in the subject methods, see e.g., Baker, "The whole picture," Nature, 463, 2010, p 977-980. In certain embodiments, the compound includes a fluorescent label suitable for optical detection. In certain embodiments, the compound includes a radiolabel for detection using positron emission tomography (PET) or single photon emission computed tomography (SPECT). In some cases, the compound includes a paramagnetic label suitable for tomographic detection. The subject compound may be labeled, as described above, although in some methods, the compound is unlabeled and a secondary labeling agent is used for imaging.

Combination Therapies

The subject compounds can be administered to a subject alone or in combination with an additional, i.e., second, active agent. Combination therapeutic methods where the subject GBP1 inhibitor compounds may be used in combination with a second active agent or an additional therapy, e.g., radiation therapy. The terms "agent," "compound," and "drug" are used interchangeably herein. For example, GBP1 inhibitor compounds can be administered alone or in conjunction with one or more other drugs, such as drugs employed in the treatment of diseases of interest, including but not limited to, immunomodulatory diseases and conditions and cancer. In some embodiments, the subject method further includes coadministering concomitantly or in sequence a second agent, e.g., a small molecule, a chemotherapeutic, an antibody, an antibody fragment, an antibody-drug conjugate, an aptamer, or a protein. In certain embodiments the second agent is a chemotherapeutic agent. In certain embodiments, the chemotherapeutic agent is a taxane. In some cases, the taxane is paclitaxel. In some embodiments, the method further includes performing radiation therapy on the subject.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

"Concomitant administration" of a known therapeutic drug or additional therapy with a pharmaceutical composition of the present disclosure means administration of the compound and second agent or additional therapy at such time that both the known drug and the composition of the present invention will have a therapeutic effect. Such concomitant administration may involve concurrent (i.e. at the same time), prior, or subsequent administration of the drug with respect to the administration of a subject compound. Routes of administration of the two agents may vary, where representative routes of administration are described in greater detail below. A person of ordinary skill in the art would have no difficulty determining the appropriate timing, sequence and dosages of administration for particular drugs or therapies and compounds of the present disclosure.

In some embodiments, the compounds (e.g., a subject compound and the at least one additional compound or therapy) are administered to the subject within twenty-four hours of each other, such as within 12 hours of each other, within 6 hours of each other, within 3 hours of each other, or within 1 hour of each other. In certain embodiments, the compounds are administered within 1 hour of each other. In certain embodiments, the compounds are administered substantially simultaneously. By administered substantially simultaneously is meant that the compounds are administered to the subject within about 10 minutes or less of each other, such as 5 minutes or less, or 1 minute or less of each other.

Also provided are pharmaceutical preparations of the subject compounds and the second active agent. In pharmaceutical dosage forms, the compounds may be administered in the form of their pharmaceutically acceptable salts, or they may also be used alone or in appropriate association, as well as in combination, with other pharmaceutically active compounds.

In conjunction with any of the subject methods, the GBP1 inhibitor compounds (e.g., as described herein) (or pharmaceutical compositions comprising such compounds) can be administered in combination with another drug designed to treat a cancer. In certain cases, the cancer is resistant to the drug. In certain cases, the GBP1 inhibitor compound can be administered prior to, at the same time as, or after the administration of the other drug. In certain cases, the cancer is selected from adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioma, glioblastomas, melanoma and various head and neck tumors. In certain cases, the cancer is ovarian cancer (OC), colorectal cancer, prostate cancer, head and neck cancer (HNC), lung cancer and breast cancer. In particular cases, the cancer is OV. In other cases, the cancer is a HNC.

For the treatment of cancer, the GBP1 inhibitor compounds can be administered in combination with a chemotherapeutic agent selected from alkylating agents, nitrosoureas, antimetabolites, antitumor antibiotics, plant (vinca) alkaloids, steroid hormones, taxanes, nucleoside analogs, steroids, anthracyclines, thyroid hormone replacement drugs, thymidylate-targeted drugs, Chimeric Antigen Receptor/T cell therapies, Chimeric Antigen Receptor/NK cell therapies, apoptosis regulator inhibitors (e.g., B cell CLL/lymphoma 2 (BCL-2) BCL-2-like 1 (BCL-XL) inhibitors), CARP-1/CCAR1 (Cell division cycle and apoptosis regulator 1) inhibitors, colony-stimulating factor-1 receptor (CSFIR) inhibitors, CD47 inhibitors, cancer vaccine (e.g., a Th17-inducing dendritic cell vaccine, or a genetically modified tyrosinase such as Oncept®) and other cell therapies.

Specific chemotherapeutic agents of interest include, but are not limited to, Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199. Peptidic compounds can also be used. Cancer chemotherapeutic agents of interest include, but are not limited to, taxane and active analogs and derivatives thereof. As used herein, the term "taxane" refers to compounds that have the basic taxane skeleton as a common structure feature. In certain embodiments, the taxane is paclitaxel. Paclitaxel is a highly derivatized diterpenoid (Wani, et al. (1971) J. Am. Chem. Soc. 93:2325-2327) which has been obtained from the harvested and dried bark of Taxus brevifolia (Pacific Yew) and Taxomyces andreanae, an endophytic fungus of the Pacific Yew (Stierle, et al. (1993) Science 60:214-216). Also included in the term "taxanes" are paclitaxel analogues, formulations, and derivatives, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel. As such, the term taxane refers to not only the common chemically available form of paclitaxel, but analogs (e.g., taxotere, as noted above) and paclitaxel conjugates (e.g., paclitaxel-PEG, paclitaxel-dextran, or paclitaxel-xylose). Also included within the term "taxane" are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

In some embodiments, the GBP1 inhibitor compounds can be administered in combination with a chemotherapeutic agent to treat cancer. In certain cases, the chemotherapeutic agent is a taxane. In some cases, the chemotherapeutic agent is paclitaxel.

Any convenient cancer vaccine therapies and agents can be used in combination with the subject GBP1 inhibitor compounds, compositions and methods. For treatment of cancer, e.g., ovarian cancer, the GBP1 inhibitor compounds can be administered in combination with a vaccination therapy, e.g., a dendritic cell (DC) vaccination agent that promotes Th1/Th17 immunity. Th17 cell infiltration correlates with markedly prolonged overall survival among ovarian cancer patients. In some cases, the GBP1 inhibitor compound finds use as adjuvant treatment in combination with Th17-inducing vaccination.

In certain instances, the combination provides an enhanced effect relative to either component alone; in some cases, the combination provides a supra-additive or synergistic effect relative to the combined or additive effects of the components. A variety of combinations of the subject compounds and the chemotherapeutic agent may be employed, used either sequentially or simultaneously. For multiple dosages, the two agents may directly alternate, or two or more doses of one agent may be alternated with a single dose of the other agent, for example. Simultaneous administration of both agents may also be alternated or otherwise interspersed with dosages of the individual agents. In some cases, the time between dosages may be for a period from about 1-6 hours, to about 6-12 hours, to about 12-24 hours, to about 1-2 days, to about 1-2 week or longer following the initiation of treatment.

Combination with Cancer Resistant Chemotherapeutics

Aspects of the present disclosure include methods of treating cancer, where the GBP1 inhibitor compounds (or pharmaceutical compositions comprising such compounds) can be administered in combination with a chemotherapeutic, wherein the cancer to be treated is resistant to the chemotherapeutic agent when administered alone. When a cancer patient is exposed to the particular chemotherapeutic without a subject GBP1 inhibitor, the chemotherapeutic agent is not effective to treat the patient's cancer. However, the effectiveness of the said chemotherapeutic agent can be restored and/or enhanced when the subject GBP1 inhibitor compounds are co-administered with the chemotherapeutic agent, e.g., enhanced by comparison to levels achieved with either agent alone. Any convenient chemotherapeutic agents can be used in the subject combination therapeutic methods. In some cases, the chemotherapeutic agent is a taxane. In some cases, the taxane is paclitaxel.

Cancers of interest which may be treated using the subject combination therapies include, but are not limited to, adrenal, liver, kidney, bladder, breast, colon, gastric, ovarian, cervical, uterine, esophageal, colorectal, prostate, pancreatic, lung (both small cell and non-small cell), thyroid, carcinomas, sarcomas, glioma, glioblastomas, melanoma and various head and neck tumors. In some cases, the cancer is ovarian, colorectal, prostate, head and neck cancer, lung cancer and breast cancer. In certain instances, the cancer is ovarian cancer or head and neck cancer.

Chemotherapeutic of interest include, but are not limited to, Taxane, Uracil analogues, Fluorouracil prodrug, Thymidylate Synthase inhibitors, Deoxycytidine analogue, DNA synthesis inhibitor (e.g. leading to S-phase apoptosis), Folate analogue, Dehydrofolate Reductase inhibitor, Anthracycline, intercalating agent, (e.g., leading to double strand breaks), Topoisomerase IIa inhibitor, microtubule disassembly inhibitor (e.g. leading to G2/M phase arrest/apoptosis), microtubule assembly inhibitor, microtubule function stabilizers (e.g. leading to G2/M-phase apoptosis), tubulin polymerization promoters, tubulin binding agent (e.g. leading to apoptosis by M-phase arrest) Epothilone B analogue, Vinka alkaloid, Nitrogen mustard, Nitrosourea, DNA alkylater (e.g., leading to interstrand crosslinks, apoptosis via p53), VEGF inhibitor, anti-angiogenic antibody, HER2 inhibitor, Quinazoline HER2 inhibitor, EGFR inhibitor, tyrosine kinase inhibitor, Sirolimus analogue, mTORC1 inhibitor (e.g., in breast cancer combination with Exemestane=Aromastase inhibitor inhibiting Estrogen production), Triazene, Dacarbazine prodrug, Methylhydrazine.

Combination with Cancer Resistant Radiation Therapy

Alternatively, for the methods of treating cancer, the GBP1 inhibitor compounds (or pharmaceutical compositions comprising such compounds) can be administered in combination with radiation therapy. In certain embodiments, the methods include administering radiation therapy to the subject. Again, the GBP1 inhibitor compound can be administered prior to, or after the administration of the radiation therapy. As such, the subject methods can further include administering radiation therapy to the subject. In some instances, the cancer to be treated is a radiation therapy resistant cancer. Without being bound to any particular theory, when the cancer to be treated has increased expression of GBP1 and enhanced metastatic and stem cell properties the cancer may be more resistant (i.e. less responsive) to radiation therapy. The combination of radiation therapy and administration of a subject compound can provide a synergistic therapeutic effect. For example, cell cycle analysis of GBP1 inhibitor SU093 and radiation combination treatment in OVCAR8 revealed that standalone treatment with either of SU093 or radiation therapy caused G1 phase arrest, but combination treatment caused G2/M phase arrest leading to apoptosis (e.g. see FIG. 5, panel B). One of the mechanisms through which a drug can sensitize the effect of radiation is its ability to block G2/M phase of the cell cycle. G2/M is the most radiosensitive phase in the cell cycle and arresting the cell population in this phase would likely sensitize them to the next cycle of radiation and enhance cell death. Further, inventors observed that a combination of 0.5 nM SU093 with 5 Gy radiation treatment exhibited similar effect as 10 Gy treatment of radiation alone (e.g. see FIG. 5, panel A). Accordingly, the sensitization of the cancer can be restored and/or enhanced when the subject GBP1 inhibitor compounds are co-administered with radiation therapy, e.g., effectiveness of RT is enhanced by comparison to levels achieved with RT alone. As such, aspects of the subject methods include administration of a reduced dosage and/or frequency/regimen of radiation treatment as compared to a therapeutically effective dosage and/or frequency/regimen of radiation treatment alone. In some cases, the radiation therapy is administered in combination with the subject compounds at a dosage and/or frequency effective to reduce risk of radiation damage to the subject, e.g., radiation damage that would be expected to occur under a therapeutically effective dosage and/or frequency/regimen of radiation treatment alone.

In some cases, the method includes administering an GBP1 inhibitor to the subject before radiation therapy. In some cases, the method includes administering an GBP1 inhibitor to the subject following exposure of the subject to radiation therapy. In certain cases, the method includes sequential administration of radiation therapy, followed by an GBP1 inhibitor, to a subject in need thereof.

Utility

The compounds and methods of the invention, e.g., as described herein, find use in a variety of applications. Applications of interest include, but are not limited to: research applications and therapeutic applications. Methods of the invention find use in a variety of different applications including any convenient application where inhibition of GBP1 is desired.

The subject compounds and methods find use in a variety of research applications. The subject compounds and methods may be used in the optimization of the bioavailability and metabolic stability of compounds.

The subject compounds and methods find use in a variety of therapeutic applications. Therapeutic applications of interest include those applications in cancer treatment. Of particular interest is treatment of a cancer that is resistant to radiation therapy and/or chemotherapy (e.g. by combination therapy). As such, the subject compounds find use in the treatment of a variety of different conditions in which the inhibition and/or treatment of cancer (e.g. a resistant cancer) in the host is desired. For example, the subject compounds and methods may find use in sensitizing a solid tumor cancer (e.g., as described herein), such as ovarian cancer, to chemotherapy and radiation therapy.

Pharmaceutical Compositions

The herein-discussed compounds can be formulated using any convenient excipients, reagents and methods. In certain embodiments, there is provided a pharmaceutical composition comprising a subject GBP1 inhibitor compound and a pharmaceutically acceptable excipient. A wide variety of pharmaceutically acceptable excipients are known in the art and need not be discussed in detail herein. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., $7^{th}$ ed., Lippincott, Williams, & Wilkins; and Handbook of Pharmaceutical Excipients (2000) A. H. Kibbe et al., eds., $3^{rd}$ ed. Amer. Pharmaceutical Assoc.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, the subject compound is formulated in an aqueous buffer. Suitable aqueous buffers include, but are not limited to, acetate, succinate, citrate, and phosphate buffers varying in strengths from 5 mM to 100 mM. In some embodiments, the aqueous buffer includes reagents that provide for an isotonic solution. Such reagents include, but are not limited to, sodium chloride; and sugars e.g., mannitol, dextrose, sucrose, and the like. In some embodiments, the aqueous buffer further includes a non-ionic surfactant such as polysorbate 20 or 80. Optionally the formulations may further include a preservative. Suitable preservatives include, but are not limited to, a benzyl alcohol, phenol, chlorobutanol, benzalkonium chloride, and the like. In many cases, the formulation is stored at about 4° C. Formulations may also be lyophilized, in which case they generally include cryoprotectants such as sucrose, trehalose, lactose, maltose, mannitol, and the like. Lyophilized formulations can be stored over extended periods of time, even at ambient temperatures. In some embodiments, the subject compound is formulated for sustained release.

In some embodiments, the subject compound and a second active agent (e.g., as described herein), e.g. a small molecule, a chemotherapeutic, an antibody, an antibody fragment, an antibody-drug conjugate, an aptamer, or a protein, etc. are administered to individuals in a formulation (e.g., in the same or in separate formulations) with a pharmaceutically acceptable excipient(s). In some embodiments, the second active agent is a chemotherapeutic agent. In certain embodiments the chemotherapeutic agent is a taxane e.g. pacliataxel.

In another aspect of the present invention, a pharmaceutical composition is provided, comprising, or consisting essentially of, a compound of the present invention, or a pharmaceutically acceptable salt, isomer, tautomer or prodrug thereof, and further comprising one or more additional active agents of interest. Any convenient active agents can be utilized in the subject methods in conjunction with the subject compounds. In some instances, the additional agent is a chemotherapeutic agent. The subject compound and chemotherapeutic agent, as well as additional therapeutic agents as described herein for combination therapies, can be administered orally, subcutaneously, intramuscularly, intranasally, parenterally, or other route. The subject compound and second active agent (if present) may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ. In certain cases, the therapeutic agents can be administered intranasally. In some cases, the therapeutic agents can be administered intratumorally.

In some embodiments, the subject compound and a chemotherapeutic agent are administered to individuals in a formulation (e.g., in the same or in separate formulations) with a pharmaceutically acceptable excipient(s). The chemotherapeutic agents include, but are not limited to alkylating agents, nitrosoureas, antimetabolites, antitumor antibiotics, plant (vinca) alkaloids, and steroid hormones. Peptidic compounds can also be used. Suitable cancer chemotherapeutic agents include taxane and active analogs and derivatives thereof; dolastatin and active analogs and derivatives thereof; and auristatin and active analogs and derivatives thereof (e.g., Monomethyl auristatin D (MMAD), monomethyl auristatin E (MMAE), monomethyl auristatin F (MMAF), and the like). See, e.g., WO 96/33212, WO 96/14856, and U.S. Pat. No. 6,323,315. Suitable cancer chemotherapeutic agents also include maytansinoids and active analogs and derivatives thereof (see, e.g., EP 1391213; and Liu et al (1996) Proc. Natl. Acad. Sci. USA 93:8618-8623); duocarmycins and active analogs and derivatives thereof (e.g., including the synthetic analogues, KW-2189 and CB 1-TM1); and benzodiazepines and active analogs and derivatives thereof (e.g., pyrrolobenzodiazepine (PBD).

The subject compound and second chemotherapeutic agent, as well as additional therapeutic agents as described herein for combination therapies, can be administered orally, subcutaneously, intramuscularly, parenterally, or other route. The subject compound and second chemotherapeutic agent may be administered by the same route of administration or by different routes of administration. The therapeutic agents can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into an affected organ.

The subject compounds may be administered in a unit dosage form and may be prepared by any methods well known in the art. Such methods include combining the subject compound with a pharmaceutically acceptable carrier or diluent which constitutes one or more accessory ingredients. A pharmaceutically acceptable carrier is selected on the basis of the chosen route of administration and standard pharmaceutical practice. Each carrier must be "pharmaceutically acceptable" in the sense of being compatible with the other ingredients of the formulation and not injurious to the subject. This carrier can be a solid or liquid and the type is generally chosen based on the type of administration being used.

Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Any drug delivery device or system that provides for the dosing regimen of the instant disclosure can be used. A wide variety of delivery devices and systems are known to those skilled in the art.

Additional Embodiments

Additional embodiments are set forth in the following clauses:

Clause 1. A GBP1 inhibitor of formula (I):

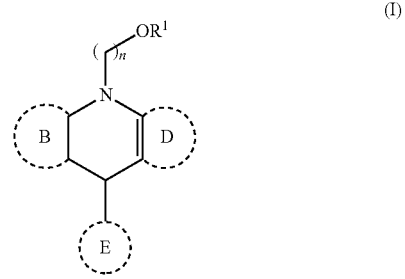

wherein:
R$^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
Ring B and Ring E are each independently selected from a $C_{5-6}$ membered carbocycle, a substituted $C_{5-6}$ membered carbocycle, a $C_{5-6}$ membered heteroaryl, a substituted $C_{5-6}$ membered heteroaryl, a $C_{5-6}$ membered heterocycle containing up to two atoms selected from N, O or S and a substituted $C_{5-6}$ membered heterocycle containing up to two atoms selected from N, O or S;
Ring D is selected from a $C_{5-6}$ carbocycle, a $C_{5-6}$ heterocycle containing up to two atoms selected from N, O or S, a substituted $C_{5-6}$ carbocycle, and a substituted $C_{5-6}$ heterocycle containing up to two atoms selected from N, O or S; and
n is an integer from 1 to 6,
or a pro-drug, a pharmaceutically acceptable salt or a solvate thereof.

Clause 2. The GBP1 inhibitor according to clause 1, wherein the Ring D is selected:

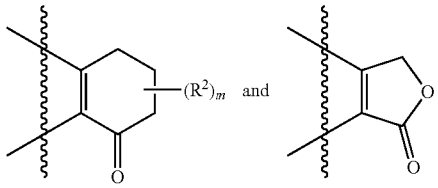

wherein:
each $R^2$ are independently selected from alkyl, substituted alkyl, acyl, substituted acyl, alkoxy, substituted alkoxy, carbocycle, substituted carbocycle, heterocycle, substituted heterocycle, heteroaryl, substituted heteroaryl, F, $CF_3$, CN, $NO_2$ and methoxy; and
m is an integer from 0 to 6.

Clause 3. The GBP1 inhibitor according to clause 1 or 2, wherein the Ring B or Ring E are each independently selected from aryl, substituted aryl, pyrrole, substituted pyrrole, imidazole, substituted imidazole, pyrazole, substituted pyrazole, furan, substituted furan, oxazole, substituted oxazole, isoxazole, substituted isoxazole, thiophene, substituted thiophene, thiazole, substituted thiazole, isothiazole, substituted isothiazole, pyridine, substituted pyridine, pyrimidine, substituted pyrimidine, 2-H-pyran, substituted 2-H-pyran, 2-H-thiopyran and substituted 2-H-thiopyran.

Clause 4. The GBP1 inhibitor according to clause 3, wherein the Ring B is of the formula (B1):

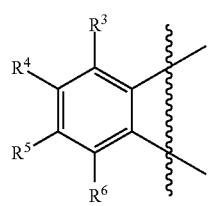

wherein:
$R^3$, $R^4$, $R^5$ and $R^6$ are each independently selected from H, OH, methoxy, halogen, $CF_3$, CN and $NO_2$;
or any of $R^4$ and $R^5$, $R^3$ and $R^4$, $R^5$ and $R^6$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S.

Clause 5. The GBP1 inhibitor according to clause 3, wherein the Ring E is of the formula (E1):

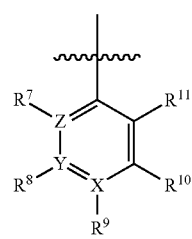

wherein:
X, Y and Z are each independently selected from C or N; and
$R^7$, $R^8$, $R^9$, $R^{10}$ and $R^{11}$ are each independently selected from H, F, $CF_3$, CN, $NO_2$, methoxy, Cl, Br, OH and alkyl;
or any of $R^7$ and $R^8$, $R^8$ and $R^9$, $R^9$ and $R^{10}$, $R^{10}$ and $R^{11}$ together with the carbons to which they are attached form a $C_{5-6}$ carbocycle, $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S.

Clause 6. The GBP1 inhibitor according to any one of clauses 1 to 5, wherein n is 2.

Clause 7. The GBP1 inhibitor according to clause 3, wherein the Ring B is selected from the formulae (B2) and (B3):

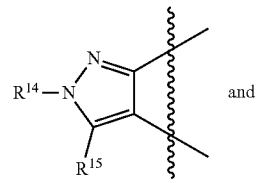

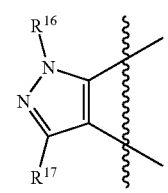

wherein:
$R^{14}$, $R^{15}$, $R^{16}$ and $R^{17}$ are each independently selected from H, alkyl, aryl and substituted aryl.

Clause 8. The GBP1 inhibitor according to any one of clauses 1 to 6, of the formula (II):

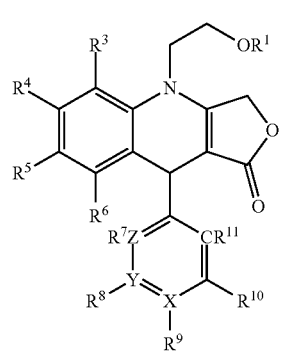

wherein: $R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
$R^3$, $R^4$, $R^5$ and $R^6$ are independently selected from H, OH, methoxy, alkyl, halogen, $CF_3$, CN and $NO_2$;
or any of $R^4$ and $R^5$, $R^3$ and $R^4$, $R^5$ and $R^6$ together with the carbons to which they are attached form a $C_{5-6}$ carbocycle, a $C_{5-6}$ heterocycle containing up to two atoms selected from N, O or S, a substituted $C_{5-6}$ carbocycle, and a substituted $C_{5-6}$ membered heterocycle containing up to two atoms selected from N, O or S;

X, Y and Z are each independently selected from C or N;

$R^{10}$ is selected from F, $CF_3$, CN, $NO_2$, OH and alkyl;

$R^7$, $R^8$, $R^9$ and $R^{11}$ are each independently selected from H, F, $CF_3$, CN, $NO_2$, methoxy, Cl, Br, OH and alkyl;

or any of $R^7$ and $R^8$, $R^8$ and $R^9$, $R^9$ and $R^{10}$, $R^{10}$ and $R^{11}$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S.

or a pro-drug, a pharmaceutically acceptable salt or a solvate thereof.

Clause 9. The GBP1 inhibitor according to any one of clauses 1 to 6, of the formula (III):

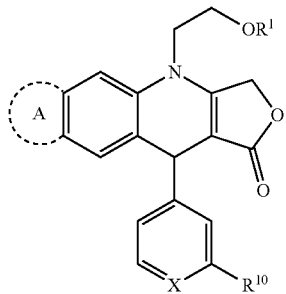

(III)

wherein:

Ring A is selected from a $C_{5-6}$ carbocycle, a $C_{5-6}$ heterocycle containing up to two atoms selected from N, O or S, a substituted $C_{5-6}$ carbocycle, and a substituted $C_{5-6}$ heterocycle containing up to two atoms selected from N, O or S;

X is C or N;

$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

$R^{10}$ is selected from F, $CF_3$, CN, $NO_2$, OH, alkyl and methoxy, or a pro-drug, a pharmaceutically acceptable salt or a solvate thereof.

Clause 10. The GBP1 inhibitor according to clause 9, wherein the Ring A is selected from 1,3-dioxolane, cyclopentane, cyclopentene, 1,4-dioxane, cyclohexane, cyclohexene.

Clause 11. The GBP1 inhibitor of clause 10, wherein the Ring A is 1,3-dioxolane.

Clause 12. The GBP1 inhibitor according to any one of clauses 9 to 11, wherein $R^{10}$ is F.

Clause 13. The GBP1 inhibitor according to any one of clauses 9 to 11, wherein $R^{10}$ is $CF_3$.

Clause 14. The GBP1 according to any one of clauses 9 to 11, wherein $R^{10}$ is $NO_2$.

Clause 15. The GBP1 inhibitor according to any one of clauses 8 to 14, wherein X is C.

Clause 16. The GBP1 inhibitor according to any one of clauses 8 to 14, wherein X is N.

Clause 17. A GBP1 inhibitor according to any one of clauses 1 to 6 of the formula (IV):

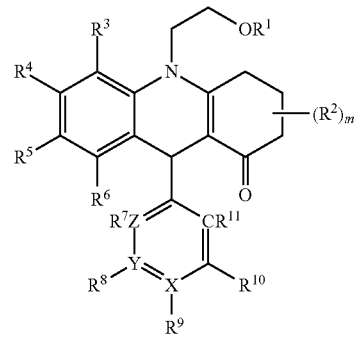

(IV)

wherein:

$R^1$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

$R^2$ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;

$R^3$, $R^4$, $R^5$ and $R^6$ are independently selected from H, OH, methoxy, alkyl, halogen, $CF_3$, CN and $NO_2$;

or any of $R^4$ and $R^5$, $R^3$ and $R^4$, $R^5$ and $R^6$ together with the carbons to which they are attached form a $C_{5-6}$ carbocycle, a $C_{5-6}$ heterocycle containing up to two atoms selected from N, O or S, a substituted C carbocycle, and a substituted $C_{5-6}$ membered heterocycle containing up to two atoms selected from N, O or S;

X, Y and Z are each independently selected from C or N;

$R^7$, $R^8$, $R^9$, $R^{10}$ and $R^{11}$ are each independently selected from H, F, $CF_3$, CN, $NO_2$, methoxy, Cl, Br, OH and alkyl;

or any of $R^7$ and $R^8$, $R^8$ and $R^9$, $R^9$ and $R^{10}$, $R^{10}$ and $R^{11}$ together with the carbons to which they are attached form a $C_{5-6}$ carbocycle, a $C_{5-6}$ heterocycle containing up to two atoms selected from N, O or S, a substituted $C_{5-6}$ carbocycle, or a substituted $C_{5-6}$ membered heterocycle containing up to two atoms selected from N, O or S; and m is an integer from 0 to 6, or a pro-drug, a pharmaceutically acceptable salt or a solvate thereof.

Clause 18. The GBP inhibitor according to clause 17, of the formula (V):

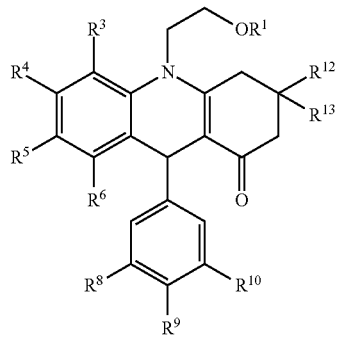

(V)

wherein:
R¹ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
R³, R⁴, R⁵ and R⁶ are independently selected from H, OH, methoxy, alkyl, halogen, CF₃, CN and NO₂;
or any of R⁴ and R⁵, R³ and R⁴, R⁵ and R⁶ together with the carbons to which they are attached form a C₅₋₆ carbocycle, a C₅₋₆ heterocycle containing up to two atoms selected from N, O or S, a substituted C₅₋₆ carbocycle, or a substituted C₅₋₆ membered heterocycle containing up to two atoms selected from N, O or S;
R¹² and R¹³ are each independently selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl, F, CF₃, CN, NO₂ and methoxy;
R⁸, R⁹ and R¹⁰ are each independently selected from H, F, CF₃, CN, NO₂, methoxy, Cl, Br, OH and alkyl;
or any of R⁸ and R⁹ or R⁹ and R¹⁰ together with the carbons to which they are attached form a C₅₋₆ carbocycle, or C₅₋₆ heterocycle containing up to two atoms selected from N, O or S, a substituted C₅₋₆ carbocycle, or a substituted C₅₋₆ membered heterocycle containing up to two atoms selected from N, O or S,
or a pro-drug, a pharmaceutically acceptable salt or a solvate thereof.

Clause 19. The GBP1 inhibitor according to clause 17 or 18, wherein R⁴ is methoxy and each of R³, R⁵ and R⁶ are H.

Clause 20. The GBP1 inhibitor according to clause 17 or 18, wherein each of R³, R⁴ and R⁶ are H and R⁵ is methoxy.

Clause 21. The GBP1 inhibitor according to clause 17 or 18, wherein R⁴ and R⁵ together with the carbons to which they are attached form a group selected from 1,3-dioxolane, cyclopentane, cyclopentene, 1,4-dioxane, cyclohexane, cyclohexene; and
each of R³ and R⁶ are H.

Clause 22. The GBP1 inhibitor of clause 21, wherein R⁴ and R⁵ together with the carbons to which they are attached form 1,3-dioxolane; and
each of R³ and R⁶ are H.

Clause 23. The GBP1 inhibitor according to any one of clauses 17 to 22, wherein R¹⁰ is F and R⁸ and R⁹ are both hydrogen.

Clause 24. The GBP1 inhibitor according to any one of clauses 17 to 22, wherein R⁸, R⁹ and R¹⁰ and each hydrogen.

Clause 25. The GBP1 inhibitor according to any one of clauses 17 to 22, wherein R⁸, R⁹ and R¹⁰ are each methoxy.

Clause 26. The GBP1 inhibitor according to clause 9, wherein formula (III) is a structured selected from:

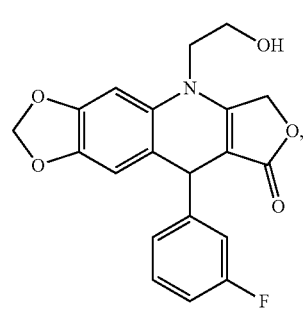

(1)

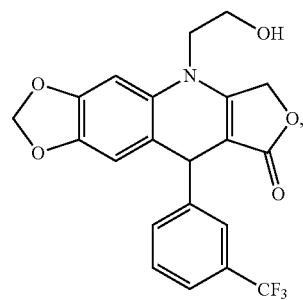

(2)

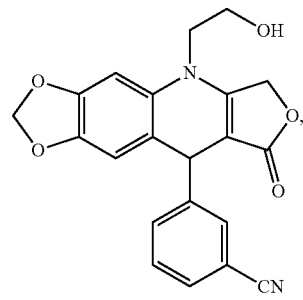

(3)

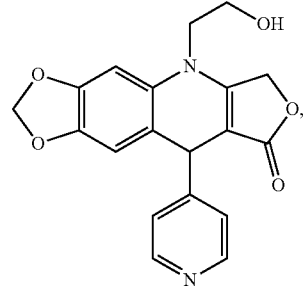

(4)

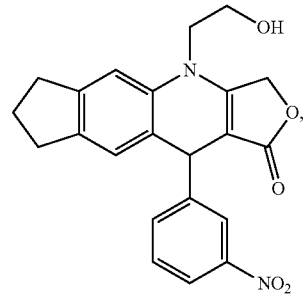

(5)

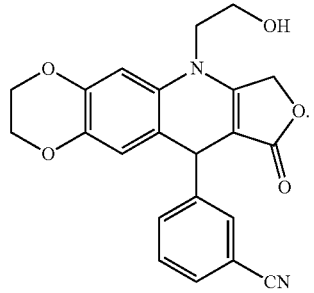
(6)
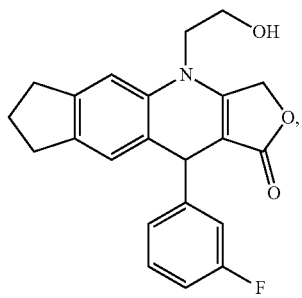
(7)
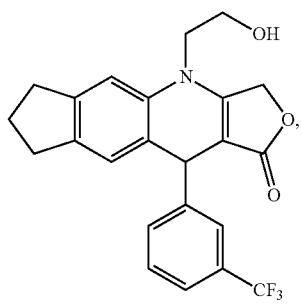
(8)
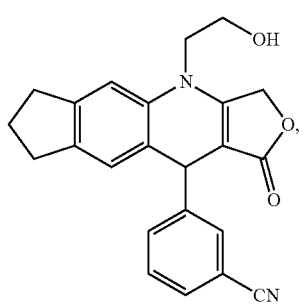
(9)
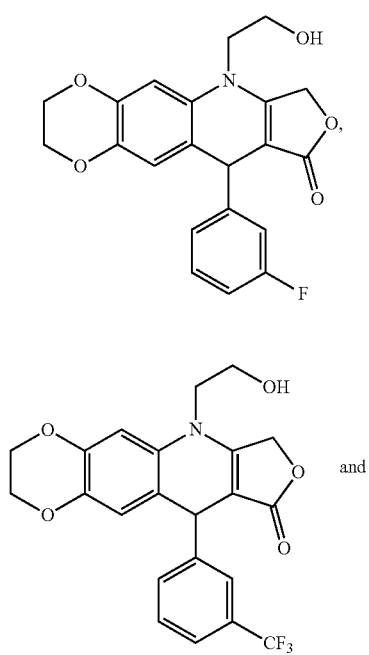
(10) and
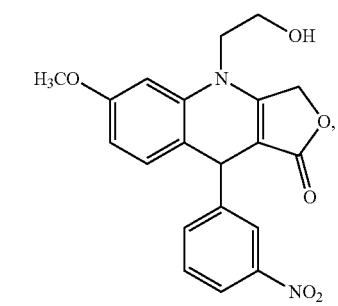
(11)
Clause 27. The GBP1 inhibitor according to clause 8, wherein formula (II) is a structure selected from:
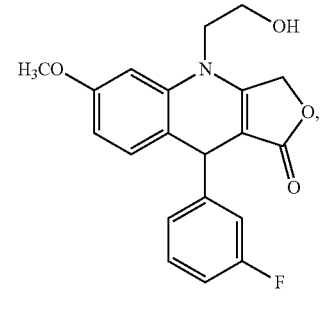
(12)
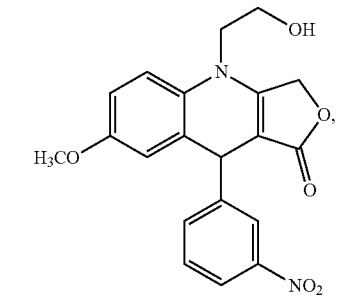
(13)
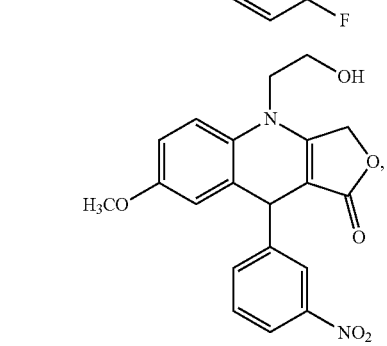
(14)
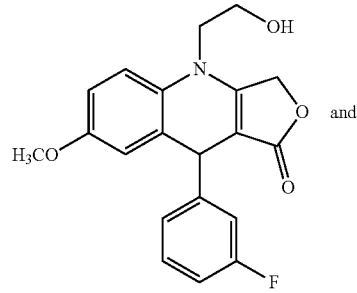
(15) and -continued
(16)
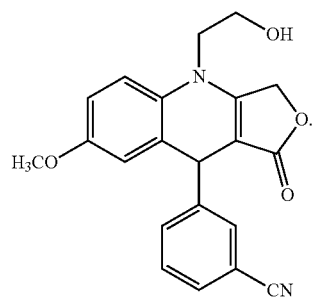
Clause 28. The GBP1 inhibitor according to clause 18, wherein formula (V) is a structure selected from:
(17)
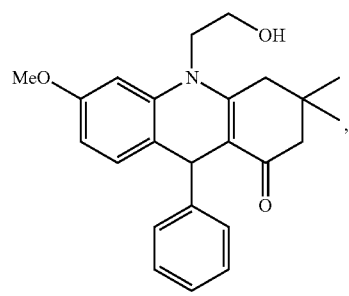
(18)
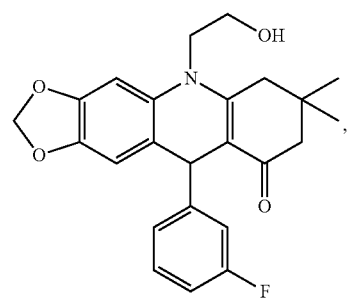
(19)
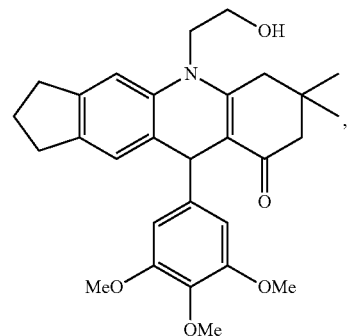
-continued
(20)
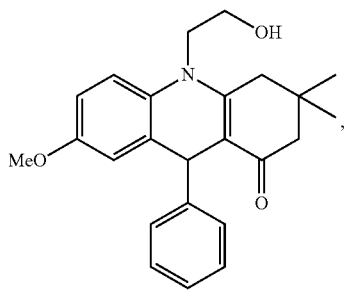
(21)
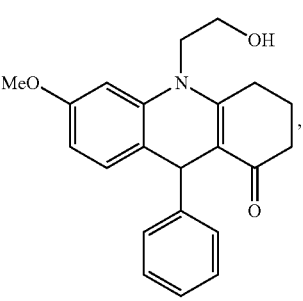
(22)
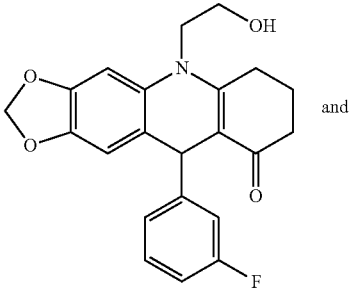
and
(23)
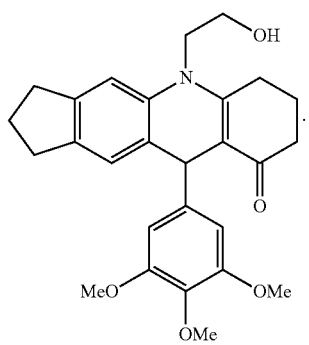

Clause 29. A GBP1 inhibitor according to clause 1, of the formula (VI):

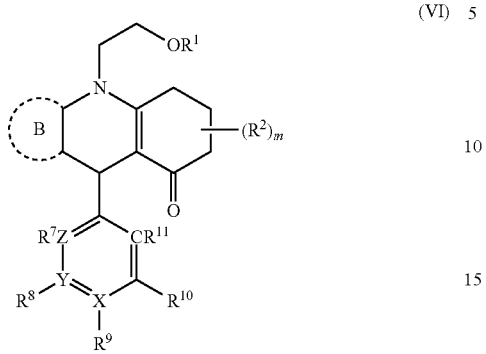

(VI)

wherein:
- R¹ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
- R² is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
- X, Y and Z are each independently selected from C or N;
- R⁷, R⁸, R⁹, R¹⁰ and R¹¹ are each independently selected from H, F, CF₃, CN, NO₂, methoxy, Cl, Br, OH and alkyl;
- or any of R⁷ and R⁸, R⁸ and R⁹, R⁹ and R¹⁰, R¹⁰ and R¹¹ together with the carbons to which they are attached form a C₅₋₆ carbocycle, or C₅₋₆ heterocycle containing up to two atoms selected from N, O or S, a substituted C₅₋₆ carbocycle, or a substituted C₅₋₆ membered heterocycle containing up to two atoms selected from N, O or S;
- Ring B is selected from the formulae (B2) and (B3):

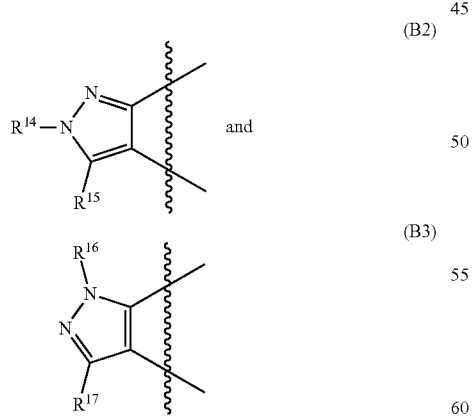

(B2)

(B3)

wherein R¹⁴, R¹⁵, R¹⁶ and R¹⁷ are each independently selected from H, alkyl, aryl and substituted aryl; and
m is an integer from 0 to 6,
or a pro-drug, a pharmaceutically acceptable salt or a solvate thereof.

Clause 30. The GBP inhibitor according to clause 1, of the formula (VII):

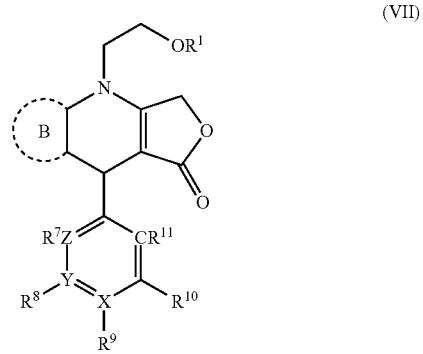

(VII)

wherein:
- R¹ is selected from H, alkyl, substituted alkyl, acyl, substituted acyl, alkoxy, substituted alkoxy, carbocycle, substituted carbocycle, heterocycle, substituted heterocycle, heteroaryl, substituted heteroaryl and a protecting group;
- X, Y and Z are each independently selected from C or N;
- R⁷, R⁸, R⁹, R¹⁰ and R¹¹ are each independently selected from H, F, CF₃, CN, NO₂, methoxy, Cl, Br, OH and alkyl;
- or any of R⁷ and R⁸, R⁸ and R⁹, R⁹ and R¹⁰, R¹⁰ and R¹¹ together with the carbons to which they are attached form a C₅₋₆ carbocycle, or C₅₋₆ heterocycle containing up to two atoms selected from N, O or S, a substituted C₅₋₆ carbocycle, or a substituted C₅₋₆ membered heterocycle containing up to two atoms selected from N, O or S; and
- Ring B is selected from the formulae (B2) and (B3):

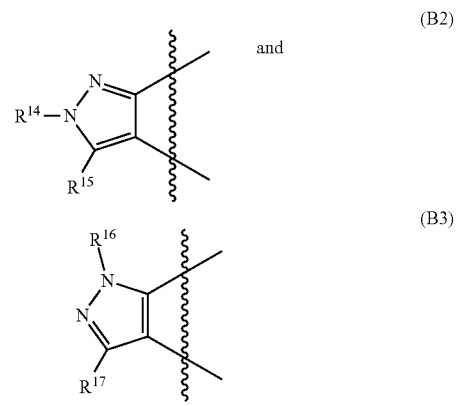

(B2)

(B3)

wherein R¹⁴, R¹⁵, R¹⁶ and R¹⁷ are each independently selected from H, alkyl, aryl and substituted aryl;
or a pro-drug, a pharmaceutically acceptable salt or a solvate thereof.

Clause 31. The GBP inhibitor according to clause 29 or 30, wherein the Ring B is of the formula (B2).

Clause 32. The GBP inhibitor according to clause 29 or 30, wherein the Ring B is of the formula (B3).

Clause 33. A pharmaceutical composition comprising: a GBP1 inhibitor according to any one of clauses 1 to 32; and a pharmaceutically acceptable excipient.

Clause 34. A method of inhibiting GBP1, the method comprising: contacting a cellular sample with a GBP1 inhibitor according to any one of clauses 1 to 32 to inhibit GBP1: pro-survival kinase (e.g. serine/threonine-protein kinase pim-1 (PIM1)) interactions.

Clause 35. A method of treating cancer, the method comprising: administering to a subject in need thereof an effective amount of a GBP1 inhibitor according to any one of clauses 1 to 32 to inhibit GBP1: pro-survival kinase (e.g. serine/threonine-protein kinase pim-1 (PIM1)) interactions and treat the subject for cancer.

Clause 36. The method of clause 35, wherein the cancer is selected from ovarian cancer (OC), colorectal cancer, prostate cancer, head and neck cancer (HNC), lung cancer and breast cancer.

Clause 37. The method of clause 35 or 36, further comprising administration of one or more additional active agents.

Clause 38. The method of clause 37, wherein the one or more additional active agents is a small molecule, a chemotherapeutic, an antibody fragment, an antibody-drug conjugate, an aptamer, or a protein.

Clause 39. The method of clause 38, wherein the one or more additional agents is a chemotherapeutic agent.

Clause 40. The method of clause 39, wherein the chemotherapeutic agent is paclitaxel.

Clause 41. The method according to any one of clauses 35 to 40, further comprising administering radiation therapy to the subject.

Clause 42. The method of clause 41, wherein the GBP1 inhibitor is administered to the subject before radiation therapy.

Clause 43. The method of clause 41, wherein the GBP1 inhibitor is administered following exposure of the subject to radiation therapy.

Clause 44. The method of any one of clauses 41 to 43, wherein the radiation therapy is administered at a dosage and/or frequency effective to reduce radiation damage to the subject.

Clause 45. The method according to any one of clauses 35 to 44, wherein the cancer is resistant towards radiation therapy.

Clause 46. The method according to any one of clauses 35 to 45, wherein the cancer is resistant towards chemotherapy.

Clause 47. The method according to any one of clauses 35 to 46, wherein the GBP1 inhibitor sensitizes the cancer to chemotherapy and radiation therapy.

EXAMPLES

The following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present disclosure. All such modifications are intended to be within the scope of the claims appended hereto.

Example 1: Compound Synthesis

Scheme A Synthesis of amino alcohol substrates:

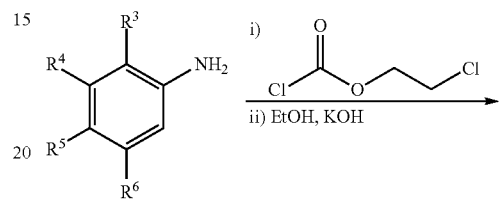

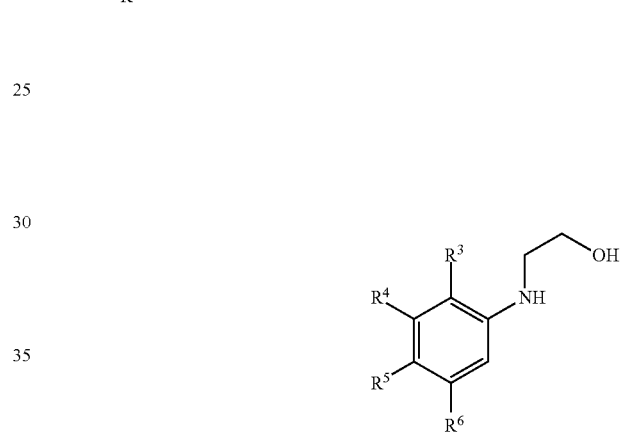

Amino alcohol substrates (i.e. which become Ring B of the subject compounds) were obtained by reacting corresponding commercially available aryl amines with chloroethylchloroformate, followed by reaction with potassium hydroxide in ethanol.

Scheme B
Multicomponent Synthesis of Exemplary GBP1 inhibitors
(e.g. of formulae (II)-(III)).

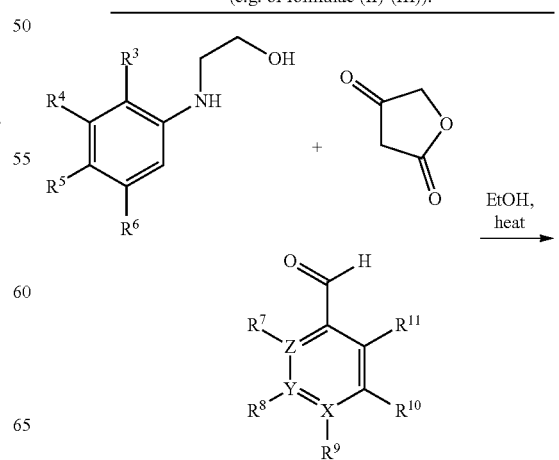

-continued

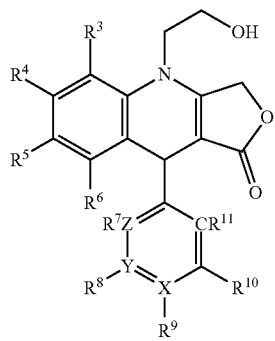

The amino alcohol substrates (e.g. as obtained from the reaction depicted in Scheme A above) were reacted with the corresponding commercially available benzaldehydes and tetronic acid using ethanol as a solvent to afford exemplary GBP1 inhibitor compounds of formulae (II)-(III) as described herein.

Scheme C
Multicomponent Synthesis of Exemplary GBP1 inhibitors
(e.g. of formula (IV)-(V)).

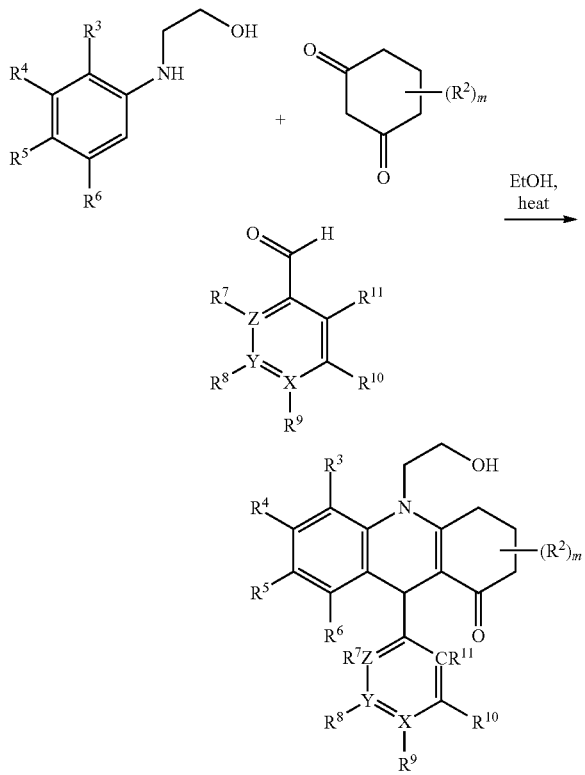

The amino alcohol substrates (e.g. as obtained from the reaction depicted in Scheme A above) were reacted with the corresponding commercially available benzaldehydes and corresponding 1,3-dione (e.g. 5,5-dimethylcyclohexane-1,3-dione or cyclohexane-1,3-dione) using ethanol as a solvent to afford exemplary GBP1 inhibitor compounds of formulae (IV)-(V) as described herein.

General Procedure for Synthesis of Exemplary GBP1 Inhibitors According to Scheme B:

An equimolar mixture of tetronic acid, substituted aniline, and aromatic aldehyde was dissolved in the minimum volume of ethanol. The reaction mixture was refluxed for 30-60 min. After cooling, the precipitate was filtered off, washed with minimal cold ethanol, and then recrystallized from ethanol to afford the desired GBP1 inhibitor compound. (As previously reported: Tratrat, C.; Giorgi-Renault, S.; Husson, H. P., A multicomponent reaction for the one-pot synthesis of 4-aza-2,3-didehydropodophyllotoxin and derivatives. *Organic. Lett.* 2002, 19, 3187-3189).

Example 2: Compound Testing

Selected compounds as described herein and other derivatives were prepared and tested for activity in a variety of assays.

Compound Activity

Exemplary compounds (1)-(17) and previously identified compound SU093 (Andreoli, M., Persico, M.; Kumar, A.; Orteca, N.; Kumar, V.; Pepe, A.; Mahalingam, S.; Alegria, A. E.; Petrella, L.; Sevciunaite, L.; Camperchioli, A.; Mariani, M.; Di Dato, A.; Novellino, E.; Scambia, G., Malhotra, S. V.; Ferlini, C.; Fattorusso, C., Identification of the First Inhibitor of the GBP1:PIM1 Interaction. Implications for the Development of a New Class of Anticancer Agents against Paclitaxel Resistant Cancer Cells. *Journal of Medicinal Chemistry* 2014, 57 (19), 7916-7932) were tested for GBP1 inhibition using a cell-based reporter assay in ovarian cancer cell line OVCAR-8 stably transfected with GBP-1-luciferase. Tables 1 and 2 below outlines the percentage of GBP1 expression in OVCAR-8 cells for each of the 17 compounds tested. Screening studies identified SU056 (also referred to herein as Compound (1)) to be a highly potent inhibitor of GBP1 protein (Table 2).

TABLE 1

GBP1 inhibition of GBP1 inhibitors in OVCAR-8 ovarian cancer cell line

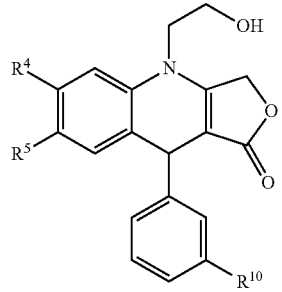

| Compd. ID | $R^4$ | $R^5$ | $R^{10}$ | % GBP1 expression OVCAR-8 @5 nM | @10 nM |
|---|---|---|---|---|---|
| SU093 | $OCH_3$ | H | H | 60.3 | 51.0 |
| SU043 (12) | $OCH_3$ | H | $NO_2$ | 127.9 | 133.0 |
| SU054 (13) | $OCH_3$ | H | F | 64.9 | 79.54 |
| SU073 (14) | H | $OCH_3$ | $NO_2$ | 108.2 | 117.5 |
| SU080 (15) | H | $OCH_3$ | Br | 134.4 | 131.4 |
| SU071 (16) | H | $OCH_3$ | F | 139.9 | 132.7 |
| SU087 (17) | H | $OCH_3$ | CN | 129.4 | 128.8 |

TABLE 2

GBP1 inhibition of GBP1 inhibitors in OVCAR-8 ovarian cancer cell line

| Compound ID | Ring A | X | R¹⁰ | % GBP1 expression OVCAR-8 @5 nM | % GBP1 expression OVCAR-8 @10 nM |
|---|---|---|---|---|---|
| SU056 (1) | 1,3-dioxolane | C | F | 54.16 | 43.36 |
| SU060 (2) | 1,3-dioxolane | C | CF₃ | 61.0 | 81.1 |
| SU058 (3) | 1,3-dioxolane | C | CN | 91.66 | 111.34 |
| SU074 (4) | 1,3-dioxolane | N | H | 128.5 | 106.4 |
| SU042 (5) | cyclopentyl | C | NO₂ | 54.26 | 43.15 |
| SU044 (6) | cyclopentyl | C | F | 90.16 | 110.37 |
| SU061 (7) | cyclopentyl | C | CF₃ | 91.26 | 124.96 |
| SU048 (8) | cyclopentyl | C | CN | 90.15 | 121.17 |
| SU049 (9) | 1,3-dioxane | C | F | 65.0 | 86.4 |
| SU065 (10) | 1,3-dioxane | C | CF₃ | 95.83 | 117.86 |
| SU050 (11) | 1,3-dioxane | C | CN | 138.7 | 132.54 |

To demonstrate the cytotoxic effect of the GBP1 inhibitor compounds against different solid tumor cell lines, the cytotoxicity effect of compound SU093 against different cancer cell lines which have been reported to overexpress GBP1 protein was assessed by MTT assay. The results of the MTT assay are shown in Table 3 below. It was observed that SU093 was highly cytotoxic for all cell lines tested with $IC_{50}$ values in the nanomolar range.

TABLE 3

Cytotoxicity effect of SU093 against different cancer cell lines evaluated by MTT assay.

| Cancer | Cell Line | $IC_{50}$ (nM) |
|---|---|---|
| Ovarian | OVCAR8 | 2.49 |
| Colorectal | HCT116 | 1.24 |
| Prostate | DU145 | 1.12 |
| Head and Neck | SSC-90 | 3.23 |
| Lung | A549 | 2.48 |
| Breast | MCF7 | 6.23 |

Example 3: GBP1 Protein Studies

GBP1 has Modulatory Role in HNC Tumor Microenvironment (TME):

To evaluate the effect of GBP1 expression of cell viability, GBP1 overexpressed (OV) and knockdown (KD) SCC-90 cell lines were constructed, which was an HPV-positive HNC cell line, using lentiviral transfection. Cell viability experiments performed on these cell lines using MTT assay showed that, GBP1-OV cells were more proliferative then GBP1-KD (FIG. 1, panel A). Similar results were obtained in FaDu cell line, an HPV-negative HNC cell line, which suggested that that role of GBP1 is HPV independent.

GBP1 overexpression increased cell migration properties in SCC-90 in normal as well as hypoxic conditions as shown by Boyden chambers assay (FIG. 1, panel B). Immunostaining experiments showed that GBP1-OV cells induced the expression of epithelial-to-mesenchymal transition (EMT) marker Vimentin, while GBP1-KD cells induced the expression of mesenchymal-to-epithelial transition (MET) marker E-cadherin in SCC-90 cells (FIG. 1, panel C). These results indicate that because of the overexpression of GBP1, cells acquire more mesenchymal nature and thus result in accelerated metastasis.

Hypoxia-induced up-regulation of vascular endothelial growth factor (VEGF) expression is a critical event leading to tumor neovascularization. Hypoxia stimulates and stabilizes HIF-1α, which is a transcriptional activator of VEGF. Many soluble factors are associated in the tumor microenvironment (TME) including VEGFs, fibroblast growth factors (FGFs), platelet-derived growth factors (PDGFs) and chemokines such as IL-6. These factors play an important role in stimulation of endothelial cells and their associated pericytes during the neovascularization that is needed for cancer growth (Carmeliet, P.; Jain, R. K., Molecular mechanisms and clinical applications of angiogenesis. *Nature* 2011, 473 (7347), 298-307). Immunostaining experiments using confocal microscopy showed that GBP1 overexpression facilitated Hif1α nuclear localization in SCC-90 cells after 24 h of incubation under conditions of 1% oxygen (FIG. 1, panel D). Immunoblotting experiments also showed elevated cellular and secretary level of VEGF and IL-6 in GBP1-OV cells (FIG. 1, panel E), which confirmed the role of GBP1 Hif1α nuclear localization.

Down-regulation of Major Histocompatibility Complex class I molecules (MHC-I) expression is a widespread phenomenon used by tumor cells to escape antitumor T-cell-mediated immune responses. Reduction in B2-microglobulin (B2M, a molecule associated with MHC-I) helps cancer cells to hide them from immune system (Hicklin, D. J.; Marincola, F. M.; Ferrone, S., HLA class I antigen down-regulation in human cancers: T-cell immunotherapy revives an old story. *Molecular Medicine Today* 1999, S (4), 178-186.) In experiments conducted herein, reduced expression B2M in GBP1-OV cells was observed (FIG. 1, panel F). However, upon treatment of GBP1 inhibitor SU093 with SCC-90 cells, induced expression of B2M was observed. Without being bound to any particular theory, these results indicate that modulation of GBP1 expression by SU093 may play a role in immune-modulation.

Figure 2:
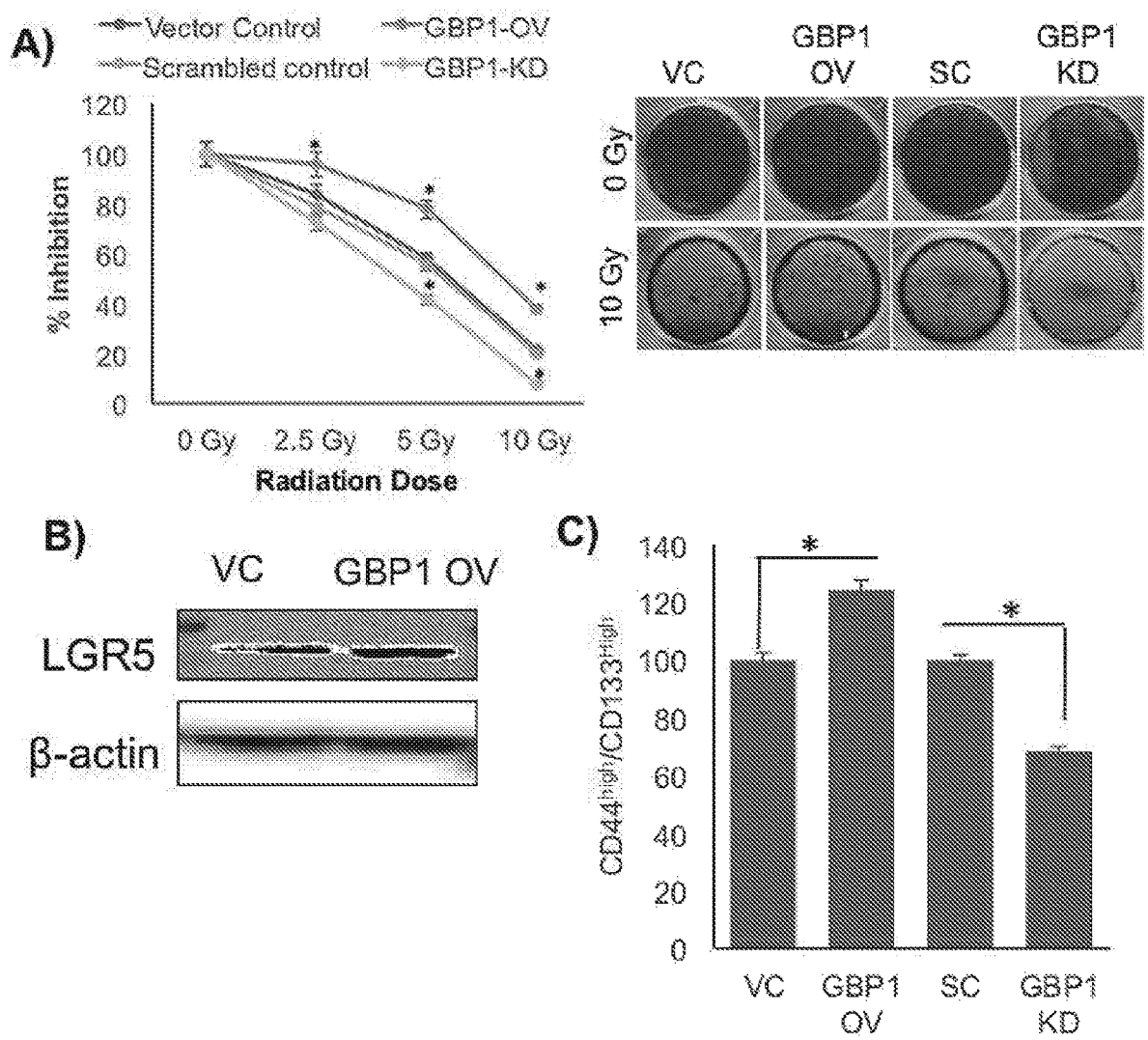
FIG. 2, panels A-2.

GBP1 Overexpression Leads to Radiation Resistance:

Clonogenic assay revealed that GBP1-OV SCC-90 cells were more resistant towards radiation compared to GBP1-KD cells (FIG. 2, panel A). To further support this, the expression of stemness marker LGR5 by western blot was checked, and its enhanced expression in GBP1 overexpressed cells was observed (FIG. 2, panel B). Immunostaining experiments on additional stemness markers CD44[high]/CD133[High] showed about 24% increase in their expression in GBP1-OV cells, while 32% decrease in GBP1-KD cells, as compared to wild type (WT) cells (FIG. 2, panel C). Evidence indicates that survival and behavior of cancer stem cells (CSCs) are positively regulated by specific stimuli received from the tumor microenvironment, which dictates the maintenance of stemness, invasiveness, and protection against therapy-induced apoptotic signals (Rycaj, K.; Tang, D. G., Cancer stem cells and radioresistance. *International Journal of Radiation Biology* 2014, 90 (8), 615-621). CSCs are per se endowed with multiple treatment resistance capabilities, thus the eradication of CSC pools offers a precious strategy in achieving a long-term cancer remission. Results discussed herein indicate that GBP1 expression is associated with the modulation of specific stemness markers. These results suggest that GBP1 overexpressing cells are more robust and less responsive toward radiation therapy and have enhanced metastatic and stem cell properties.

Figure 3:
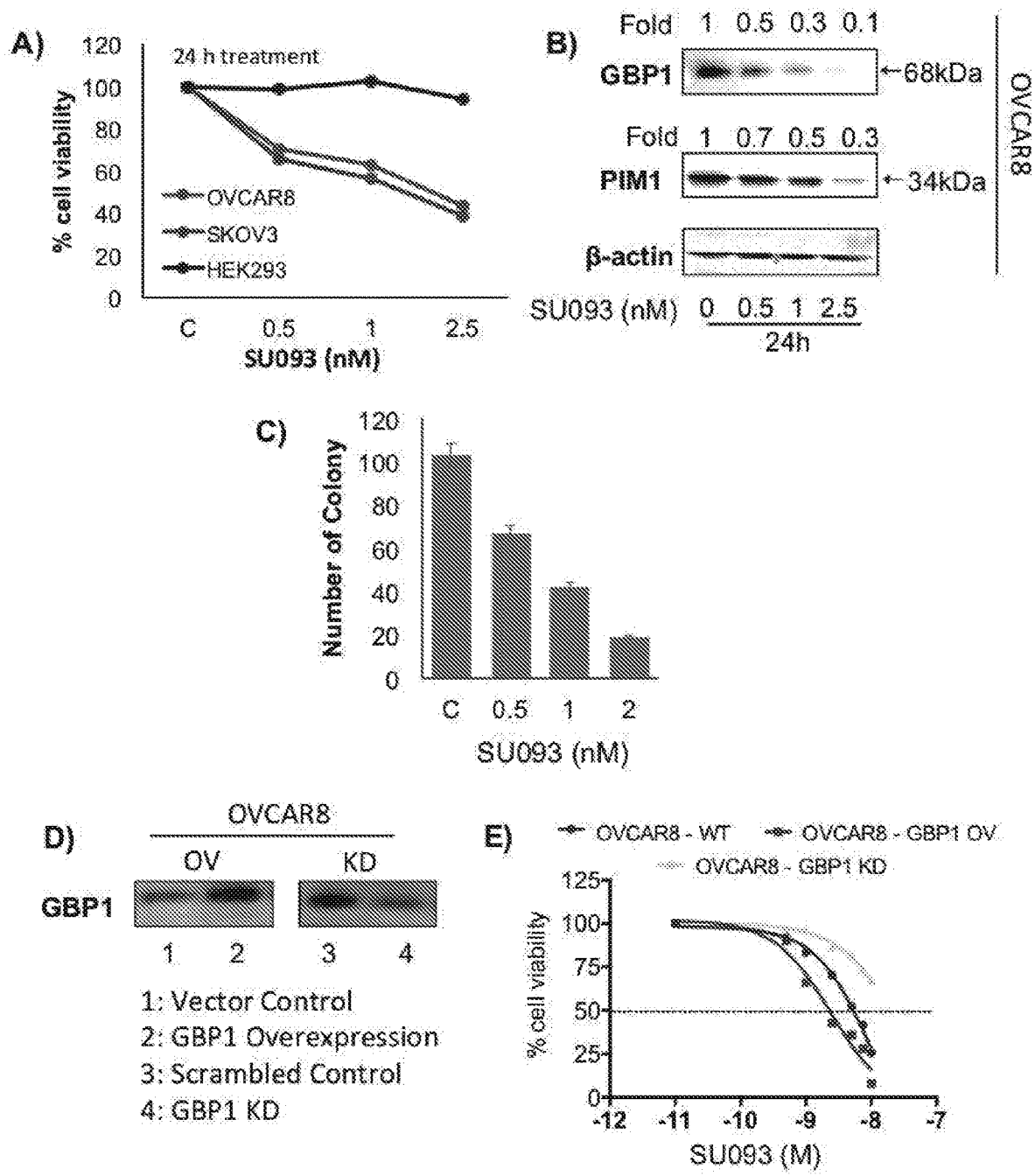
FIG. 3, panels A-E.
Figure 4:
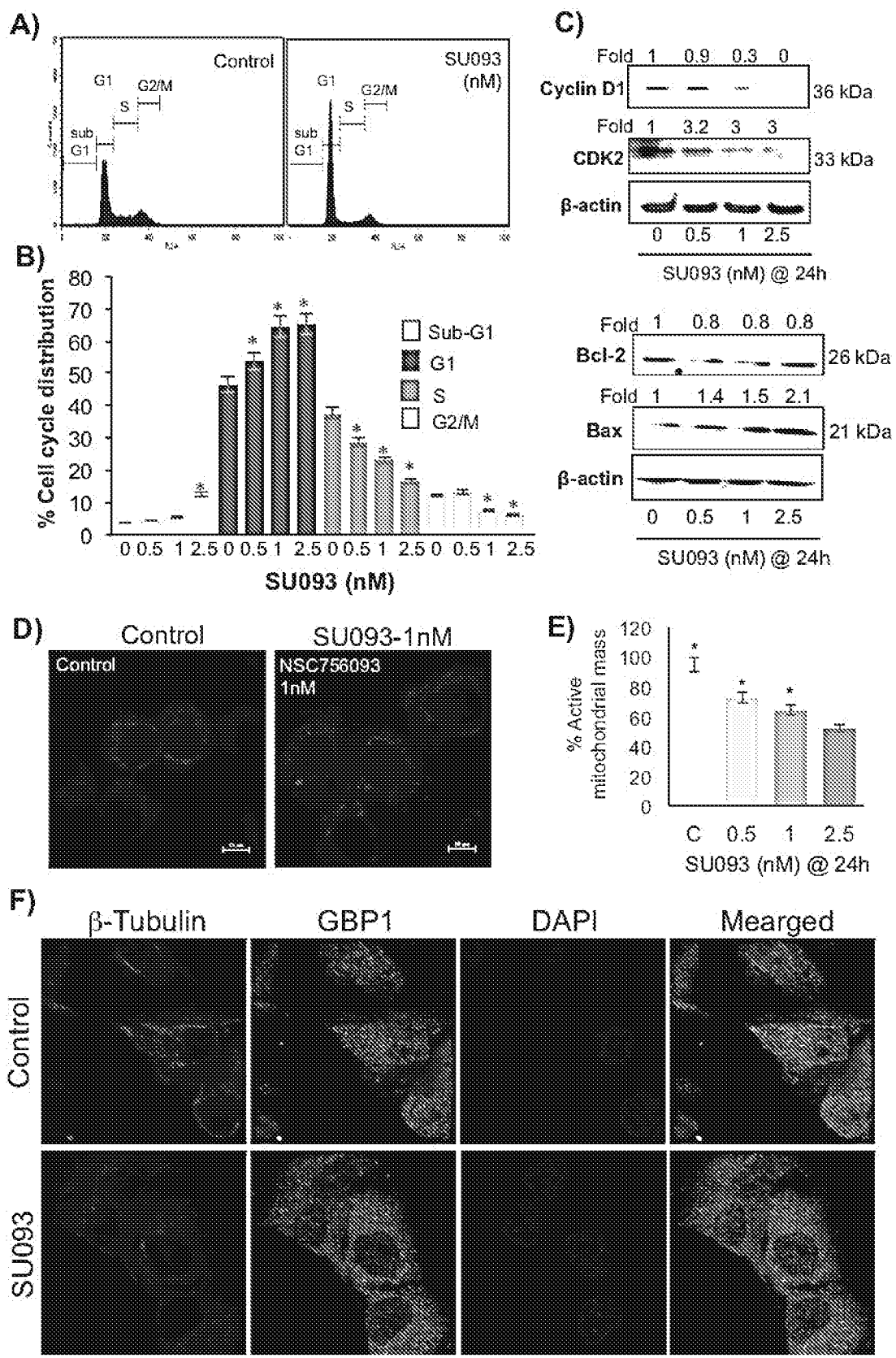
FIG. 4, panel A illustrates a histogram of cell cycle distribution of propidium iodide (PI)-stained cells.

Example 4: Mechanism of Action Studies of SU093 for GBP1 Inhibition in Ovarian Cancer GBP1 inhibitor SU093 showed dose dependent cytotoxicity for ovarian cancer cell lines OVCAR8 ($IC_{50}$=2.49 nM) and SKOV3 ($IC_{50}$=2.68 nM) but no cytotoxicity for normal ovarian cell line HEK293 (FIG. 3, panel A). Immunoblotting experiments showed that SU093 inhibits GBP1 and PIM1 expressions in a dose-dependent manner in OVCAR8 cells (FIG. 3, panel B). SU093 also showed dose-dependent inhibition of colony formation in OVCAR8 cells (FIG. 3, panel C). Furthermore, OVCAR8 cells with overexpressed (OV) and knockdown (KD) of GBP1 gene were created (FIG. 3, panel D) and cell viability experiments were performed on GBP1-WT (wild-type), GBP1-OV and GBP1-KD OVCAR8 cells at different doses of SU093. Compared to GBP1-WT, SU093 showed enhanced cytotoxicity in GBP1-KD cells and reduced cytotoxicity for GBP1-OV cells (FIG. 3, panel E). This indicates that the cytotoxicity of SU093 is mediated specifically through its action upon GBP1. Further investigation demonstrated that SU093 resulted in significant arrest of OVCAR8 cell cycle, where progression from G1 to S phase was markedly inhibited (FIG. 4, panels A and B) accompanied by reduction in cyclin D1 and CDK2 levels and elevation of the cell death regulator Bax (FIG. 4, panel C). Also, it was observed that SU093 significantly diminished active mitochondrial mass of OVCAR8 cells in a dose-dependent manner (FIG. 4, panels D and E), suggesting a decrease in proliferative capacity.

Immunostaining experiments using confocal microscopy showed that SU093 inhibits GBP1 by blocking its nuclear translocation and reducing tubulin expression (FIG. 4, panel F). α- and β-tubulin are heterodimers and are involved in mitosis, cell movement and intracellular trafficking (Parker, A. L.; Kavallaris, M.; McCarroll, J. A., Microtubules and their role in cellular stress in cancer. *Frontiers in Onclology* 2014, 4 (153), 1-19). Confocal observations suggested that inhibition of GBP1 may block the heterodimer formation and inhibits the cell migration.

Figure 5:
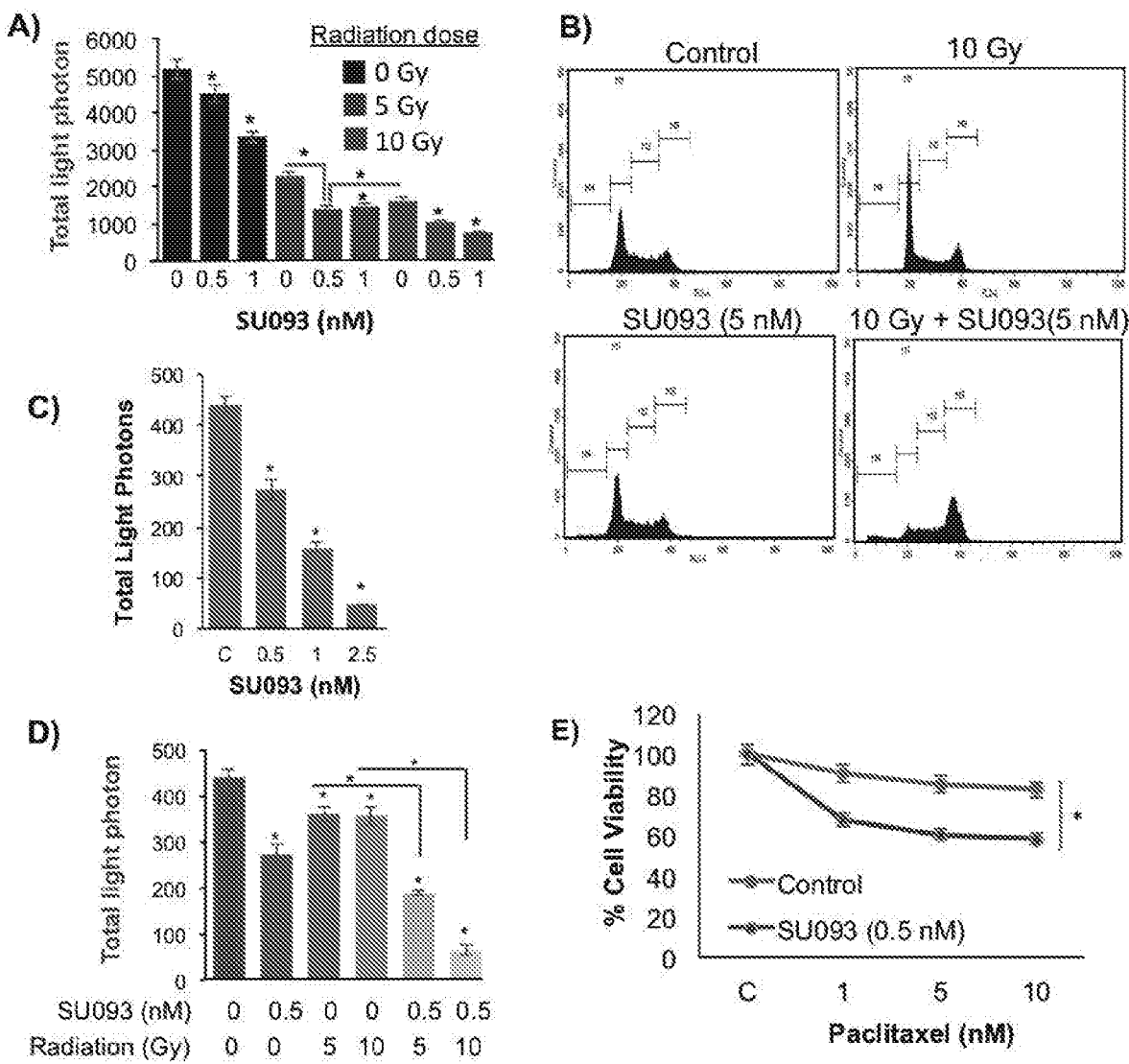
FIG. 5, panels A-E: illustrates the sensitizing effect of SU093 on the viability of luciferase-tagged OVCAR8 cells in combination with radiation and chemotherapy treatment.

Example 5: GBP1 Inhibition to Overcome Radiation Therapy and Chemotherapy Resistance in Ovarian Cancer Cells It has been previously established that GBP1 expression has a definitive role in the resistance towards radiation therapy and taxane-based chemotherapy. The GBP1 inhibitor SU093 was tested in combination with radiation and paclitaxel (a well known taxane-based chemotherapeutic drug) for its potential in overcoming radiation therapy and taxane resistance. When Luciferase-tagged OVCAR8 cells pretreated with SU093 were exposed to different doses of radiation (5 and 10 Gy), a significant synergistic effect was observed on the cell viability (FIG. 5, panel A). Combination of 0.5 nM SU093 with 5 Gy radiation treatment exhibited similar effect as 10 Gy treatment of radiation alone. A cell cycle analysis experiment for radiation was performed with SU093 and combination treatment (FIG. 5, panel B). Results revealed that, while treatment with radiation alone and SU093 alone leads to G1 phase arrest, the combination treatment (i.e. of SU093 and radiation) showed G2/M phase arrest leading to apoptotic cell death. One of the mechanisms through which a drug can sensitize the effect of radiation is its ability to block G2/M phase of the cell cycle (Leonard, C. E.; Chan, D. C.; Chou, T. C.; Kumar, R.; Bunn, P. A., Paclitaxel enhances in vitro radiosensitivity of squamous carcinoma cell lines of the head and neck. *Cancer Research*

1996, 56 (22), 5198-5204). G2/M is the most radiosensitive phase in the cell cycle and arresting the cell population in this phase would likely sensitize them to the next cycle of radiation and enhance cell death (Pawlik, T. M.; Keyomarsi, K., Role of cell cycle in mediating sensitivity to radiotherapy. *International Journal of Radiation Oncology Biology Physics* 2004, 59 (4), 928-942; Nambiar, D. K.; Rajamani, P.; Deep, G.; Jain, A. K.; Agarwal, R.; Singh, R. P., Silibinin Preferentially Radiosensitizes Prostate Cancer by Inhibiting DNA Repair Signaling. *Molecular Cancer Therapeutics* 2015, 14 (12), 2722-2734). The demonstrated ability of SU093 to arrest maximum cell population in G2/M phase indicates its great potential as a radiosensitizing agent. Interestingly, it was also found that SU093 exerted intrinsic cytotoxic effects on OVCAR8 cells cultured in hypoxic conditions (FIG. 5, panel C). Subsequently, it was observed that co-treatment of hypoxic OVCAR8 cells with SU093 and varying doses of radiotherapy significantly potentiated cell death (FIG. 5, panel D). Bearing in mind that solid tumors create a hypoxic microenvironment, these findings provided a very compelling case for the clinical application of the subject GBP1 inhibitors as a treatment for re-sensitizing radiation therapy in refractory cancers.

The cytotoxic effect of SU093 and paclitaxel combination treatment was also studied (FIG. 5, panel E). Luciferase-tagged OVCAR8 cells pretreated with SU093 (0.5 nM) for 24 hours followed by treatment with paclitaxel at different doses showed enhanced cytotoxic effect as compared to paclitaxel alone. To further evaluate the effect of SU093 in taxane-resistance, OVCAR8 cells resistant to paclitaxel were created at up to 2 µM concentration (OVCAR8-PRes) and treated with SU093.50% inhibition in the cell growth of OVCAR8-PRes cells was observed at a 15 nM dose of SU093. Interestingly, combination treatment of SU093 (15 nM) and paclitaxel (2 µM) increased the growth inhibition of OVCAr8-PRes cells to 80%. These results demonstrate that SU093 overcome the paclitaxel resistant in vitro and that the subject GBP1 inhibitors may have significant clinical application as a treatment for re-sensitizing chemotherapy in refractory cancers.

Example 6: GBP1 Inhibition to Modulate Cell Survival Metastasis and Radiosensitization in Head and Neck Cancer (HNC)

Figure 6:
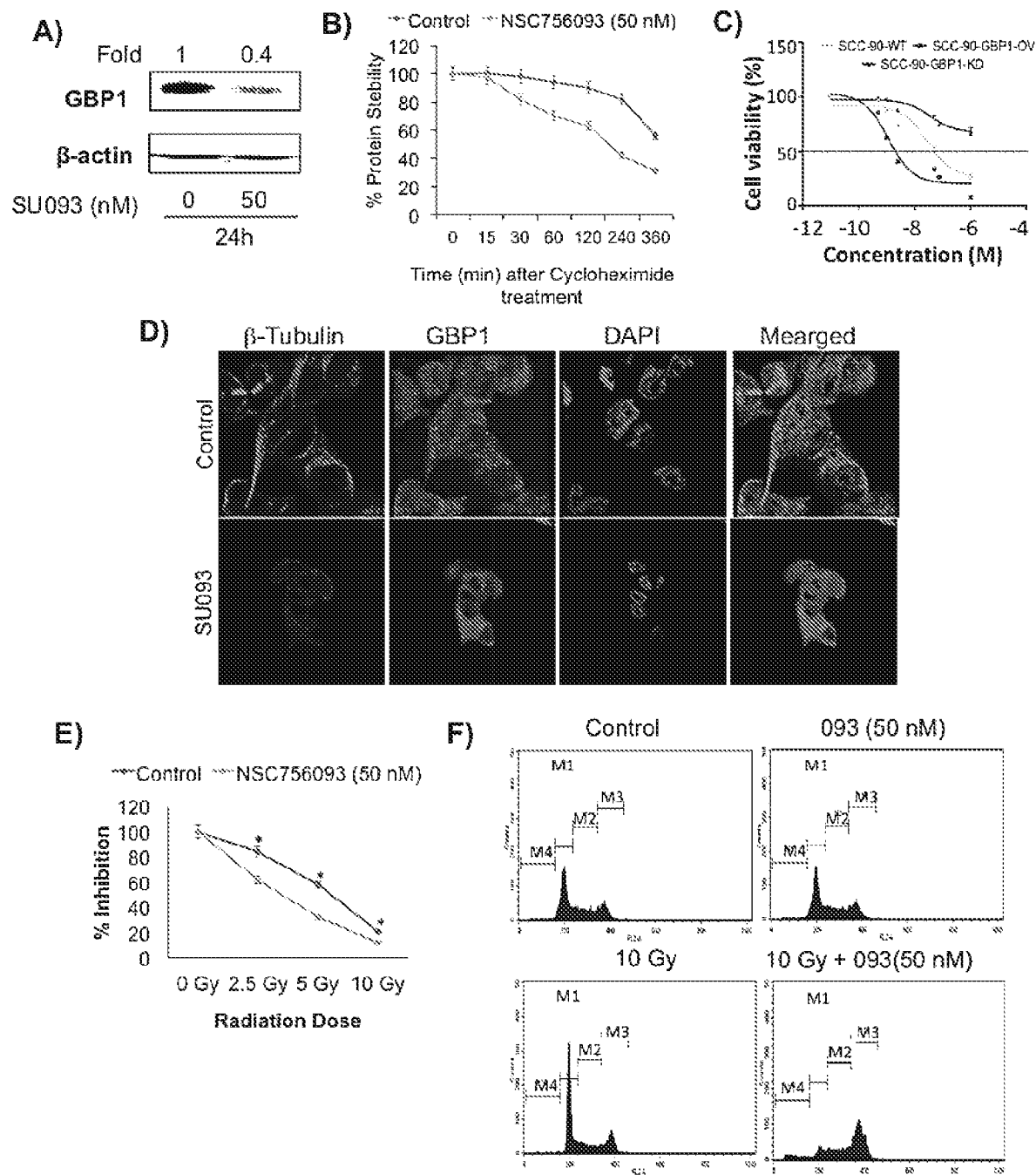
FIG. 6, panels A-F illustrate the effect of a GBP1 inhibitor (SU093) on GBP1 expression and its radiosensitization effect in SCC-90 HNC cells.

The potential for GBP1 inhibition and radiosensitzation in head and neck cancer cells was also investigated. Immunoblotting studies showed that SU093 inhibited GBP1 protein expression in SCC-90 HNC cells (FIG. 6, panel A). Cyclohexamide chase (CHX) assay suggested that SU093 treatment resulted in degradation of GBP1 protein and reduction of its half-life (FIG. 6, panel B). These results indicated that SU093 inhibited GBP1 expression by degrading the protein. Cell viability studies on SCC-90 cells with overexpression (OV) and knockdown (KD) of GBP1 gene showed GBP1 dependent cytotoxic effect on treatment with GBP1 inhibitor SU093 (FIG. 6, panel C). Confocal microscopy experiments suggested that, similar to ovarian cancer cell line OVCAR8, SU093 inhibited GBP1 expression by blocking its nuclear translocation and reducing β-tubulin expression in SCC-90 cells (FIG. 6, panel D). Results from clogenic assay performed on SCC-90 cells pretreated with SU093 at 50 nM concentration followed by radiation exposure at different dose revealed that SU093 had significant radiation sensitizing effect. Cell cycle analysis for SU093/radiation combination treatment also exhibited an increase in G2/M phase arrest, followed by apoptosis across multiple doses (FIG. 6, panel E). These results demonstrated the potential of the subject GBP1 inhibitors in drug development for combination treatment with radiation therapy.

Example 7: Pharmacokinetic and Toxicity Studies

Figure 7:
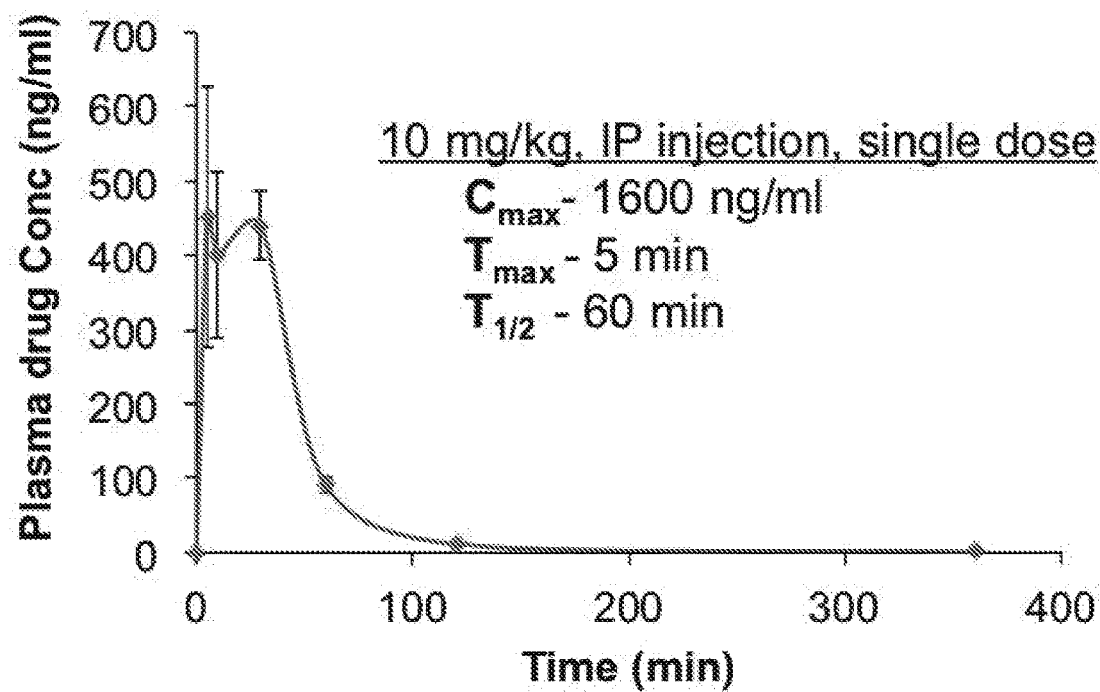
FIG. 7, panel A illustrates in vivo PK studies, C57BL/6 mice. Drug concentration in plasma was quantified at different time points using LCMS after a single IP injection of SU093.

To investigate the pharmacokinetics and toxicity of the subject GBP1 inhibitors, in vivo pharmacokinetic studies with SU093 were conducted and the drug concentration in mice plasma at different time points after injection was determined (e.g. after 5, 10, 30, 60, 120, 360 minutes after injection). Non-tumor-bearing C57BL6 female mice (n=3/group of each time point) were used for these studies and the drug was administered in a single dose of 10 mg/kg intreperatoneally (IP) at different time points. After each time point 150 microliters of blood was withdraw from retro orbital sinus from the respective group of anesthetized (isoflurane) mice. Plasma was separated from each blood sample and mixed with an equal volume of acetonitrile (w/v). Precipitated protein was separated by centrifugation at 12,000 RPM for 10 min at 4° C. Clear supernatant was analyzed for quantification of SU093 using liquid chromatography mass spectroscopy (LCMS). LCMS analysis revealed that SU093 exhibits a $C_{max}$ of 1.6 µg/ml, $T_{max}$ of 5 minutes, and $T_{1/2}$ of 60 minutes (FIG. 7, panel A).

To determine the maximum tolerable dose of an exemplary GBP1 inhibitor, SU093 was administered to C57BL6 female mice (n=10) intraperitoneally at 100 mg/kg for 14 days. Mice showed no significant weight loss or sign of toxicity. At the end of the 14$^{th}$ day, mice were sacrificed and organs were harvested. LCMS analysis revealed a concentration of 3.73 µg/ml of SU093 in the target organ (i.e. ovaries) (FIG. 7, panel B). CHEM-22 panel analysis showed only acute liver toxicity at a dose of 100 mg/kg for 14 days.

Example 8: Tumor Regression in Mouse Models

Ovarian ID-8 Tumor Xenograft:

An immunocompetent syngeneic mouse model was used to evaluate in vivo antitumor effect of SU093 and SU056 (also referred to herein as Compound (I)) for ovarian cancer. C57BL6 female mice (n=5/group) were subcutaneously injected in the right flank with 5×10$^6$ ID-8 cells mixed with matrigel. From the day following xenograft implantation, mice were monitored regularly for tumor growth and once the tumors reached approximately 100 mm$^3$, the mice were randomly divided into three groups and respective treatments were given.

Group I (vehicle control): 100 µl of 10% PEG300 (w/v) in saline;

Group II: mice treated with SU093 (20 mg/kg); and

Group III: mice treated with SU056 (20 mg/kg).

Doses were administered intraperitoneally (IP) for 7 days/week for 42 days and the mice were sacrificed on day 43. Tumor sizes were measured twice weekly using digital caliper and tumor volume was calculated by the formula: 0.5236 L1 (L2)$^2$, where L1 is long diameter, and L2 is short diameter.

Figure 8:
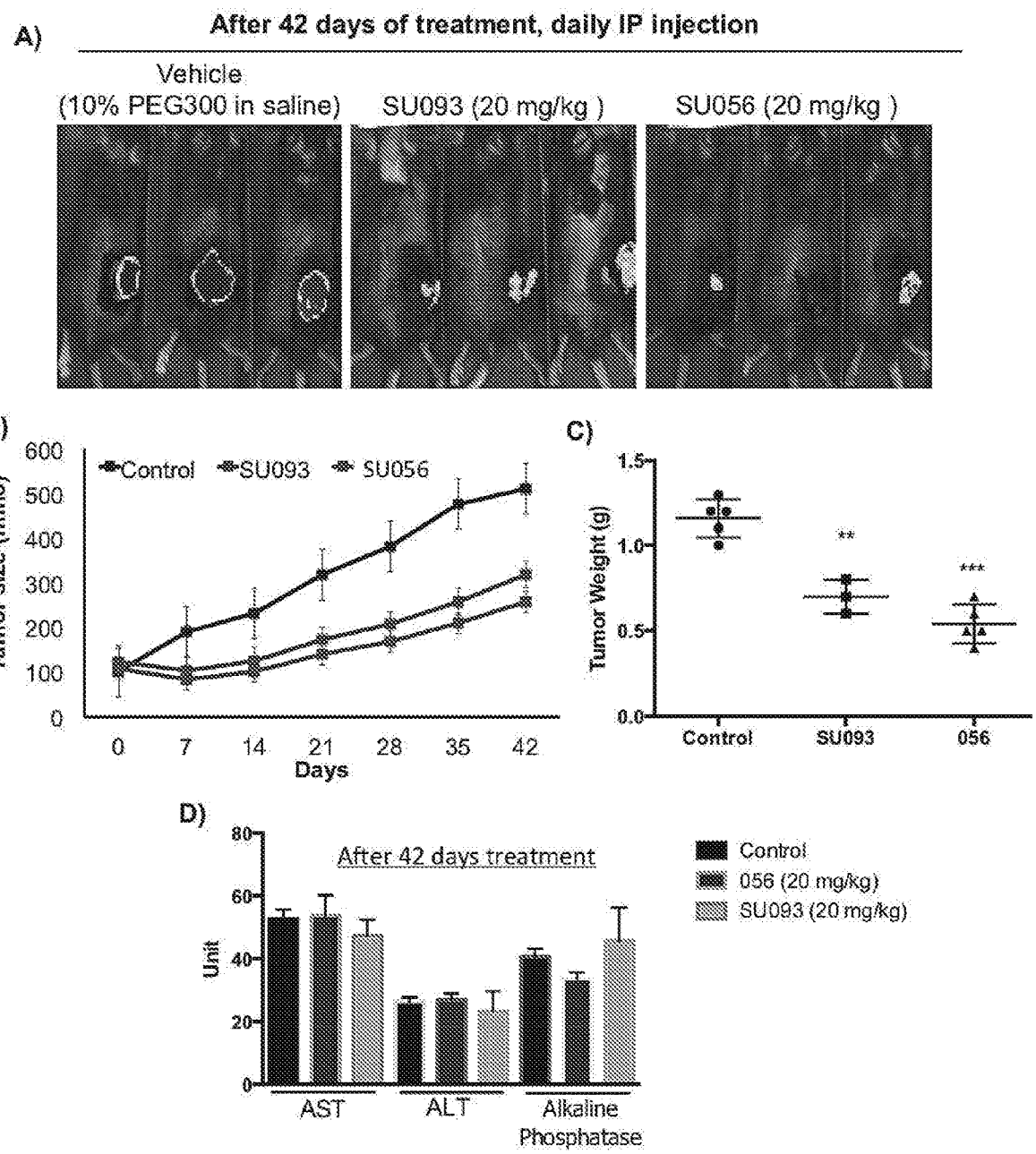
FIG. 8, panels A-D illustrate that the GBP1 inhibitors SU093 and SU056 inhibit mice ovarian ID-8 tumor xenograft growth in C57BL/6 mice.

After 42 days of treatment, a significant regression (P<0.01) in tumor volume was noted in the groups treated with SU093 and SU056 respectively, as compared to the control group (FIG. 8, panel A). At the end of 6 weeks of the study, tumor volume/mouse was calculated to be 510.27±49.54 mm$^3$, 318.81±26.09 mm$^3$ and 257.39±21.6 mm$^3$ for control, SU093 and SU056 groups respectively. This demonstrated that SU093 and SU056 treatment resulted in 37.5% and 49.55% (P=0.001) reduction in tumor volume, respectively (FIG. 8, panel B). Similarly, tumor weight in SU093 and SU056 treated groups was also decreased by 39.65% and 53.44% respectively (P<0.001) when compared with the control group (FIG. 8, panel C). Both, SU093 and SU056 treatment groups did not show any gross sign of toxicity as monitored by body weight and diet consumption. At the end of treatment liver toxicity parameters were analyzed for aspartate aminotransferase (AST), alanine aminotransferase (ALT) and Alkaline phosphatase using ELISA. No significant difference between control group, SU093 treatment group, and the SU056 treatment group was observed (FIG. 8, panel D).

Figure 9:
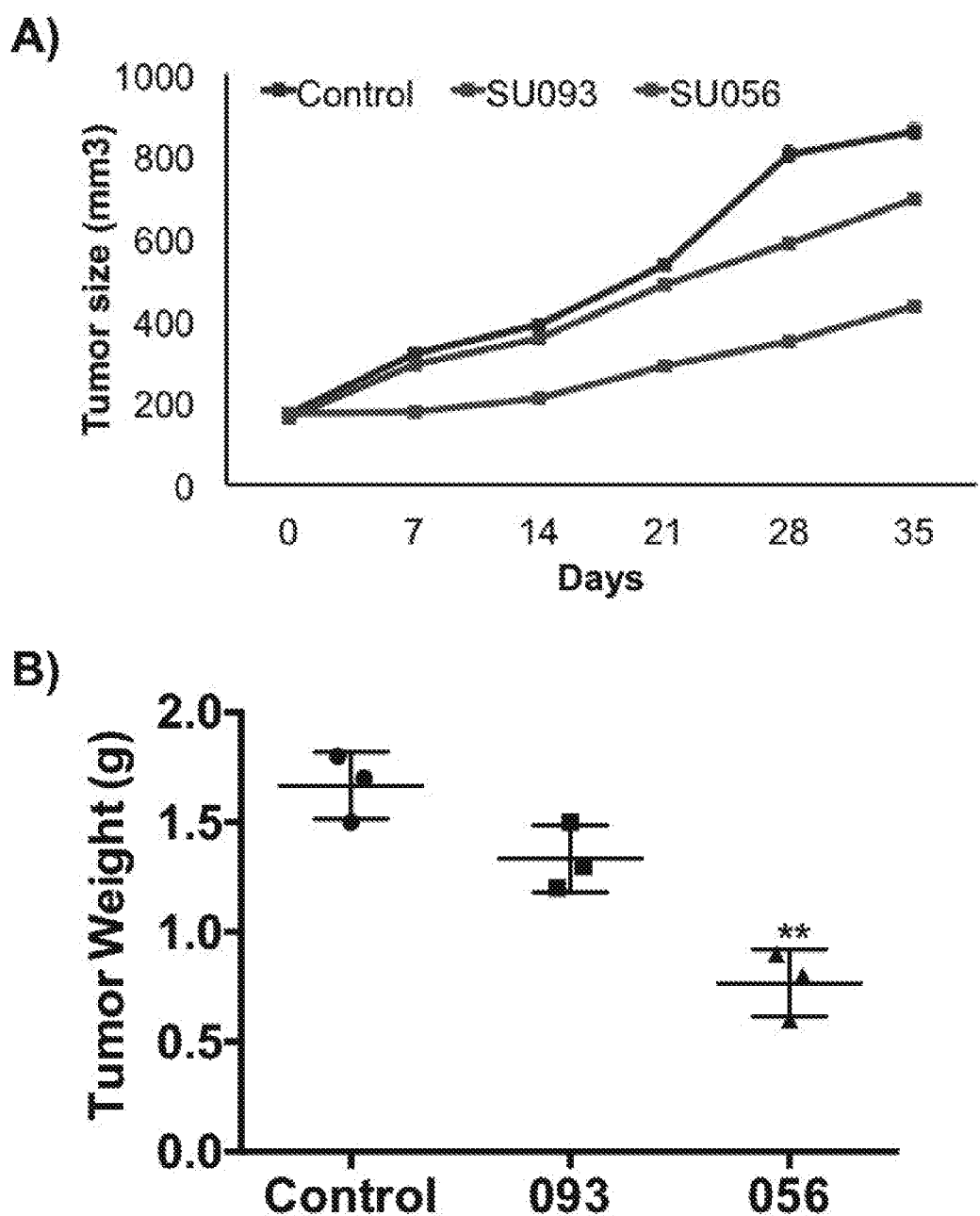
FIG. 9, panels A-B illustrate that GBP1 inhibitors SU093 and SU056 inhibit mice head and neck SCC-90 tumor xenograft growth in nude mice.

Head and Neck SCC-90 Tumor Xenograft:

An immunodeficient nude mice model was also used to study the in vivo potential of SU093 and SU056 for head and neck cancer. Nude mice (n=3/group) were subcutaneously injected in the right flank with $5\times10^6$ SCC-90 cells mixed with matrigel and observed regularly until the tumor size reached about 200 $mm^3$. The treatment regime with drugs including dose, formulation and route of delivery was similar to ovarian cancer study discussed above. Doses of SU093 and SU056 were administered daily until 35 days and mice were sacrificed thereafter. After 35 days of treatment, significant regression in tumor size and weight was observed with SU093 and SU056 treatment groups as compared to the control group (FIG. 9, panels A and B). At the end of 35 days, calculated tumor volume/mouse was 860.33±21.78 $mm^3$, 694.67±14.64 $mm^3$, and 435.00±10.81 $mm^3$ for control, SU093 and SU056 treatment groups, respectively. This equates to a 20% and 50% reduction in tumor volume for SU093 and SU056 treatment groups, respectively. A decrease in tumor weight of about 21% (P value not significant) and 54% (P<0.002) was also observed for the SU093 and SU56 treatment groups, respectively.

These in vivo studies support the in vitro findings that GBP1 inhibitors have potent cytotoxic effect. Moreover, these results indicate that SU093 and SU056 exhibit no potential toxicity liabilities and are most likely safe to administer at their desired and effective dose.

SUMMARY

Studies disclosed herein for the inhibition of GBP1 activity represents significant progress against taxane and radiation therapy resistant cancers. Specifically, the examples described herein have demonstrated that an allosteric modulator of GBP1 can restore treatment sensitivity in vitro in ovarian (OV) and head and neck cancers (HNC). The data presented illustrates that OV and HNC cells overexpressed with GBP gene increased radioresistance and hypoxic response while inducing angiogenesis and inflammation. Treatment of ovarian and HNC cells with exemplarily GBP1 inhibitors can restore radiation sensitivity and reduced hypoxia-mediated pro-survival tumor adaptation. These results established that GBP1 protein can have a significant effect in the tumor microenvironment modulation and can be a potential target for OV and HNC therapeutics. The pharmacokinetics and safety profile of exemplary GBP1 inhibitors has also been rigorously assessed. Standalone in vivo studies of GBP1 inhibitors SU093 and SU056 in mice showed significant tumor regression in ovarian cancer and head and neck cancer models with no liver toxicity. Results obtained in these studies demonstrate both the clinical potential and translational path of GBP1 inhibition for re-sensitization of refractory tumors to chemotherapy and radiation therapy.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A compound, having the structure:

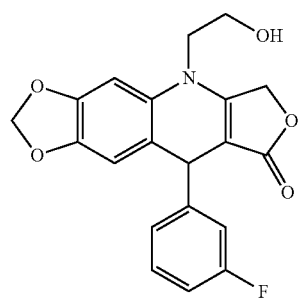 [SMILES: O=C1OCC2=C1C(c1cccc(F)c1)c1cc3c(cc1N2CCO)OCO3]

or a pharmaceutically acceptable salt or a solvate thereof.

2. A pharmaceutical composition comprising:

a compound according to claim 1; and a pharmaceutically acceptable excipient.

3. A method comprising:

contacting a cellular sample with a compound according to claim 1 to inhibit GBP1: pro-survival kinase interactions.

4. A method of treating cancer, comprising:
   administering to a subject in need thereof an effective amount of a compound according to claim 1 to inhibit GBP1: pro-survival kinase interactions and treat the subject for cancer.

5. The method of claim 4, wherein the cancer is selected from ovarian cancer (OC), colorectal cancer, prostate cancer, head and neck cancer (HNC), lung cancer and breast cancer.

6. A method of treating cancer, comprising: administering to a subject in need thereof an effective amount of a compound according to claim 1, thereby treating the subject for cancer.

7. The method of claim 6, wherein the subject is a human.

8. The method of claim 6, wherein the subject has been diagnosed with a cancer is selected from ovarian cancer (OC), colorectal cancer, prostate cancer, head and neck cancer (HNC), lung cancer and breast cancer.

9. The method of claim 6, wherein the compound is administered to the subject:
   at least once a day;
   once a day; or
   less often than once a day.

10. The method of claim 6, wherein the compound is administered to the subject for a period of:
    at least one week;
    more than one week;
    at least four weeks;
    at least 42 days; or
    more than a month.

11. The method of claim 6, wherein the compound is administered to the subject:
    in an amount from 10 pg to 100 mg per dose;
    in an amount from 50 mg to about 100 mg per dose;
    in an amount from 100 mg to 500 mg per day;
    in an amount from 500 mg to 1000 mg per day;
    at a rate of 50 ng/kg body weight to 50 µg/kg body weight;
    at a rate of up to 20 mg/kg body weight; or
    at a rate of up to 10 mg/kg body weight.

12. The method of claim 6, further comprising administering to the subject at least one additional pharmaceutically active compound.

13. The method of claim 12, wherein the at least one additional pharmaceutically active compound comprises a taxane.

14. The method of claim 12, wherein the at least one additional pharmaceutically active compound comprises a chemotherapeutic agent selected from: Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199.

15. The method of claim 12, wherein the at least one additional pharmaceutically active compound is administered separately from the compound having the structure:

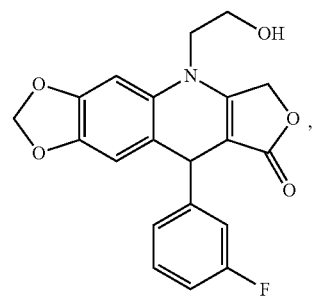 [SMILES: O=C1OCC2=C1C(c1cccc(F)c1)c1cc3c(cc1N2CCO)OCO3]

or a pharmaceutically acceptable salt or a solvate thereof.

16. The method of claim 12, wherein timing of administration of the at least one additionally active compound is varied relative to the compound to claim 1.

17. A method comprising contacting a cellular sample with a compound according to claim 1.

18. The pharmaceutical composition of claim 2, wherein one or more of:
    the composition is formulated for delivery by injection;
    the composition is formulated for oral delivery;
    the composition is formulated for intraperitoneal (IP) delivery;
    the composition is formulated in a unit dosage form; and/or
    the composition comprises at least one additional active agent.

19. A pharmaceutical composition comprising:
    a compound having the structure:

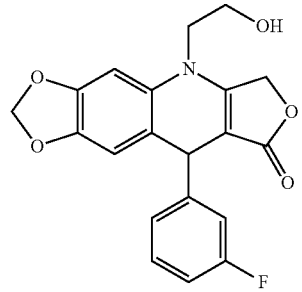 [SMILES: O=C1OCC2=C1C(c1cccc(F)c1)c1cc3c(cc1N2CCO)OCO3]

or a pharmaceutically acceptable salt or a solvate thereof;
    at least one additional pharmaceutically active agent; and
    a pharmaceutically acceptable excipient.

20. The pharmaceutical composition of claim 19, wherein the at least one additional pharmaceutically active compound comprises a taxane.

21. The pharmaceutical composition of claim 19, wherein the at least one additional pharmaceutically active compound comprises a chemotherapeutic agent selected from: Gemcitabine, Docetaxel, Bleomycin, Erlotinib, Gefitinib, Lapatinib, Imatinib, Dasatinib, Nilotinib, Bosutinib, Crizotinib, Ceritinib, Trametinib, Bevacizumab, Sunitinib, Sorafenib, Trastuzumab, Ado-trastuzumab emtansine, Rituximab, Ipilimumab, Rapamycin, Temsirolimus, Everolimus, Methotrexate, Doxorubicin, Abraxane, Folfirinox, Cisplatin, Carboplatin, 5-fluorouracil, Teysumo, Paclitaxel, Prednisone, Levothyroxine, Pemetrexed, navitoclax, and ABT-199.

* * * * *